(12) United States Patent
Saitou et al.

(10) Patent No.: US 7,488,803 B2
(45) Date of Patent: Feb. 10, 2009

(54) **ANTIBODIES TO THE EXTRACELLULAR DOMAIN OF HUMAN *FRAGILIS* POLYPEPTIDE AND METHODS OF MAKING SAID ANTIBODIES**

(75) Inventors: Mitinori Saitou, Cambridge (GB); Azim Surani, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 147 days.

(21) Appl. No.: 11/038,676

(22) Filed: Jan. 18, 2005

(65) Prior Publication Data

US 2006/0035326 A1    Feb. 16, 2006

(51) Int. Cl.
*C07K 16/00* (2006.01)
*C07K 16/18* (2006.01)
*C07K 16/28* (2006.01)
*C12P 21/08* (2006.01)

(52) U.S. Cl. .............. 530/387.1; 530/387.3; 530/387.9; 530/388.1; 435/69.1; 435/70.21

(58) Field of Classification Search ....................... None
See application file for complete search history.

(56) References Cited

U.S. PATENT DOCUMENTS

2003/0092037 A1 * 5/2003 Matsuzaki et al. ............. 435/6

FOREIGN PATENT DOCUMENTS

| WO | 99/54353 | 10/1999 |
|---|---|---|
| WO | 01/75177 A2 | 10/2001 |
| WO | 01/77389 A2 | 10/2001 |
| WO | 01-94629 A2 | 12/2001 |
| WO | 02/12328 A2 | 2/2002 |
| WO | 02/29103 A2 | 4/2002 |
| WO | 02/057307 A2 | 7/2002 |
| WO | 02/103028 A2 | 12/2002 |

OTHER PUBLICATIONS

Deblandre, et al.; "Expression Cloning of an Interferon-inducible 17-kDa Membrane Protein Implicated in the Control of Cell Growth"; Journal of Biological Chemistry(1995); vol. 270(40); pp. 23860-23866.

Lewin, et al.; "Molecular Analysis of a Human Interferin-Inducible Gene Family"; European Journal of Biochemistry(1991); vol. 199(2); pp. 417-423.
Reid, et al.; "A Single DNA Response Element Can Confer Inducibility by Both α and γ-Interferons"; Biochemistry(1989); vol. 86(3); pp. 840-844.
Saitou, et al.; "A Molecular Programme for the Specification of Germ Cell Fate in Mice"; Nature(2002); vol. 418(6895); pp. 293-300.
Sato, et al; "Identification of PGC7, A New Gene Expressed Specifically in Preimplantation Embryos and Germ Cells"; nature, MacMillan Journals Ltd. London(2002); pp. 293-300.
Database EMBL 'Online!; Saitou, et al.; "Specification of Germ Cell Fate in Mice"; Database Accession No. Q99J93, (2002).
Database EMBL 'Online!; Kawai, et al; "Functional Annotation of a Full Length Mouse cDNA Collection"; Database Accession No. Q9D3R8, (2004).
Database EMBL 'Online!; Kawai, et al.; "Functional Annotation of a full Length Mouse cDNA Collection"; Database Accession No. Q9D103, (2005).
Database EMBL 'Online!; Kawai, et al.; "Differenciating Embryonal Stem Cell are a Rich Source of Haematopoietic Gene Products and Suggest Erythroid Preconditioning of Primitive Haematopoietic Stem Cells"; Database Accession No. 088728, (2005).
Database EMBL 'Online! Human Chromosome 14, Data Accession No. AL137226, (2000).
Database EMBL 'Online!; Database Accession No. AA927342, (1998).
Database EMBL 'Online!; Database Accession No. BQ 233055, (2002).
Database EMBL 'Online!; "Human 1-8D Gene From Interferon-inducible Gene f"; Database Accession No. X57351, (1993).

* cited by examiner

*Primary Examiner*—David Romeo
*Assistant Examiner*—Daniel C Gamett
(74) *Attorney, Agent, or Firm*—Whyte Hirschboeck Dudek, S.C.

(57) ABSTRACT

The present invention relates to two primordial germ cell-specific expressed genes, *Fragilis* and *Stella*. The sequences and sues of human *Stella* and *Fragilis* are disclosed herein, as are several mouse sequences related to *Fragilis*. The present invention relates to the use of *Stella* and *Fragilis* as markers for primordial germ cells and can be used to identify such cells. Additionally, the present invention relates to the use of *Stella* and *Fragilis* for the diagnosis, treatment and/or prevention of disease.

16 Claims, 31 Drawing Sheets

FIG. 1

```
GCCGCAGAAAGGGCAGACCCGCAGCGCGCTCCATCCTTTGCCCTCCAGTGCTGCCTTTGC    60
TCCGCACCATGAACCACACTTCTCAAGCCTTCATCACGGCTGCCAGTGGAGGACAGCCCC   120
          M  N  H  T  S  Q  A  F  I  T  A  A  S  G  G  Q  P  P

CAAACTACGAAAGAATCAAGGAAGAATATGAGGTGGCTGAGATGGGGGCACCGCACGGAT   180
   N  Y  E  R  I  K  E  E  Y  E  V  A  E  M  G  A  P  H  G  S

CGGCTTCTGTCAGAACTACTGTGATCAACATGCCCAGAGAGGTGTCGGTGCCTGACCATG   240
   A  S  V  R  T  T  V  I  N  M  P  R  E  V  S  V  P  D  H  V

TGGTCTGGTCCCTGTTCAATACACTCTTCATGAACTTCTGCTGCCTGGGCTTCATAGCCT   300
   V  W  S  L  F  N  T  L  F  M  N  F  C  C  L  G  F  I  A  Y
              TMI

ATGCCTACTCCGTGAAGTCTAGGGATCGGAAGATGGTGGGTGATGTGACTGGAGCCCAGG   360
   A  Y  S  V  K  S  R  D  R  K  M  V  G  D  V  T  G  A  Q  A

CCTACGCCTCCACTGCTAAGTGCCTGAACATCAGCACCTTGGTCCTCAGCATCCTGATGG   420
   Y  A  S  T  A  K  C  L  N  I  S  T  L  V  L  S  I  L  M  V
                                    TMII

TTGTTATCACCATTGTTAGTGTCATCATCATTGTTCTTAACGCTCAAAACCTTCACACTT   480
   V  I  T  I  V  S  V  I  I  I  V  L  N  A  Q  N  L  H  T  *

AATAGAGGATTCCGACTTCCGGTCCTGAAGTGCTTCACCCTCCGCAGCTGCGTCCCTCCT   540
TGCCCCTCCCTACACGCAGGTGTAACACTCATTTATCTATCCACAGTGGATTCAATAAAG   600
TGCACTTGATAACCACC
```

FIG. 2

```
GGATCACAGACTGACTGCTAATTGGGTCTTGGTTTTAGGTCTTTTCAAAGACTAAGCAAT  60
CTTGTTCCGAGCTAGCTTTTGAGGCTTCTGCCCATCGCATCGCCATGGAGGAACCATCAG 120
                                          M  E  E  P  S  E

AGAAAGTCGACCCAATGAAGGACCCTGAAACTCCTCAGAAGAAAGATGAAGAGGACGCTT 180
 K  V  D  P  M  K  D  P  E  T  P  Q  K  K  D  E  E  D  A  L

TGGATGATACAGACGTCCTACAACCAGAAACACTAGTAAAGGTCATGAAAAAGCTAACCC 240
 D  D  T  D  V  L  Q  P  E  T  L  V  K  V  M  K  K  L  T  L
                                                  ─────────── Helix I
TAAACCCCGGTGTCAAGCGGTCCGCACGCCGGCGCAGTCTACGGAACCGCATTGCAGCCG 300
 N  P  G  V  K  R  S  A  R  R  R  S  L  R  N  R  I  A  A  V
 ───────────────────────────────────────────────────
                                    ──────────────────────── Helix II
TACCTGTGGAGAACAAGAGTGAAAAAATCCGGAGGGAAGTTCAAAGCGCCTTTCCCAAGA 360
 P  V  E  N  K  S  E  K  I  R  R  E  V  Q  S  A  F  P  K  R
 ────

GAAGGGTCCGCACTTTGTTGTCGGTGCTGAAAGACCCTATAGCAAAGATGAGAAGACTTG 420
 R  V  R  T  L  L  S  V  L  K  D  P  I  A  K  M  R  R  L  V
                            ────────────────────────────────
TTCGGATTGAGCAGAGACAAAAAAGGCTCGAAGGAAATGAGTTTGAACGGACAGTGAGC 480
 R  I  E  Q  R  Q  K  R  L  E  G  N  E  F  E  R  D  S  E  P
 ───────────────────────────────────────────────────

CATTCAGATGTCTCTGCACTTTCTGCCATTATCAAAGATGGGATCCCTCTGAGAATGCGA 540
 F  R  C  L  C  T  F  C  H  Y  Q  R  W  D  P  S  E  N  A  K
 ─

AAATCGGGAAGAATTAGGAGCTTACATTGTACGCTGCCCTGGCTGTCGACGATGCCGCAC 600
 I  G  K  N  *

AGCAGATGTGAAAGCTATTTTTTGTTTAAGATTAAACTTTTTCTCGGTGCTGGGAAATCTT 660
AACTTGTTAACCTTTAAATTGTAGATAGGATGCACAACGATCCAGATTTATGTGAAGTTT 720
AGAAGCCTCAAGCTGTGAGGCCCAGGGCTGAGGAATAAAGTAAATAGAATTTGGAGTATG 780
TACGTTCTAATTTCCAGAAATTTGTAATAAAAGCATTTTTGTT
```

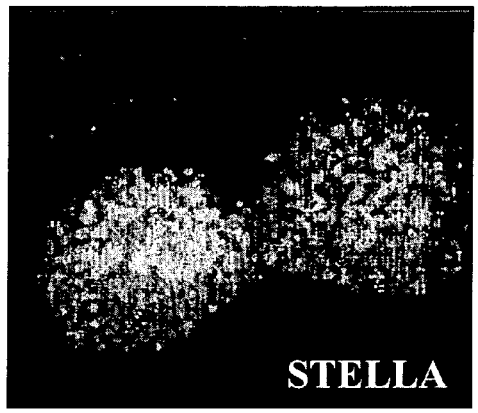
FIG. 3a STELLA
FIG. 3b TOTO3
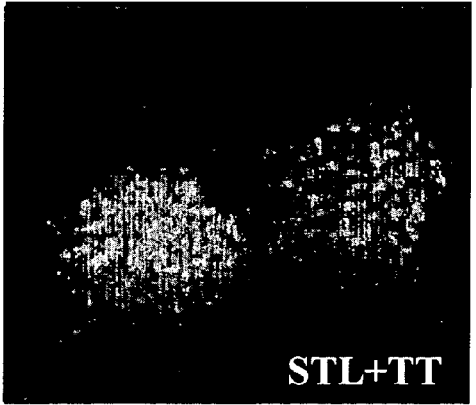
FIG. 3c STL+TT
FIG. 3d Merged

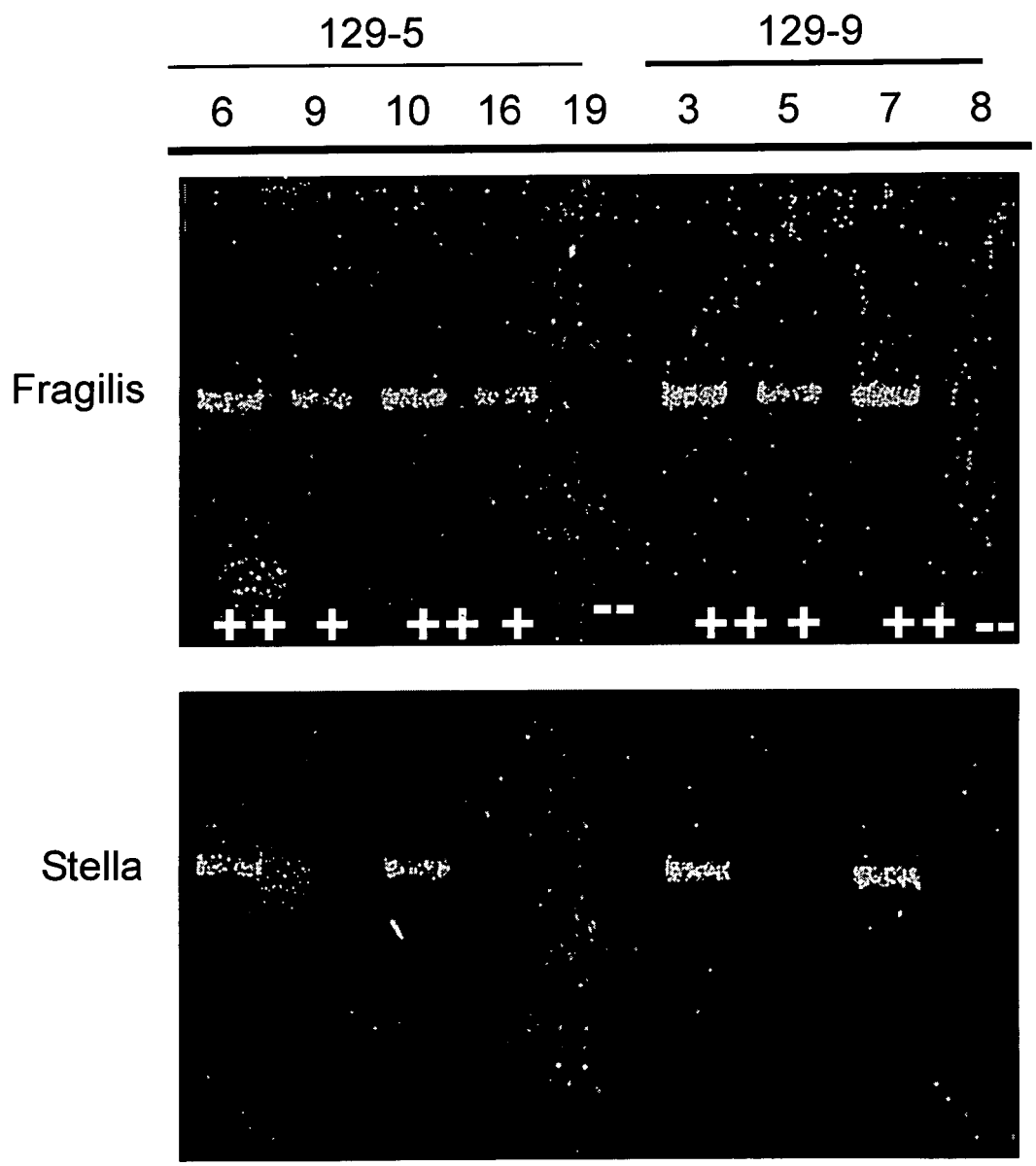

| Exp. No. | 1 | 2 | 3 | 4 | 5 |
|---|---|---|---|---|---|
| Clone No. | 1 9* 10* 11 17 | 24* 27 30* 34 | 46* 49 50* 69 76* 77 | | 81 83* 85 87* 88 89 98* |
Hoxb-1
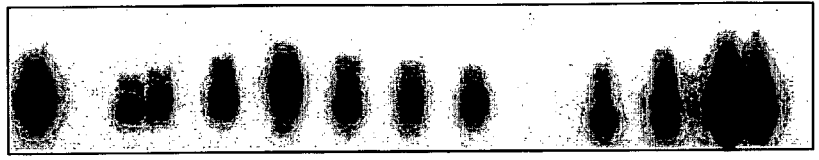
1  9 10 11 17   24 27 30 34   46 49 50 69 76 77      81 83 85 87 88 89 98
Fragilis
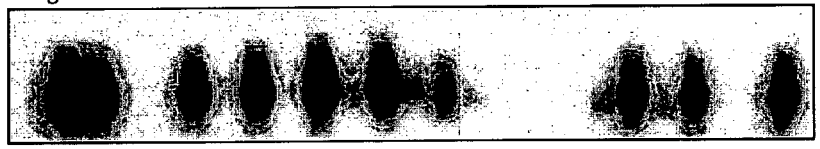
1  9 10 11 17   24 27 30 34   46 49 50 69 76 77      81 83 85 87 88 89 98
Stella
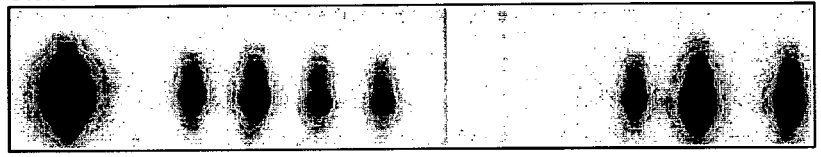
1  9 10 11 17   24 27 30 34   46 49 50 69 76 77      81 83 85 87 88 89 98
Evx1
1  9 10 11 17   24 27 30 34   46 49 50 69 76 77      81 83 85 87 88 89 98
Oct4
1  9 10 11 17   24 27 30 34   46 49 50 69 76 77      81 83 85 87 88 89 98
T(Brachyury)
1  9 10 11 17   24 27 30 34   46 49 50 69 76 77      81 83 85 87 88 89 98
Fgf8
FIG. 8b

FIG. 10a

|  | 10 | 20 | 30 | 40 |
|---|---|---|---|---|
| fragilis (mouse) | MNHTSQAF I TAA | SGGQPPNYE | R I KEEYEVAEMGAP | HG - - S |
| fragilis 2 (mouse) |  | MPKEQQEV | VVLGSP | HI - - S |
| fragilis 3 (mouse) | MSHNSQAFLSTNAG | - LPPSYE | T I KEEYGVTELGEP | SN - - S |
| fragilis 4 (mouse) |  |  | MDTSYPREDPRAP | SSRKA |
| fragilis 5 (mouse) |  | MVKRD | - - - - - - - PD | - - - S |
| Ifitm1 (human) |  |  | MHKEEHEVAVLGAP | PS - - T |
| Ifitm2 (human) | MNH I VQTFS - PVNS | GQPPNYE | MLKEEQEVAMLGGP | HN - - P |
| Ifitm3 (human) | MSHTVQTFFSPVNS | GQPPNYE | MLKEEHEVAVLGGP | HN - - P |
| novel (human) |  |  | MDTAYPREDTRAPT | P - - S |
| 1-8U (cow) | MNRTSQLLLTGAHGAV | PRAYE | VLKEEHEVAVLGAPQ | S - - Q |
| 9-27 (cow) |  |  | MIKEEHEVAVLGAPQ | S - - R |
| P26376 (rat) | MNHTSQAFVNAA | TGGQPPNYE | R I KEEYEVSELGAP | HG - - S |
| JC1241 (rat) | MNHTSQAFATVA | TGGQPPNYE | R I KEEYEVSELGAP | HG - - S |
| NP110460 (rat) | MSHNSQAFLPANAG | - LPPSYE | T I KEEYGVTELGEP | NN - - S |
| AAD48010 (rat) | MNHTSQAFVNAA | TGGQPPNYE | R I KEEYEVSELGAP | HG - - S |
|  | MNHTSQAF A | GGQPPNYE | , KEEYEV . LGAP | RKS |

|  | 50 | 60 | 70 | 80 |
|---|---|---|---|---|
| fragilis (mouse) | ASVRTTV I NMPREVSVP | - DHVVWSLFNTLFMNFCCLGF I A |
| fragilis 2 (mouse) | TSATATT I NMP - E I STP | - DHVVWSLFNTLFMNFCCLGFVA |
| fragilis 3 (mouse) | AVVRTTV I NMPREVSVP | - DHVVWSLFNTLFFNACCLGFVA |
| fragilis 4 (mouse) | DAAHTALSMGTPGPTPRDHMLWSVFSTMYLNLCCLGFLA |
| fragilis 5 (mouse) | APVPSTVVC I NSDV I QP | - DH I TWSTFNTVFMNGCCLGF I A |
| Ifitm 1 (human) | I LPRSTV I NIHSETSVP | - DHVVWSLFNTLFLNWCCLGF I A |
| Ifitm 2 (human) | APPTSTV I HIRSETSVP | - DHVVWSLFNTLFMNTCCLGF I A |
| Ifitm 3 (human) | APPTSTV I HIRSETSVP | - DHVVWSLFNTLFMNPCCLGF I A |
| novel (human) | KAGAHTALTLGAPHPPRDHL I WSVFSTLYLNLCCLGFLA |
| 1-8U (cow) | APLTTTV I N I RSDTAVP | - DH I VWSLFNT I FMNWCCLGFVA |
| 9-27 (cow) | RPLTTTV I N I RSDTAVP | - DH I VWSLFNT I FLNWCCLGFVA |
| P26376 (rat) | ASVRTTV I NMPREVSVP | - DHVVWSLFNTLFMNFCCLGF I A |
| JC1241 (rat) | ASVRTTV I NMPREVSVP | - DHVVWSLFNTLFMNFCCLGF I A |
| NP110460 (rat) | AVVRTTV I NMPREVSVP | - DHVVWSLFNTLFFNACCLGF I A |
| AAD48010 (rat) | ASVRTTV I NMPREVSVP | - DHVVWSLFNTLFMNFCCLGF I A |
|  | A . TTV I NM E , SVPRDHVVWSLFNTLFMN . CCLGF I A |

FIG. 10b

| | 90 | 100 | 110 | 120 |
|---|---|---|---|---|
| fragilis (mouse) | Y A Y S V K S R D R K M V G D | V T G A Q A Y A S T A K C L N I | S T L V L S I L M |
| fragilis 2 (mouse) | Y A Y S V K S R D R K M V G D | T T G A Q A F A S T A K C L N I | S S L F F T I L T |
| fragilis 3 (mouse) | Y A Y S V K S R D R K M V G D | V G A Q A Y A S T A K C L N I | S S L I F S I L M |
| fragilis 4 (mouse) | L V H S V K A R D Q K M A G N | L E A A R Q Y G S K A K C Y N I | L A A M W T L V P |
| fragilis 5 (mouse) | Y I Y S V K S R D R K M V G D | M T G A Q S H A S T A K I L N I | L A L V I S L I F |
| Ifitm 1 (human) | F A Y S V K S R D R K M V G D | V T G A Q A Y A S T A K C L N I | W A L I L G I L M |
| Ifitm 2 (human) | F A Y S V K S R D R K M V G D | V T G A Q A Y A S T A K C L N I | W A L I L G I F M |
| Ifitm 3 (human) | F A Y S V K S R D R K M V G D | V T G A Q A Y A S T A K C L N I | W A L I L G I L M |
| novel (human) | L A Y S I K A R D Q K V V G D | L E A A R R F G S K A K C Y N I | L A A M W T L V P |
| 1-8U (cow) | F A Y S V K S R D R K M V G D | I T G A Q S Y A S T A K C L N I | C S L V L G I L L |
| 9-27 (cow) | F A Y S V K S R D R K M V G D | I T G A Q S Y A S T A K C L N I | W A L V L G I L L |
| P26376 (rat) | Y A Y S V K S R D R K M V G D | M T G A Q A Y A S T A K C L N I | S S L V L S I L M |
| JC1241 (rat) | Y A Y S V K S R D R K M V G D | M T G A Q A Y A S T A K C L N I | S S L V L S I L M |
| NP110460 (rat) | Y A Y S V K S R D R K M V G D | V I G A Q A Y A S T A K C L N I | S S L I F S V L M |
| AAD48010 (rat) | Y A Y S V K . . . . . . . . . | . . . . . . . . . . . . . . . . | . . . . V S V L E |
| | Y A Y S V K S R D R K M V G D . T G A Q A Y A S T A K C L N I | | L . L . I L M |

| | 130 | 140 | 150 | 160 |
|---|---|---|---|---|
| fragilis (mouse) | V V I T I V S V I I I V L N A Q N L H T |
| fragilis 2 (mouse) | A I V V I V V C A I R |
| fragilis 3 (mouse) | V I I C L I I F S T T S V V V F Q S F A Q R T P H S G F |
| fragilis 4 (mouse) | P L L L L G L V V T G A L H L S K L A K D S A A F F S T K F D E E D Y N |
| fragilis 5 (mouse) | Y I M L I V L Y S F N L L G N Q R |
| Ifitm 1 (human) | T I G F I L L L V F G S V T V Y H I M L Q I I Q E K R G Y |
| Ifitm 2 (human) | T I L L V I I P V L V V Q A Q R |
| Ifitm 3 (human) | T I L L I V I P V L I F Q A Y G |
| novel (human) | P L L L L G L V V T G A L H L A R L A K D S A A F F S T K F D D A D Y D |
| 1-8U (cow) | T V V L I V L V S N G S L M I V Q A V S E L M Q N Y G G H |
| 9-27 (cow) | T I G S I V L L I F G Y M A V Y Q T V F L L M Q E K R G H |
| P26376 (rat) | V I I T I V T V V I I A L N A P R L Q T |
| JC1241 (rat) | V I I T I V T V V I I A L N A P R L Q T |
| NP110460 (rat) | V I I C L I I F S T T S A V V F Q S L S Q R T P H S G F |
| AAD48010 (rat) | V G V M V |
| | I . I V . . . . L . | | F D D Y |

FIGS. 11A-I'
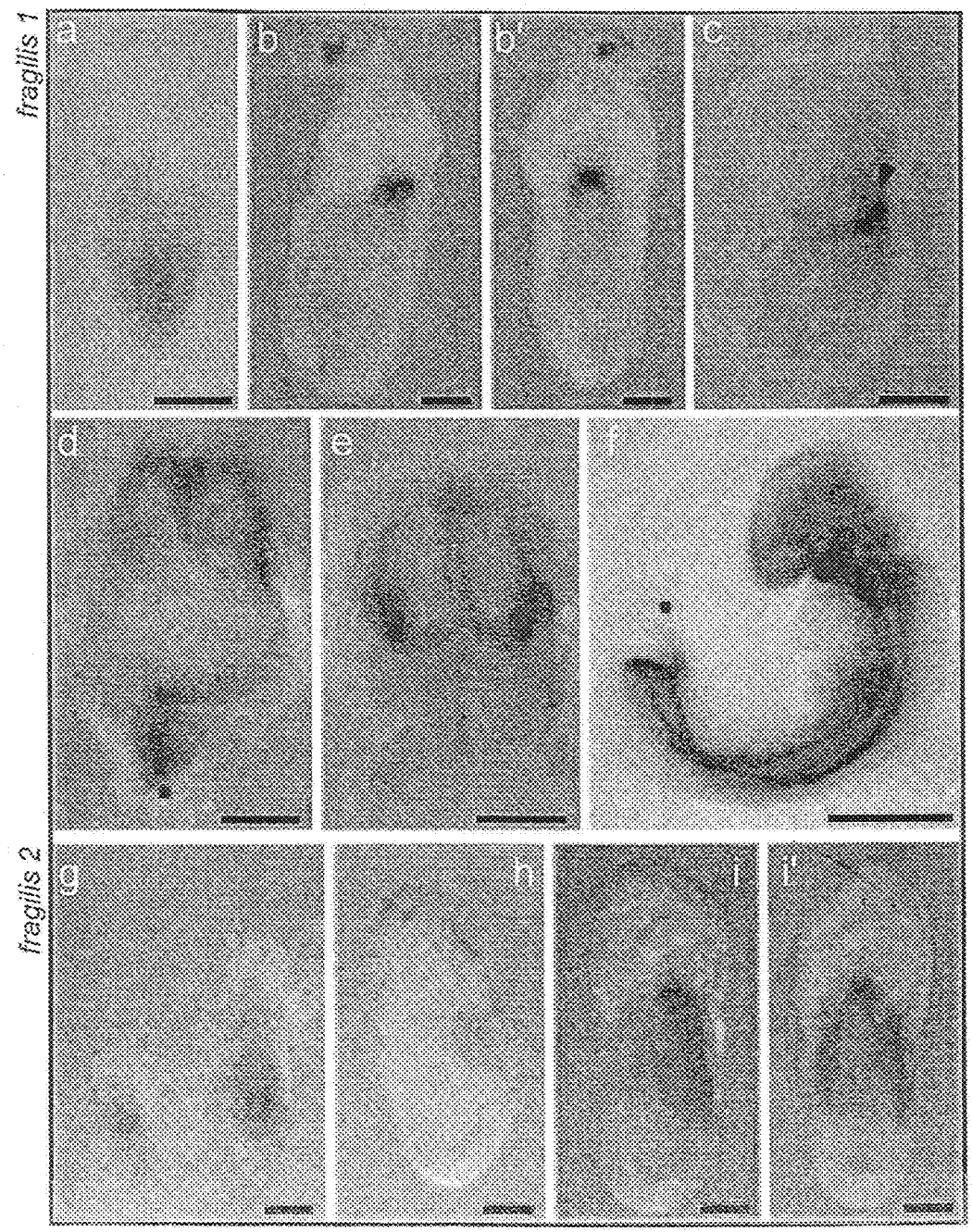

FIGS. 11J-R
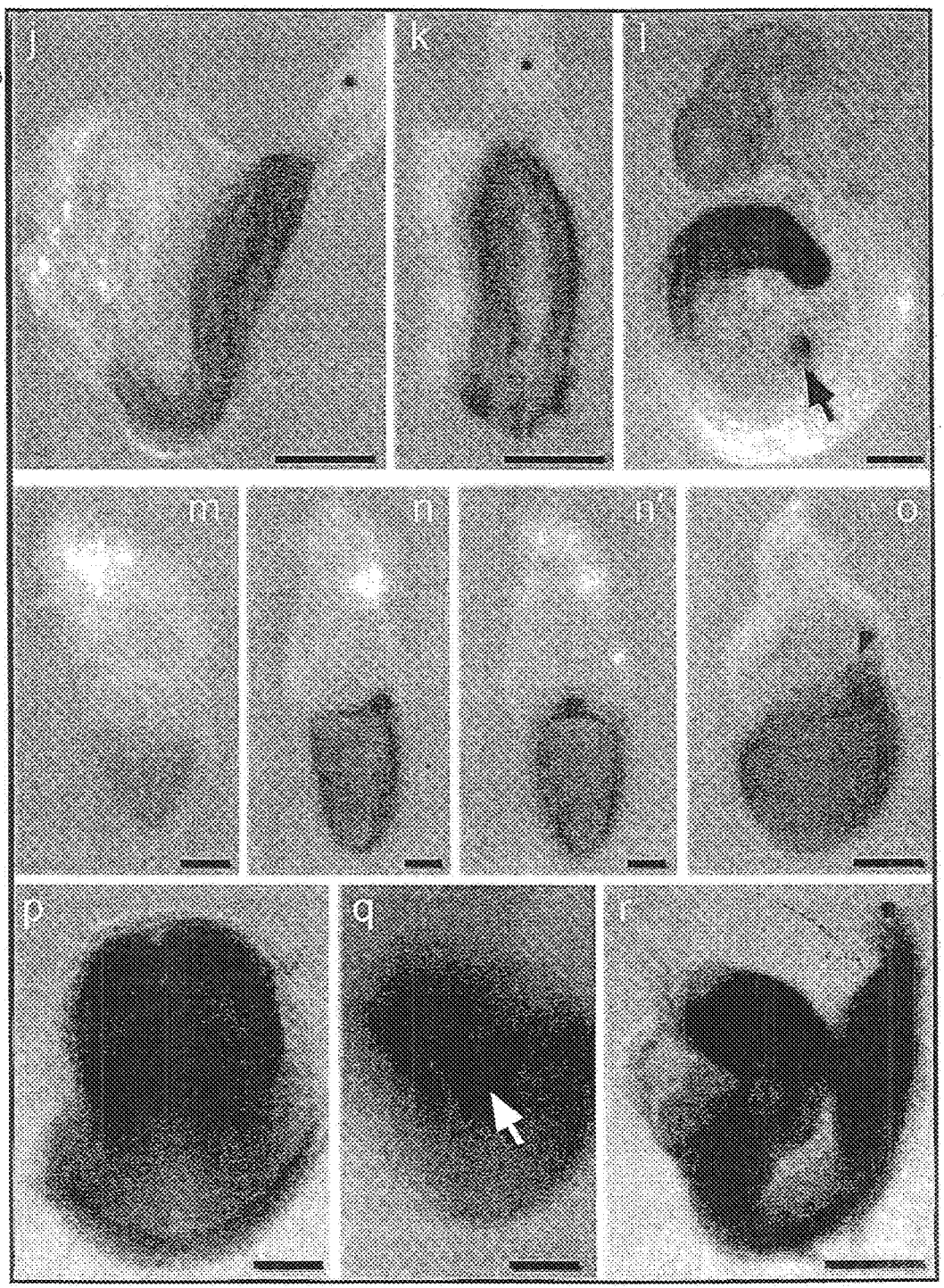

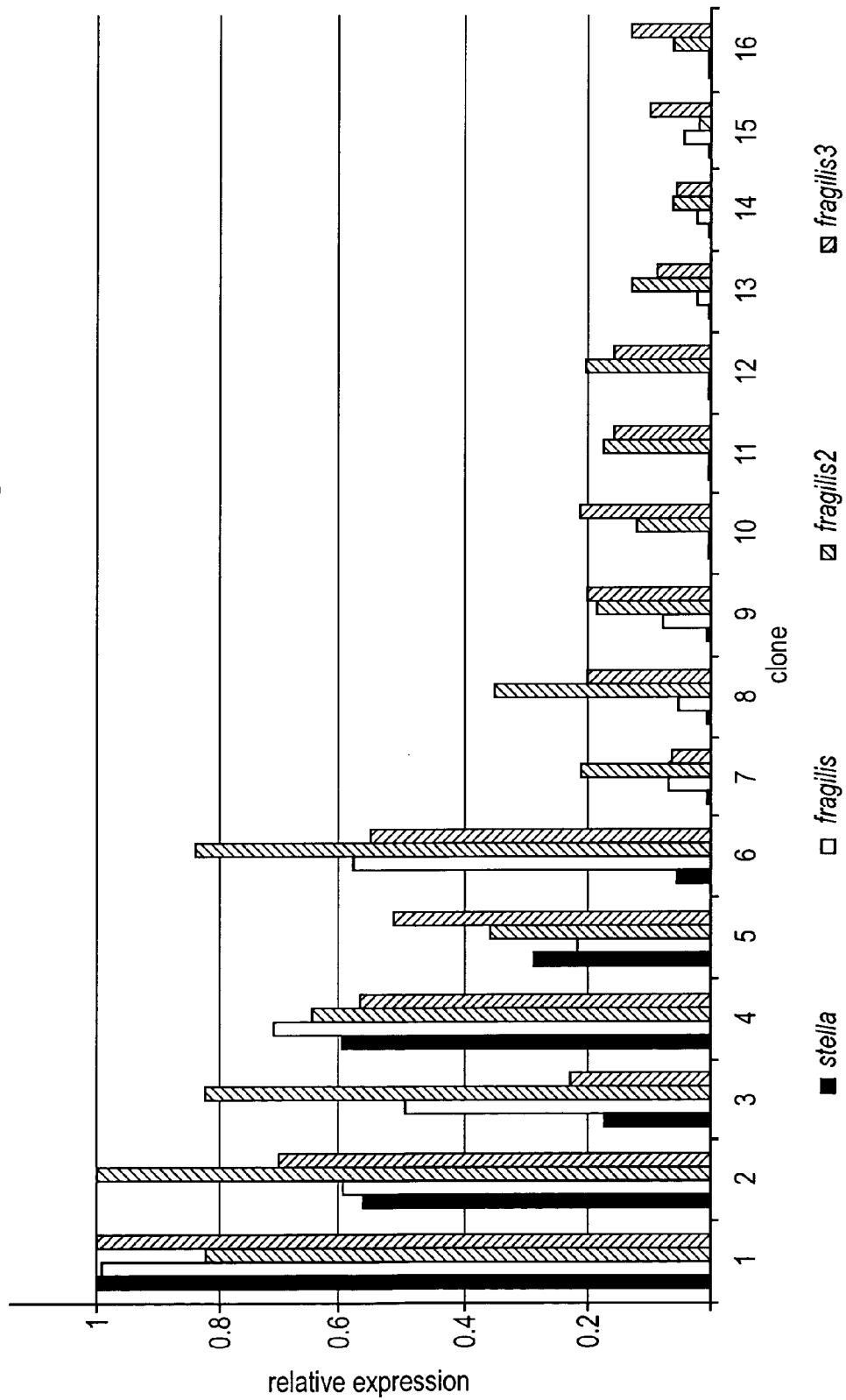

FIGS. 15A-L
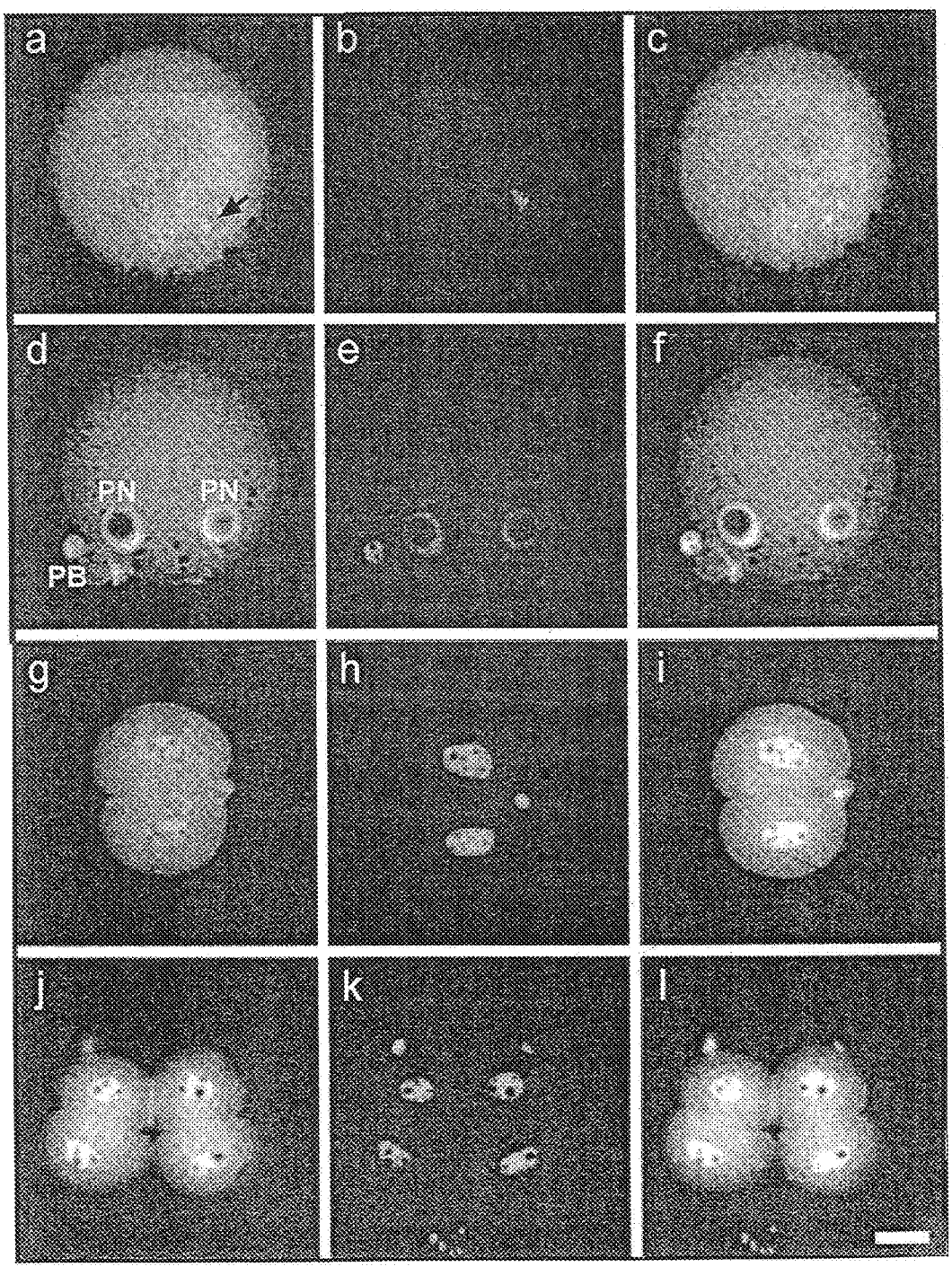

FIG. 17A
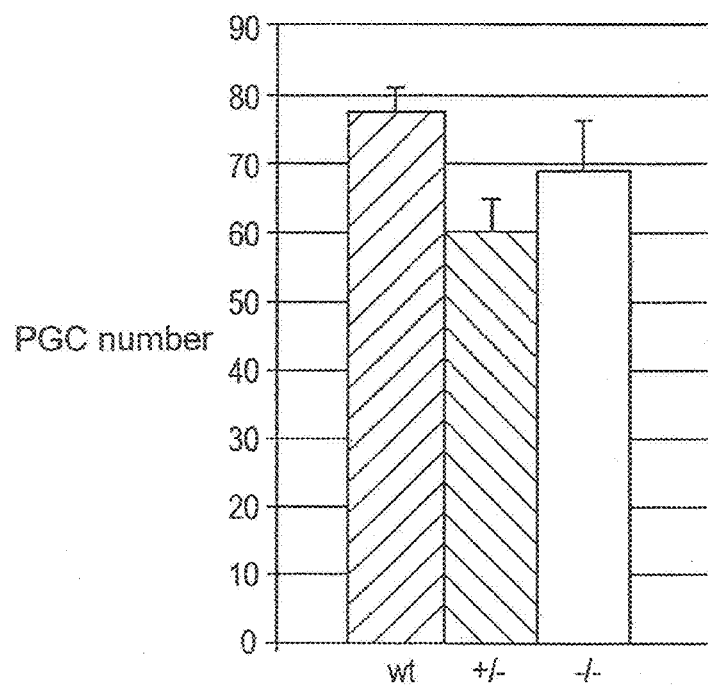
FIGS. 17B-G
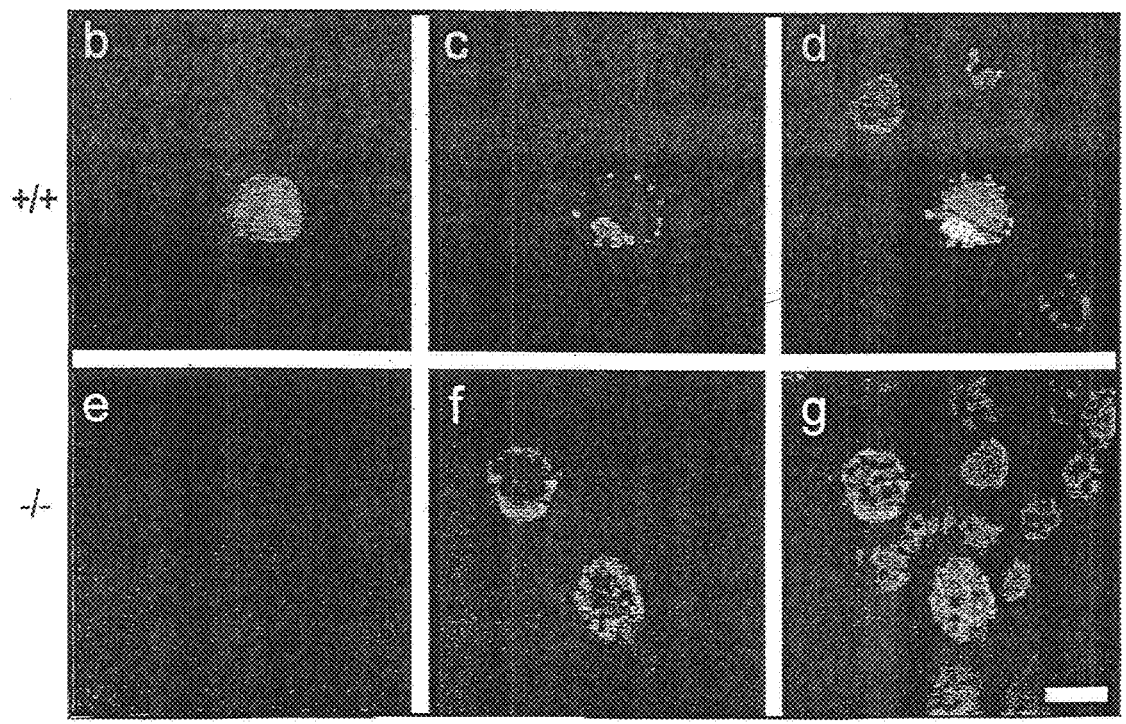

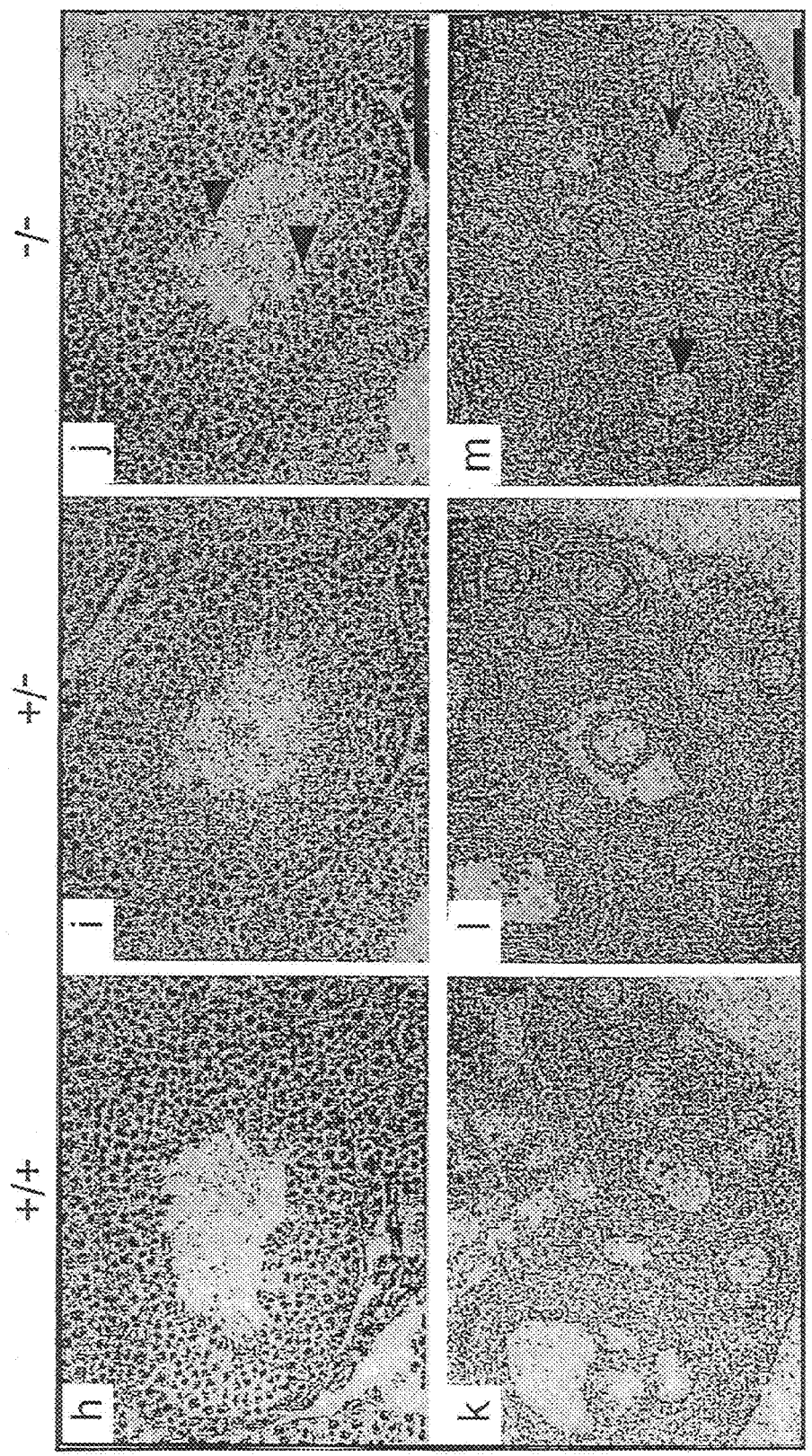
FIGS. 17H-M

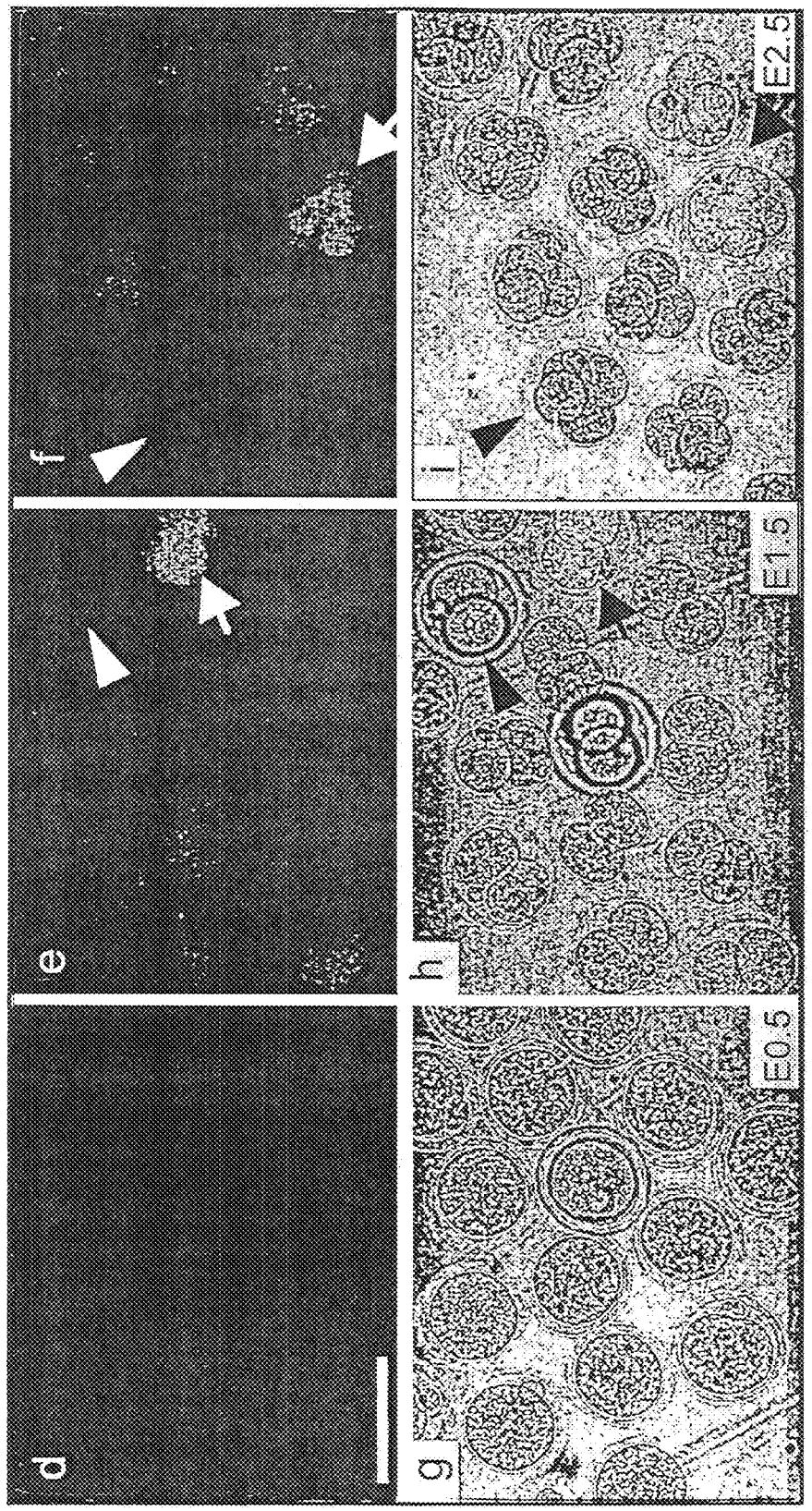
FIGS. 18D-I

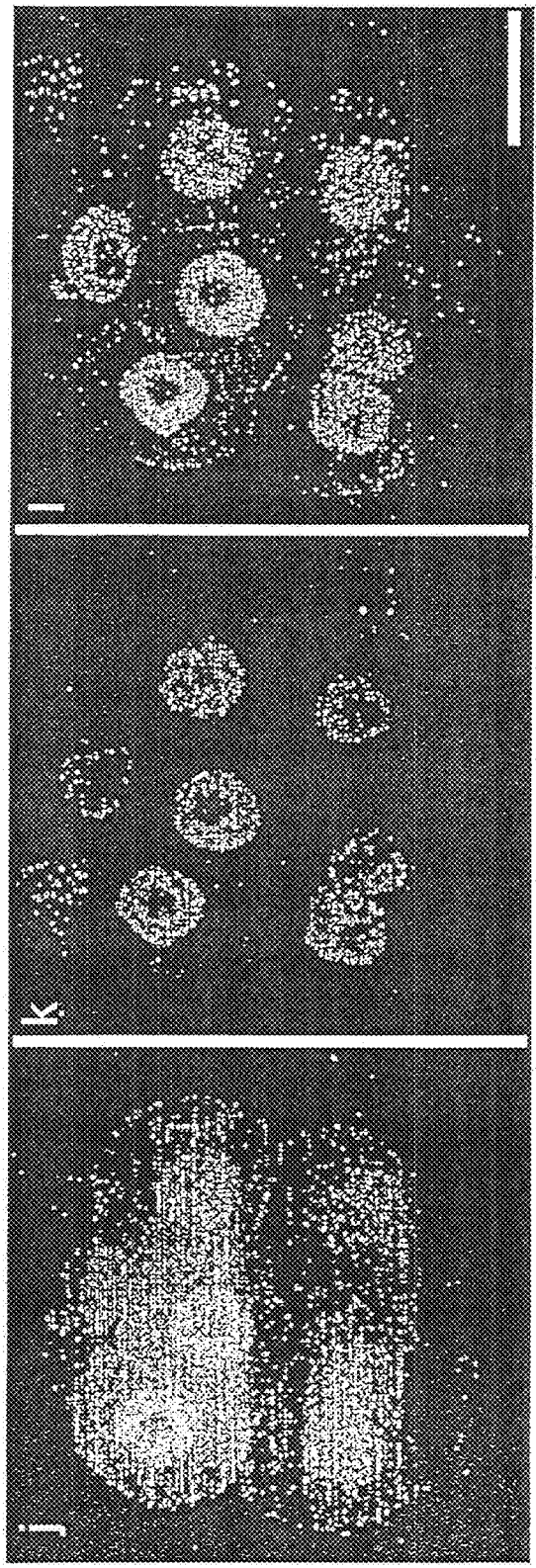
FIGS. 18J-L

ANTIBODIES TO THE EXTRACELLULAR DOMAIN OF HUMAN *FRAGILIS* POLYPEPTIDE AND METHODS OF MAKING SAID ANTIBODIES

FIELD

The present invention relates to the fields of development, molecular biology and genetics. More particularly, the invention relates to genes which are expressed exclusively in the earliest populations of primordial germ cells (PGCs) and the use of such genes and the products thereof in identification of pluripotent and multipotent cells such as PGCs, pluripotent embryonic stem cells (ES) and pluripotent embryonic germ cells (EG), in cell populations. They are also markers for a change in the state of cells from being non pluripotent to becoming pluripotent, and in being able to confer this state on a non pluripotent cell.

INTRODUCTION

Post fertilisation, the early mammalian embryo undergoes four rounds of cleavage to form a morula of 16 cells. These cells, following further rounds of division, develop into a blastocyst in which the cells can be divided into two distinct regions; the inner cell mass, which will form the embryo, and the trophectoderm, which will form extra-embryonic tissue, such as the placenta.

The cells that form part of the embryo up until the formation of the blastocyst are totipotent; in other words, each of the cells has the ability to give rise to a complete individual embryo, and to all the extra-embryonic tissues required for its development. After blastocyst formation, the cells of the inner cell mass are no longer totipotent, but are pluripotent, in that they can give rise to a range of different tissues. A known marker for such cells is the expression of the enzyme alkaline phosphatase and Oct4.

Primordial germ cells (PGCs) are pluripotent cells that have the ability to differentiate into all three primary germ layers. In mammals, the PGCs migrate from the base of the allantois, through the hindgut epithelium and dorsal mesentery, to colonise the gonadal anlague. The PGC-derived cells have a characteristically low cytoplasm/nucleus ratio, usually with prominent nucleoli. PGCs may be isolated from the embryos by removing the genital ridge of the embryo, dissociating the PGCs from the gonadal anlague, and collecting the PGCs. The earliest PGC population is reported to consist of a cluster of some 45 (forty-five) alkaline phosphatase positive cells, found at the base of the emerging allantois, 7.25 days post-fertilisation (Ginsburg et al., (1990) Development 110: 521-528).

PGCs have many applications in modern biotechnology and molecular biology. They are useful in the production of transgenic animals, where embryonic germ (EG) cells derived from PGCs may be used in much the same manner as embryonic stem (ES) cells (Labosky et al., (1994) Development 120:3197-3204). Moreover, they are useful in the study of foetal development and the provision of pluripotent stem cells for tissue regeneration in the therapy of degenerative diseases and repopulation of damaged tissue following trauma. Above all, PGCs while having some specialised properties, retain an underlying pluripotency, which is lost from the neighbouring cells that surround the founder population of PGCs that acquire a somatic cell fate. PGCs and the surrounding somatic cells share a common ancestry. However, the founder PGCs are few in number and difficult to isolate from embryonic tissue and the surrounding somatic cells, which complicates their study and the development of techniques which make use thereof.

Little is known in the art about the expression of genes in the founder population of PGCs and the relationship between PGC-specific gene expression and the retention of pluripotency in these cells. Certain markers for PGCs are known— for example, the expression of tissue non-specific alkaline phosphatase (SNAP) has been used as a marker for early PGCs (Ginsburg et al., (1990) Development 110:521-528). Oct4 is known to be expressed in PGCs, but not somatic cells (Yoem et al., (1996) Development 122:881-894). Other markers, such as BMP4, are known to be expressed primarily in somatic tissues (Lawson et al., (1999) Genes & Dev. 13:424-436). However, none of these genes is specific for PGCs, since they are also expressed in other tissue types. There is therefore a need in the art for the identification of genes which may be used as markers for PGCs and which may provide an insight into the biology of germ cell development and the nature of the pluripotent state.

Our unpublished International Patent Application Number PCT/GB02/00215, the contents of which are hereby incorporated by reference, discloses sequences and uses of two rodent genes, *Stella* and *Fragilis*. That document shows that *Stella* and *Fragilis* are expressed by PGCs and other pluripotent cells. The sequences of mouse *Stella* and *Fragilis* are also set out here as SEQ ID NO: 2 and SEQ ID NO: 1 respectively.

SUMMARY

We now disclose human sequences of *Stella* and *Fragilis*, as well as sequences of novel genes *Fragilis* 9-27, *Fragilis* 2, *Fragilis* 3, *Fragilis* 4, *Fragilis* 5 and *Fragilis* 6 comprising members of the *Fragilis* family of genes. We also disclose sequences of human *Fragilis* homologues, Ifitm 1, Ifitm 2, Ifitm 3 and Human ENSG142056. The genes and polypeptides described here, including associated products such as antibodies, are useful in a number of ways, for example, for diagnosis, treatment and/or prevention of diseases such as cancer.

According to a first aspect of the present invention, we provide a polypeptide comprising a human *Stella* amino acid sequence, preferably a sequence as shown in SEQ ID NO: 4, or a fragment, homologue, variant or derivative thereof.

There is provided, according to a second aspect of the present invention, a polypeptide comprising a human *Fragilis* amino acid sequence, preferably a sequence as shown in SEQ ID NO: 6, or a fragment, homologue, variant or derivative thereof.

We provide, according to a third aspect of the present invention, a polypeptide comprising an amino acid sequence selected from the group consisting of: *Fragilis* 9-27 (preferably comprising a sequence as shown in SEQ ID NO: 8), *Fragilis* 2 (preferably comprising a sequence as shown in SEQ ID NO: 10), *Fragilis* 3 (preferably comprising a sequence as shown in SEQ ID NO: 12), *Fragilis* 4 (preferably comprising a sequence as shown in SEQ ID NO: 14), *Fragilis* 5 (preferably comprising a sequence as shown in SEQ ID NO: 16) and *Fragilis* 6 (preferably comprising a sequence as shown in SEQ ID NO: 18), or a fragment, homologue, variant or derivative thereof.

As a fourth aspect of the present invention, there is provided a polypeptide consisting essentially of a sequence selected from the group consisting of: (a) the sequence of human *Stella* shown in SEQ ID NO: 4; (b) the sequence of human *Fragilis* shown in SEQ ID NO: 6; (c) the sequence of human *Fragilis* 9-27 shown in SEQ ID NO: 8; (d) the sequence of mouse *Fragilis* 2 shown in SEQ ID NO: 10; (e)

the sequence of mouse *Fragilis* 3 shown in SEQ ID NO: 12; (f) the sequence of mouse *Fragilis* 4 shown in SEQ ID NO: 14; (g) the sequence of mouse *Fragilis* 5 shown in SEQ ID NO: 16; and (h) the sequence of mouse *Fragilis* 6 shown in SEQ ID NO: 18.

We provide, according to a fifth aspect of the present invention, a polypeptide which has at least 50%, 60%, 70%, 80%, 90% or 95% homology to a polypeptide according to any of the preceding aspects.

The present invention, in a sixth aspect, provides a polypeptide comprising a sequence of 15 or fewer contiguous amino acids, preferably a sequence of fewer than 10 contiguous amino acids, of a nucleic acid according to any of the preceding aspects.

In a seventh aspect of the present invention, there is provided a nucleic acid encoding a polypeptide according to any preceding aspect.

According to an eighth aspect of the present invention, we provide a nucleic acid sequence comprising a human *Stella* nucleic acid sequence, preferably a sequence as shown in SEQ ID NO: 3, or a fragment, homologue, variant or derivative thereof.

We provide, according to a ninth aspect of the invention, a nucleic acid sequence comprising a human *Fragilis* nucleic acid sequence, preferably a sequence as shown in SEQ ID NO: 5, or a fragment, homologue, variant or derivative thereof.

There is provided, in accordance with a tenth aspect of the present invention, a nucleic acid sequence comprising an *Fragilis* nucleic acid sequence acid sequence selected from the group consisting of: *Fragilis* 9-27 (preferably a sequence as shown in SEQ ID NO: 7), *Fragilis* 2 (preferably a sequence as shown in SEQ ID NO: 9), *Fragilis* 3 (preferably a sequence as shown in SEQ ID NO: 11), *Fragilis* 4 (preferably a sequence as shown in SEQ ID NO: 13), *Fragilis* 5 (preferably a sequence as shown in SEQ ID NO: 15) and *Fragilis* 6 (preferably a sequence as shown in SEQ ID NO: 17), or a fragment, homologue, variant or derivative thereof.

As an eleventh aspect of the invention, we provide a nucleic acid sequence consisting essentially of a sequence selected from the group consisting of: (a) the sequence of human *Stella* shown in SEQ ID NO: 3; (b) the sequence of human *Fragilis* shown in SEQ ID NO: 5; (c) the sequence of human *Fragilis* 9-27 shown in SEQ ID NO: 7; (d) the sequence of mouse *Fragilis* 2 shown in SEQ ID NO: 9; (e) the sequence of mouse *Fragilis* 3 shown in SEQ ID NO: 11; (f) the sequence of mouse *Fragilis* 4 shown in SEQ ID NO: 13; (g) the sequence of mouse *Fragilis* 5 shown in SEQ ID NO: 15; and (h) the sequence of mouse *Fragilis* 6 shown in SEQ ID NO: 17.

We provide, according to a twelfth aspect of the invention, there is provided a nucleic acid sequence which has at least 50%, 60%, 70%, 80%, 90% or 95% homology to a nucleic acid sequence as disclosed.

According to a thirteenth aspect of the present invention, we provide a nucleic acid comprising a sequence of 25 or fewer contiguous nucleotides, preferably a sequence of 15 contiguous nucleotides, of a nucleic acid as disclosed.

There is provided, according to a fourteenth aspect of the present invention, a complement of a nucleic acid sequence as disclosed.

We provide, according to a fifteenth aspect of the present invention, a nucleic acid comprising a nucleic acid sequence as disclosed, together with one or more nucleotide substitutions, in which the one or more substitutions do not alter the coding specificity of said nucleic acid as a result of the degeneracy of the genetic code.

According to a sixteenth aspect of the present invention, we provide a vector comprising such a nucleic acid sequence.

According to a seventeenth aspect of the present invention, we provide a host cell comprising a nucleic acid sequence as disclosed.

There is provided, according to a eighteenth aspect of the present invention, a method of producing a polypeptide as disclosed, the method comprising providing a nucleic acid as disclosed, a vector as disclosed, or a host cell as disclosed, and enabling the expression of a nucleic acid encoding the polypeptide.

We provide, according to a nineteenth aspect of the invention, a method for identifying a pluripotent cell, comprising detecting such a polypeptide, or such a nucleic acid in the cell.

Preferably, the method comprises the steps of amplifying nucleic acids from a putative pluripotent cell using 5' and 3' primers specific for *Stella* and/or *Fragilis*, and detecting amplified nucleic acid thus produced. Preferably, the nucleic acid sequence is detected by in situ hybridisation. Preferably, the nucleic acid sequence is detected by detecting a protein product encoded by the nucleic acid. Preferably, the polypeptide is detected by immunostaining.

There is provided, according to a twentieth aspect of the present invention, an antibody specific for a polypeptide as disclosed. Preferably, the antibody is capable of specifically binding to an extracellular domain of *Fragilis*.

We provide, according to a twenty-first aspect of the present invention, use of such an antibody for the identification and/or isolation of a pluripotent cell.

As a twenty-second aspect of the present invention, there is provided pluripotent cell identified by a method as disclosed.

We provide, according to a twenty-third aspect of the present invention, a method of treatment or prophylaxis of a disease in an individual, the method comprising modulating the expression and/or the activity of *Stella* and/or *Fragilis* in a cell of the individual.

Preferably, the method comprises up-regulating the expression and/or the activity of *Stella* and/or *Fragilis*.

The present invention, in a twenty-fourth aspect, provides a *Stella* or *Fragilis* polypeptide or nucleic acid, or an antibody against *Stella* or *Fragilis*, for use in a method of treatment or prophylaxis of a disease in an individual.

In a twenty-fifth aspect of the present invention, there is provided use of a *Stella* or *Fragilis* polypeptide or nucleic acid, or an antibody against *Stella* or *Fragilis*, for the preparation of a pharmaceutical composition for the treatment of a disease.

According to an twenty-sixth aspect of the present invention, we provide a method of diagnosis of a disease, the method comprising detecting a modulation of expression and/or activity of *Stella* and/or *Fragilis* in a cell of an individual.

In preferred embodiments, the disease is selected from the group consisting of: testis tumor, colon tumor, stomach, germ cell tumors, choriocarcinoma, lung, large cell carcinoma, uterus, and leiomyosarcoma. *Stella* is therefore suitable for treatment or diagnosis of any disease of or associated with such tissues, in particular, cancer or tumours of such tissues.

We provide, according to a twenty-seventh aspect of the invention, a method of identifying a molecule capable of binding to *Stella* or *Fragilis*, the method comprising the steps of: (a) providing a *Stella* or *Fragilis* polypeptide; (b) contacting the *Stella* or *Fragilis* polypeptide with a candidate molecule; and (c) detecting binding between the candidate molecule and the *Stella* or *Fragilis* polypeptide, as the case may be.

There is provided, according to a twenty-eighth aspect of the present invention, a method of identifying an agonist or antagonist of Stella or Fragilis, the method comprising the steps of: (a) providing a Stella or Fragilis polypeptide; (b) contacting the Stella or Fragilis polypeptide with a candidate molecule; and (c) detecting modulation of an activity of the Stella or Fragilis polypeptide.

Preferably, the polypeptide is contacted with a plurality of candidate molecules, preferably in the form of a library.

We provide, according to a twenty-ninth aspect of the present invention, use of an antagonist of Stella or Fragilis, preferably as identified by a method according to any of the previous aspects, in a method of treatment or prophylaxis of a disease in an individual.

BRIEF DESCRIPTION OF THE FIGURES

FIG. 1: Nucleotide and deduced amino acid sequence of mouse Fragilis (SEQ ID NO: 1). Predicted positions of the two transmembrane domains (TM I and TM II) are underlined and indicated by bold letters. The poly(A) signal is underlined.

FIG. 2: Nucleotide and deduced amino acid sequence of mouse Stella (SEQ ID NO: 2). Three nuclear localization signals are underlined. A potential nuclear export signal is underlined twice, and the hydrophobic residues are indicated in bold. Helical structures in a motif with similarity to SAP domain (a.a.28 to a.a.63) are underlined in red, and the conserved residues are indicated by blue. A splicing factor-like motif is underlined and the conserved residues are indicated in green. Poly(A) signals are also underlined.

FIG. 3: Expression of mouse Fragilis in embryonic stem (ES) cells. ES cells are fixed in 4% paraformaldehyde in PBS for 10 min. at room temperature and processed for immunohistochemistry as described by Saitou et al., (1998). J Cell Biol 141, 397-408, (1998). Fragilis expression is similarly detected in E6.5 proximal epiblast cells, which are germ cell competent cells, and in newly specified germ cells. The expression declines after E8.5 following completion of the specification of germ cells fate.

FIGS. 8a and 8b. Expression of mouse Fragilis and mouse Stella in single cells detected by PCR analysis of single cell cDNAs. Numbers marked by symbol* in 8b are the PGCs. Note that there are more single cells showing expression of Fragilis compared to those showing expression of Stella. Only cells with the highest levels of Fragilis expression were found to express Stella and acquire the germ cell fate. Cells that express Stella were found not to show expression of Hoxb1. Cells that express lower levels of Fragilis and no Stella become somatic cells and showed expression of Hoxb1. The founder population of PGCs also show high levels of Tnap. Both the founder PGCs and the somatic cells show expression of Oct4, T(Brachyury), and Fgf8.

FIG. 10. Protein alignment of the Fragilis family and their homologues in human, cow and rat. Green bars indicate the location of the two predicted transmembrane domains, of which the first as well as the inter-domain stretch appear to be highly conserved throughout the four mammalian species. Identical amino acids are highlighted in dark grey, similar amino acids in light grey. The alignment was done using Clustl W.

FIG. 11. Expression analysis of fragilis (a-f), fragilis2 (g-l) and fragilis 3 (m-r) by whole mount in situ hybridisation. Pictures are taken as lateral view unless otherwise stated, with anterior to the left and posterior to the right. fragilis is expressed throughout the epiblast in E5.5 embryos (a) and in the region of germ cell specification at the base of the incipient and early allantoic bud at E7.5 (b, b' posterior view, c). At E8.5, signal is detected at the base and in the proximal third of the allantois as well as in the latero-anterior aspects of the brain (d superior view, e anterior view). At E9.5, fragilis appears expressed in a population of cells at the beginning of the invaginating hindgut (arrow in f), as well as in the pharyngeal arches (f). fragilis2 is detected throughout the epiblast at E5.5 (g). Expression seems thereafter downregulated but becomes again detectable in the posterior mesoderm and at the base of the incipient and growing allantoic bud in E7.0 and E7.5 embryos (h, i, i' posterior view). At E8.5, expression is seen in caudal mesoderm (j, k posterior view), while at E9.5 expression is seen in the tailbud, the mesoderm caudal to the $12^{th}$ somite and the lung primordia (arrow, l). fragilis3 is expressed throughout the epiblast at E6.5 (m) and around E7.5 additionally in the region of PGC specification (n, n' posterior view, o). At E8.5, fragilis2 expression is seen throughout the embryo, with exception of the developing heart, and appears intense in single cells (arrow in q posterior view) at the base and within the proximal region of the allantois (p posterior view, q, r). asterix: allantois; black arrowhead: allantoic bud; white arrowhead: developing heart; scale bars: 100 µm (a, b, g-i, m, n); 200 µm (c-e, o-q); 400 µm (f, j-l, r).

FIG. 17. Germ cell development in *stella* knockout mice. a, Numbers of PGCs in wild-type (wt, n=9), *stella*$^{+/-}$ (n=14) and *stella*$^{-/-}$ (n=7) embryos are not significantly different at E8.5 (0-8 somites). The results are presented as means ±SEM. b-g, Gonadal PGCs (E11.5) stained with anti-*stella* (b, e) and anti-SSEA1 (c, f) antibodies (d, g merge including Toto3 (blue) as DNA stain). The PGC-marker SSEA1[17] is coexpressed with *stella* in wild-type PGCs (b-d) and also detectable in *stella*$^{-/-}$ animals (e-g), showing that PGCs are present in knockout mice. Scale bar=10 µm. Sections of testes (h-j) and ovaries (k-m) of adult wild-type (h, k), *stella*$^{+/-}$ (i, l) and *stella*$^{-/-}$ (j, m) mice. Knockout males show normal development of sperm (arrowheads) and knockout females normal ovary morphology with follicles containing oocytes of different stages (arrows). Scale bars in j (for h-j), m (for k-m)=100 µm.

SEQUENCE LISTINGS

Figure 4:
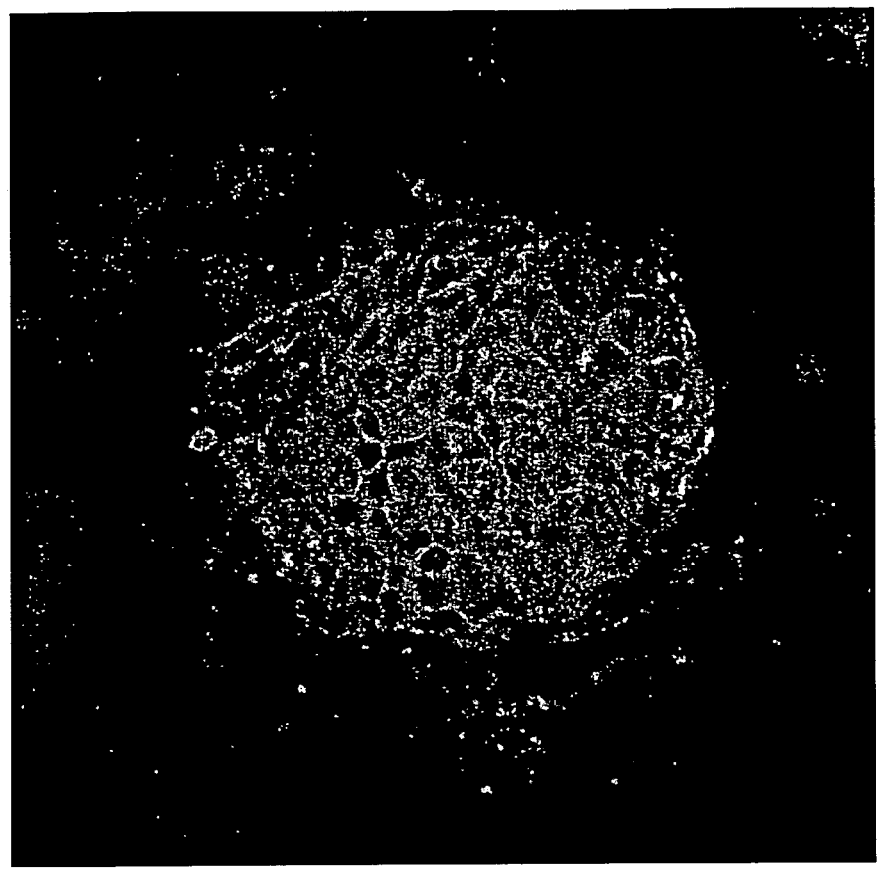
FIG. 4: Expression of mouse Stella in PGCs. PGCs from E12.5 genital ridges are fixed in 4% paraformaldehyde in PBS for 10 min. at room temperature and processed for immunohistochemistry as described by Saitou et al., (1998). J Cell Biol 141, 397-408, (1998). Stella is detected in PGCs from E 7.25-13.5, as well as in pluripotent ES cells and in EG cells. Stella is also detected in the totipotent oocyte, zygote and in the totipotent and pluripotent blastomeres during pre-implantation development and in developing gametes. When EG cells are derived from PGCs (Labosky et al., (1994) Development 120:3197-3204). Fragilis expression is again detected in the pluripotent EG cells as it is in ES cells. Therefore, Fragilis and Stella are also markers for the pluripotent stem cells.

SEQ ID NO: 1 shows the nucleic acid sequence of mouse *Fragilis* while SEQ ID NO: 2 shows the nucleic acid sequence of mouse *Stella*.

SEQ ID NO: 3 shows the nucleic acid sequence of human *Stella*; SEQ ID NO: 4 shows the amino acid sequence of human *Stella*; SEQ ID NO: 5 shows the nucleic acid sequence of human *Fragilis* 1-8D; SEQ ID NO: 6 shows the amino acid sequence of human *Fragilis* 1-8D; SEQ ID NO: 7 shows the nucleic acid sequence of human *Fragilis* 9-27/Leu13; SEQ ID NO: 8 shows the amino acid sequence of human *Fragilis* 9-27/ Leu13; SEQ ID NO: 9 shows the nucleic acid sequence of mouse *Fragilis* 2; SEQ ID NO: 10 shows the amino acid sequence of mouse *Fragilis* 2; SEQ ID NO: 11 shows the nucleic acid sequence of mouse *Fragilis* 3; SEQ ID NO: 12 shows the amino acid sequence of mouse *Fragilis* 3; SEQ ID NO: 13 shows the nucleic acid sequence of mouse *Fragilis* 4; SEQ ID NO: 14 shows the amino acid sequence of mouse *Fragilis* 4; SEQ ID NO: 15 shows the nucleic acid sequence of mouse *Fragilis* 5; SEQ ID NO: 16 shows the amino acid sequence of mouse *Fragilis* 5; SEQ ID NO: 17 shows the nucleic acid sequence of mouse *Fragilis* 6; SEQ ID NO: 18 shows the amino acid sequence of mouse *Fragilis* 6.

DETAILED DESCRIPTION

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

*Stella* and *Fragilis*

The disclosure provides generally for *Fragilis* and *Stella* nucleic acids, polypeptides, as well as fragments, homologues, variants and derivatives thereof. In particular, we provide for human *Stella* and *Fragilis* nucleic acids, polypeptides, as well as fragments, etc.

The names "*Fragilis*" and "GCR1" should be understood as synonymous with each other, and likewise, "*Stella*" and "GCR2" should be considered synonyms. In general, unless the context requires otherwise, the term "*Fragilis*" should be taken to refer to any member of the *Fragilis* family, including *Fragilis* itself, *Fragilis* 9-27, *Fragilis* 2, *Fragilis* 3, *Fragilis* 4, *Fragilis* 5 and *Fragilis* 6. In addition, Ifitm1, Ifitm2, Ifitm3 and ENSG142056 are preferably included within the term "*Fragilis*". Preferably, the *Stella* and *Fragilis* sequences disclosed are derived from higher animals, for example primates, in particular, *Homo sapiens* (man).

In preferred embodiments, therefore, *Fragilis* should be taken to refer to the human nucleic acid sequence shown in SEQ ID NO: 5, or the human amino acid sequence shown in SEQ ID NO: 6, as the context requires. Furthermore, in preferred embodiments, *Stella* should be taken to refer to the human nucleic acid sequence shown in SEQ ID NO: 3, or the human amino acid sequence shown in SEQ ID NO: 4, as the context requires.

Human *Stella* and *Fragilis* are related by homology and function to the mouse *Stella* and *Fragilis* sequences disclosed in PCT/GB02/00215, and also set out as SEQ ID NO: 1 and SEQ ID NO: 2 in this document. *Fragilis* and *Stella* are PGC-specific transcripts. *Fragilis* is upregulated during the process of lineage commitment of PGCs, while *Stella* is upregulated after *Fragilis*, and marks commitment to the PGC fate.

Human *Fragilis* (also known as Germ cell restricted-1, GCR1), encodes a 132 amino acid protein with a predicted molecular weight of 14.5 kD. A best fit model of the EMBL program PredictProtein predicts two transmembrane domains, both N and C terminus ends being located outside. A BLASTP search revealed that *Fragilis* is a novel member of the interferon-inducible protein family. One prototype member, human 9-27 (identical to Leu-13 antigen), is inducible by interferon in leukocytes and endothelial cells, and is located at the cell surface as a component of a multimeric complex involved in the transduction of antiproliferative and homotypic adhesion signals (Deblandre, 1995). The BLASTN search revealed that the *Fragilis* sequence was found in ESTs derived from many different tissues both from embryos and adults, indicating that *Fragilis* may play a common role in different developmental and cell biological contexts, including cancer; this is described in further detail below. Database searches reveal a sequence match with the rat interferon-inducible protein (sp:INIB RAT, pir:JC1241) with unknown function. The *Fragilis* sequence appears several times in our screen, indicating high level expression in PGCs.

The second gene, human *Stella*, (*Stella*) encodes a 159 amino acid protein, of 17.5 kD. It has no sequence homology with any known protein, apart from murine and rodent *Stella*, contains several nuclear localisation consensus sequences and is highly basic pI, indicating a possible affinity to DNA. Furthermore a potential nuclear export signal is identified, indicating that *Stella* may shuttle between the nucleus and the cytoplasm. BLASTN analysis reveals that the *Stella* sequence is found only in the preimplantation embryo and germ line (newborn ovary, female 12.5 mesonephros and gonad etc.) ESTs indicating its predominant expression in totipotent and pluripotent cells. Interestingly, we found that *Stella* contains in its N terminus a modular domain which has some sequence similarity with the SAP motif. This motif is a putative DNA-binding domain involved in chromosomal orgainisation. Furthermore, the SMART program reveals the presence of a splicing factor motif-like structure in its C-terminus, These findings indicate a possible involvement of *Stella* in chromosomal organisation and RNA processing.

Antibodies may be raised against the *Fragilis* and/or *Stella* polypeptides. In particular, antibodies may be raised against the extracellular domain of *Fragilis*, which is a transmembrane polypeptide.

Antibodies, polypeptides and nucleic acids disclosed here are useful for the identification of PGCs in cell populations. The methods and compositions described here therefore provide a means to isolate PGCs, useful for example for the study of germ tissue development and the generation of transgenic animals, and PGCs when isolated by a method described here.

Homologues of *Fragilis* and *Stella* may also be used to identify PGCs and other pluripotent cells, such as ES or EG cells.

Furthermore, the methods and compositions described here are useful for treating or preventing cancer, in view of the role of *Stella* and *Fragilis* in development and cell fate control.

Human *Stella* and *Fragilis*

The murine *Stella* and *Fragilis* genes are isolated by the methods shown in the Examples; these are disclosed in detail in our International Application PCT/GB02/00215. The murine *Fragilis* sequence isolated is shown as SEQ ID NO: 1, while the mouse *Stella* sequence is shown as SEQ ID NO: 2.

Human homologues of *Stella* and *Fragilis* are described in further detail in the following sections, and may (if necessary) be identified and cloned by standard techniques.

Human *Stella*

Human *Stella* Nucleic Acid Sequence

AGCAATTTGAGGCTCTGTCATCAGTTTCTGCTACGTTTCAAAGATCCTGG

AGAAGCCTAGTGTTGTGTCAAGACGCCGATGGACCCATCACAGTTTAATC

CAACCTACATCCCAGGGTCTCCACAAATGCTCACCGAAGAAAATTCGCGG

GACGATTCAGGGGCCTCTCAAATCTCCTCCGAGACGTTGATAAAGAACCT

TAGTAACTTGACTATCAACGCTAGTAGCGAATCTGTTTCCCCTCTATCGG

AAGCTTTACTGCGTCGAGAGTCTGTAGGAGCAGCAGTCCTCAGGGAAATC

GAAGATGAGTGGCTTTACAGCAGGAGAGGAGTAAGAACATTGCTGTCTGT

GCAGAGAGAAAAGATGGCAAGATTGAGATACATGTTACTCGGCGGAGTTC

GTACGCATGAAGAAGACCAACAAACAAGGAGCCTAAGGGAGTTAAGAAG

GAATCAAGACCATTCAAATGTCCCTGCAGTTTCTGCGTGTCTAATGGATG

GGATCCTTCTGAGAATGCTAGAATAGGGAATCAAGACACCAAGCCACTTC

AGCCATAAATCTTATTCTTGCACCTTTTTTTCTTGGTAGTAATTTTATAT

AGCAGGTTGAGAAAGCTACTCTATGCTAGTATAGACTATACACCAATAAT

TTTGATAATGAGTTCTAGGATGTATTTTTCTTGTATCTTTTTCTTCCTAC

TATGATACTAGTAATTCATAAGGGATCTGTGTAATCTGAATGTATTTGAA

TAAGTTTAGCTCTACTGTTTGATTTGACCCAAAGAAGCCAAGATGATATA

AGTATTCCCATGTGTCTTAGAAGCCCAAAGTCAGTGAGATGAAACCCAAC

ATCAAGAAATTGAAGCAAAGTTACTTATGGATAAAGAAAGCATTAGGTAG

TTGGGCTATAGCATAATTAGATTTTCTGGCTTTCAAAAATTTGGATTGCA

ATCACAGCAAACTTTGTTATTTTTACAGTTTTCAGTACAAAAGTGTTTAT

ATAGAAACAATAAAGTTGACATTTGAGTACCTTTTAAAAA

Human *Stella* Amino Acid Sequence

MDPSQFNPTYIPGSPQMLTEENSRDDSGASQISSETLIKNLSNLTINASS

ESVSPLSEALLRRESVGAAVLREIEDEWLYSRRGVRTLLSVQREKMARLR

YMLLGGVRTHERRPTNKEPKGVKKESRPFKCPCSFCVSNGWDPSENARIG

NQDTKPLQP

Human *Stella* Expression

Human *Stella* is expressed in a number of tissues, including: testis, colon, lung, uterus, and germinal center B cell.

Human *Stella* Diseases

Diseases associated with abnormal expression of human *Stella* include: testis tumor, colon tumor, stomach, germ cell tumors, choriocarcinoma, lung, large cell carcinoma, uterus, and leiomyosarcoma.

Human *Stella* is therefore suitable for treatment or diagnosis of any disease of or associated with such tissues, in particular, cancer or tumours of such tissues.

Human *Fragilis*

Human *Fragilis* is also referred to as *Fragilis* 1-8D.

Human *Fragilis* Nucleic Acid Sequence

TCCCGGTAACCCGATCACCGCTGGTCACCATGAACCACATTGTGCAAACC

TTCTCTCCTGTCAACAGCGGCCAGCCTCCCAACTACGAGATGCTCAAGGA

GGAGCAGGAAGTGGCTATGCTGGGGGTGCCCCACAACCCTGCTCCCCCGA

TGTCCACCGTGATCCACATCCGCAGCGAGACCTCCGTGCCTGACCATGTG

GTCTGGTCCCTGTTCAACACCCTCTTCATGAACACCTGCTGCCTGGGCTT

CATAGCATTCGCGTACTCGGTGAAGTCTAGGGACAGGAAGATGGTTGGCG

ACGTGACCGGGGCCCAGGCCTATGCCTCCACCGCCAAGTGCCTGAACATC

TGGGCCCTGATTTTGGGCATCTTCATGACCATTCTGCTCATCATCATCCC

AGTGTTGGTCGTCCAGGCCCAGCGATAGATCAGGAGGCATCATTGAGGCC

AGGAGCTCTGCCCGTGACCTGTATCCCACGTACTCTATCTTCCATTCCTC

GCCCTGCCCCCAGAGGCCAGGAGCTCTGCCCTTGACCTGTATTCCACTTA

CTCCACCTCCCATTCCTCGCCCTGTCCCCACAGCCGAGTCCTGCATCAGC

CCTTTATCCTCAGACGCTTTTCTACAATGGCATTCAATAAAGTGTATATG

TTT

Human *Fragilis* Amino Acid Sequence

MNHIVQTFSPVNSGQPPNYEMLKEEQEVAMLGVPHNPAPPMSTVTHIRSE

TSVPDHVVWSLFNTLFMNTCCLGFIAFAYSVKSRDRKMVGDVTGAQAYAS

TAKCLNIWALILGIFMTILLIIIPVLVVQAQR

Human *Fragilis* Genomic Location Human *Fragilis* is located on chromosome 11, at chromosomal location 11p15.5.

Human *Fragilis* Diseases

Human *Fragilis* 1-8D is expressed in a number of tissues, including: stomach; adenocarcinoma; adenocarcinoma cell line; adipose; adrenal cortico adenoma for cushing's syndrome; adrenal gland; aorta; ascites; bone; bone marrow; brain; breast; breast_normal; cartilage; cervical carcinoma cell line; colon; colon_ins; colonic mucosa from 3 patients with crohn's disease; cord blood; corresponding non cancerous liver tissue; embryonal carcinoma; embryonal carcinoma, cell line; endometrium, adenocarcinoma cell line; epithelioid carcinoma; epithelioid carcinoma cell line; eye; foreskin; four pooled poorly-differentiated adenocarcinomas; from acute myelogenous leukemia; from chronic myelogenous leukemia; gall bladder; head_neck; heart; hepatocellular carcinoma, cell line; human retina; human skeletal muscle; hypemephroma; hypemephroma, cell line; hypothalamus, cell line; insulinoma; iris; islets of langerhans; kidney; kidney_tumor; large cell carcinoma; large cell carcinoma, undifferentiated; leiomyosarcoma; leiomyosarcoma cell line; lens; leukocyte; liver, lung; lung focal fibrosis; lung- _normal; lung_tumor; lymph; marrow; metastatic chondrosarcoma; mixed (pool of 40 rnas); mucoepidermoid carcinoma; muscle; muscle (skeletal); neuroblastoma cells; normal epithelium; normal head/neck tissue; optic nerve; osteosarcoma, cell line; ovary; ovary (pool of 3); pancreas; papillary serous ovarian metastasis; parathyroid; pheochromocytoma; pituitary; placenta; placenta_normal; pool; pooled brain, lung, testis; pooled colon, kidney, stomach; pooled lung and spleen; pooled pancreas and spleen; primary b-cells from tonsils (cell line); primary lung epithelial cells; primitive neuroectoderm; prostate; prostate_normal; prostate_tumor; purified pancreatic islet; renal cell adenocarcinoma; rpe and choroid; serous papillary tumor; skin; spleen; squamous cell carcinoma, poorly differentiated (4 pooled tumors, including primary and metastatic); stomach; subchondral bone; testis; testis_normal; thyroid; tonsil; two pooled squamous cell carcinomas; uterus; uterus_tumor; whole embryo.

Human *Fragilis* is therefore suitable for treatment or diagnosis of any disease of or associated with such tissues, in particular, cancer or tumours of such tissues.

Human *Fragilis* 9-27/LEU13

A sequence related to human *Fragilis*, i.e., human *Fragilis* 9-27 (also known as Leu13) is also identified. This sequence comprises a member of the *Fragilis* family of proteins.

Human *Fragilis* 9-27/Leu13 Nucleic Acid Sequence

```
tgagaaactgaaacgacaggggaaaggAggtctcActgagcaccgtccca
gcatccggacaccacagcggccttcgctccacgcagaaaaccacacttc
tcaaaccttcActcaacacttccttccccaaagccagaagatgcacaagg
aggaacatgaggtggctgtgctgggggcaccccccagcaccatccttcca
aggtccaccgtgatcaacatccacagcgagacctccgtgcccgaccatgt
cgtctggtccctgttcaacaccctcttcttgaactggtgctgtctgggct
tcatagcattcgcctactccgtgaagtctagggacaggaagatggttggc
gacgtgaccggggcccaggcctatgcctccaccgccaagtgcctgaacat
ctgggccctgattctgggcatcctcatgaccattggattcatcctgtcac
tggtattcggctctgtgacagtctaccatattatgttacagataatacag
gaaaaacggggttactagtagccgcccatagcctgcaacctttgcactcc
actgtgcaatgctggccctgcacgctggggctgttgccctgccccttg
gtcctgcccctagatacagcagtttatacccacacacctgtctacagtgt
cattcaataaagtgcacgtgcttgtga
```

Human *Fragilis* 9-27/Leu13 Amino Acid Sequence

```
MHKEEHEVAVLGAPPSTILPRSTVINIHSETSVPDHVVWSLFNTLFLNWC
CLGFIAFAYSVKSRDRKMVGDVTGAQAYASTAKCLNIWALILGILMTIGF
ILSLVFGSVTVYHIMLQIIQEKRGY
```

Human *Fragilis* 9-27/Leu13 Genomic Location

Human *Fragilis* 9-27/Leu13 is located on chromosome 11.

Human *Fragilis* 9-27/Leu13 Diseases

Human *Fragilis* 9-27/Leu13 is expressed in a number of tissues, including: Stomach; adenocarcinoma; adenocarcinoma, cell line; adipose; adrenal cortico adenoma for cushing's syndrome; amnion normal; ascites; bone; bone marrow; brain; breast; cervical carcinoma cell line; chondrosarcoma; colon; colon ins; cord blood; ear; embryonal carcinoma; epid tumor; epithelioid carcinoma; eye; eye anterior segment; from acute myelogenous leukemia; from chronic myelogenous leukemia; germ cell; head neck; head normal; heart; human retina; hypothalamus, cell line; insulinoma; kidney; kidney tumor; large cell carcinoma; large cell carcinoma, undifferentiated; leiomios; leiomyosarcoma; leukocyte; liver; lung; lung normal; lymph; marrow; mixed (pool of 40 rnas); mucoepidermoid carcinoma; muscle; muscle (skeletal); nervous tumor; normal head/neck tissue; nose; optic nerve; osteoarthritic cartilage; ovary; pancreas; papillary serous ovarian metastasis; parathyroid; pheochromocytoma; pituitary; placenta; placenta normal; pool; pooled brain, lung, testis; pooled pancreas and spleen; primary b-cells from tonsils (cell line); primitive neuroectoderm; prostate; prostate normal; purified pancreatic islet; retinal pigment epithelium sheets; rpe and choroid; skin; spleen; stomach; testis, cell line; testis normal; tonsil; trabecular meshwork; uterus; uterus tumor; whole embryo.

Human *Fragilis* 9-27/Leu13 is therefore suitable for treatment or diagnosis of any disease of or associated with such tissues, in particular, cancer or tumours of such tissues.

Mouse *Fragilis* 2

Furthermore, we have identified several mouse sequences (namely, *Fragilis* 2, *Fragilis* 3, *Fragilis* 4, *Fragilis* 5 and *Fragilis* 6) which are related to *Fragilis* and comprise *Fragilis* family members.

Mouse *Fragilis* 2 Nucleic Acid Sequence

```
GCGGGTCTACAGAACCAGGATAGCAGCAGCCATGCTCCAGACGGGGCGAT
TGTTCCAGAGTCAGTACCATGAGCCACAATTCTCAAGCCTTCTTGTCCAC
CAATGCCGGGCTTCCTCCAAGCTATGAGACAATCAAAGAGGAGTACGGGG
TGACTGAGCTGGGGGAACCCAGCAACTCAGCTGTTGTGAGGACCACCGTG
ATCAACATGCCCAGAGAGGTGTCGGTGCCTGACCATGTGGTCTGGTCCCT
GTTCAATACACTCTTCTTCAACGCCTGCTGCCTGGGCTTCGTTGCCTATG
CCTACTCTGTGAAGTCTAGGGACAGGAAGATGGTGGGCGATGTGGTTGGA
GCGCAGGCCTACGCCTCCACTGCCAAGTGCCTGAATATCAGCTCCCTGAT
CTTCAGCATCCTTATGGTCATTATCTGCATCATTATTTTCTCTACCACCT
CTGTGGTAGTCTTTCAGTCTTTTGCACAAAGAACACCCCATTCTGGATTC
TAGCTGCCCTGTGCTCCACGGTCCACATCTGCCCCGCCCCTGCCCCGCCC
CCAGGCTCAAGCCTCGACCCTTTACCCTACGCGTATGCAAATGTTACCTT
CACCTATCTGTCCACAGTGGATTCAATAAAGTGCACGGGGTGGCAACTCT
G
```

Mouse *Fragilis* 2 Amino Acid Sequence

```
MSHNSQAFLSTNAGLPPSYETIKEEYGVTELGEPSNSAWRTTVINMPREV
SVPDHVVWSLFNTLFFNACCLGFVAYAYSVKSRDRKMVGDVVGAQAYAST
AKCLNISSLIFSILMVIICIIIFSTTSVVVFQSFAQRTPHSGF
```

Mouse *Fragilis* 2 Diseases

Mouse *Fragilis* 2 is expressed in a number of tissues, including: adult; branchial arches; colon; embryo; embryonal carcinoma; head; heart; hippocampus; liver; lymph; macrophage; mammary gland; mandible; muscle; pancreas; pool; pooled lung tumors; pooled mammary gland tumors; salivary gland; skin; small intestine; spleen; spontaneous tumor, metastatic to mammary. stem cell origin.; stomach; subfornical organ and postrema; t cell; testis; thymus; tumor, biopsy sample; tumor, gross tissue; tumor, metastatic to mammary; uterus; whole embryo.

Mouse *Fragilis* 2, as well as its human homologue, is therefore suitable for treatment or diagnosis of any disease of or associated with such tissues, in particular, cancer or tumours of such tissues.

Mouse *Fragilis* 3

Mouse *Fragilis* 3 Nucleic Acid Sequence

TGGAGAAAAGGCCACTGCGCAAAGGGCTCTGGACTTCTCAGCTTGTACCA

CCATTCTCATTCCTTCCTTATTCTCAACTCTTCCAGCCTCAAAAACCAAG

AGATGCCTAAGGATCAGCATGAGGTGGTTGTAATGGGGACACCCCACACC

TCAACTTCTTCGACAACCACCATAATCACCATGCCTGAGATCTCCAAGCC

TGATTATGTGGTCTGGTCTCTGTTCAATACACTCTTCATGAACTTCTGCT

GCCTGGGTTTCATAGCCTATGCCTACTCTGTGAAGTCTAGGGACAGGAAG

ATGGTGGGTGATATGACTGGGCCCAGGCCTTCGCCTCCACTGCCAGGTGC

CTGAACATCAGCTGCCTGATCCTCTCCGTGGTCATGGTCATCCTCTTCAT

CACTTTCTTTGCCACTAGAAGGTAGCCATCTTGTAGCATCTCACAGTAGA

TAACAGATTCTGGGGCCTTCCGGGCTTGCTATGTGTTCTATTGTCTATCG

CTGTCCCAAACCCTAGTCTTAGTCCTGACCATTTACCCCATACATATGCA

AATGTTACACTTGCATATCTGTTCATTCAATAAAGTGCA

Mouse *Fragilis* 3 Amino Acid Sequence

MPKDQHEVVVMGTPHTSTSSTTTIITMPEISKPDYVVWSLFNTLFMNFCC

LGFIAYAYSVKSRDRKMVGDMTGAQAFASTARCLNISCLILSVVMVILFI

TFFATRR

Mouse *Fragilis* 3 Genomic Location

Mouse *Fragilis* 3 is located on chromosome 16.

Mouse *Fragilis* 3 Diseases

Mouse *Fragilis* 3 is expressed in a number of tissues, including: adult; branchial round spermatids, pooled from multiple mice; testis.

Mouse *Fragilis* 3, as well as its human homologue, is therefore suitable for treatment or diagnosis of any disease of or associated with such tissues, in particular, cancer or tumours of such tissues.

Mouse *Fragilis* 4

Mouse *Fragilis* 4 Nucleic Acid Sequence

GATTCCTTCCTTATTCTCACTCTGCAGCTTCAAAAGCCGAGAGATGCCTA

AGGAGCAGCAAGAGGTGGTTGTACTGGGGTCACCCCACATCTCAACTTCT

GCGACAGCCACCACAATCAACATGCCTGAGATCTCCACGCCTGACCATGT

GGTCTGGTCCCTGTTCAATACACTCTTCATGAACTTCTGCTGCCTGGGCT

TCGTAGCCTATGCCTACTCCGTGAAGTCTAGGGACAGGAAGATGGTGGGT

GATACGACTGGGGCCCAGGCCTTCGCCTCCACCGCCAAGTGCCTGAACAT

CAGCTCCCTGTTCTTCACCATCCTCACGGCCATCGTCGTCATCGTTGTCT

GTGCCATTAGATGATGTGAGATGTCTTGCAACATCTCACAGTAGATAACA

GATTCTGGGGCCTCCCAGGCTTGCTATGTGTTTCCTTGTCTATCGCTGCC

CCAAACCCTAGACTTAGTCCTGACCATTTGCGCCATACATATGCAAATGT

GACACTCACAAATCTGTCCATGGTGGACTCAATAAAGTGCACGTGCTGTG

Mouse *Fragilis* 4 Amino Acid Sequence

MPKEQQEVVVLGSPHISTSATATTINMPEISTPDHVVWSLFNTLFMNFCC

LGFVAYAYSVKSRDRKMVGDTTGAQAFASTAKCLNISSLFFTILTAIVVI

VVCAIR

Mouse *Fragilis* 4 Diseases

Mouse *Fragilis* 4 is expressed in a number of tissues, including: bowel; cerebellum; colon; embryo; head; heart; kidney; liver; lung; lymph; macrophage; mammary gland; placenta; spleen; spontaneous tumor, metastatic to mammary. stem cell origin; stomach; t cell; thymus; tumor, biopsy sample; tumor, gross tissue; tumor, metastatic to mammary; vagina.

Mouse *Fragilis* 4, as well as its human homologue, is therefore suitable for treatment or diagnosis of any disease of or associated with such tissues, in particular, cancer or tumours of such tissues.

Mouse *Fragilis* 5

Mouse *Fragilis* 5 Nucleic Acid Sequence

CTCAGCTAGGAAGACACGGCGCTGGAACCCATGGACACTTCATATCCCCG

TGAGGACCCCCGGGCTCCATCATCCCGCAAGGCTGATGCTGCAGCCCACA

CAGCCCTCTCCATGGGAAGACCTGGCCCTACACCACGAGATCACATGCTC

TGGTCTGTCTTCAGCACGATGTACCTGAATCTGTGCTGCCTTGGATTCCT

GGCGCTGGTCCACTCTGTCAAGGCCCGAGACCAGAAGATGGCTGGGAACT

TGGAGGCTGCAAGGCAGTATGGCTCCAAAGCCAAGTGCTACAACATCCTG

GCTGCAATGTGGACATTGGTGCCCCCATTGCTGCTCCTGGGACTGGTGGT

GACTGGCGCCTTGCACCTGTCCAAGTTAGCCAAAGACTCTGCGGCTTTCT

TCAGCACCAAGTTTGATGAGGAGGACTATAACTAAGAGTTCCGAGCCTGT

CCCTGAACCGAGGACAACCGGGCTAGAGCGGCCGCCACCGCGGTGGAGC

Mouse *Fragilis* 5 Amino Acid Sequence

MDTSYPREDPRAPSSRKADAAAHTALSMGTPGPTPRDHMLWSVFSTMYLN

LCCLGFLALVHSVKARDQKMAGNLEAARQYGSKAKCYNILAAMWTLVPPL

LLLGLVVTGALHLSKLAKDSAAFFSTKFDEEDYN

Mouse *Fragilis* 5 Genomic Location

Mouse *Fragilis* 5 is located on chromosome 6.

Mouse *Fragilis* 5 Diseases

Mouse *Fragilis* 5 is expressed in a number of tissues, including: embryo; tumor, gross tissue.

Mouse *Fragilis* 5, as well as its human homologue, is therefore suitable for treatment or diagnosis of any disease of or associated with such tissues, in particular, cancer or tumours of such tissues.

Mouse Fragilis 6

Mouse Fragilis 6 Nucleic Acid Sequence

```
TGAACTTCCTTGAAACAAGAGCTTCCTTGCTTCCTTTAAGCACAAAAACA
TGGTTAAGAGGGATCCTGACTCAGCTCCAGTGCCATCCACTGTGGTTTGC
ATCAACAGTGATGTTATCCAGCCGGATCACATTACCTGGTCTACATTTAA
CACAGTGTTCATGAATGGCTGCTGCCTGGGTTTCATTGCCTACATCTACT
CGGTGAAGTCCAGGGACCGGAAGATGGTGGGCGACATGACTGGGGCCCAA
TCCCATGCTTCAACCGCCAAGATTCTGAACATCCTTGCTCTGGTCATCTC
CCTCATCTTCTACATCATGCTTATCGTTTTATACAGCTTTAACTTACTAG
GTAACCAAAGATAATAGAACCACTAGTTAGGTACTAACTAGTTAGTTAGC
TAATTATTAATTAACTACTAAACTAGTACCGAATTTAGTATCTTTAGT
```

Mouse Fragilis 6 Amino Acid Sequence

```
MVKRDPDSAPVPSTWCThSDVIQPDHITWSTFNTVFMNGCCLGFIAYIYS
VKSRDRKMVGDMTGAQSHASTAKILNILALVISLIFYIMLIVLYSFNLLG
NQR
```

Mouse Fragilis 6 Genomic Location
Mouse Fragilis 6 is located on chromosome 7.

Mouse Fragilis 6 Diseases

Mouse Fragilis 6 is expressed in a number of tissues, including: dbEST Library Tissue Type restricted to Spleen; cDNA sources: in vitro fertilized eggs; lymph; spinal cord; spleen.

Mouse Fragilis 6, as well as its human homologue, is therefore suitable for treatment or diagnosis of any disease of or associated with such tissues, in particular, cancer or tumours of such tissues.

Human Ifitm1, Ifitm2 Ifitm3 and ENSG142056

Human Ifitm1, Ifitm2 Ifitm3

Figure 9A:
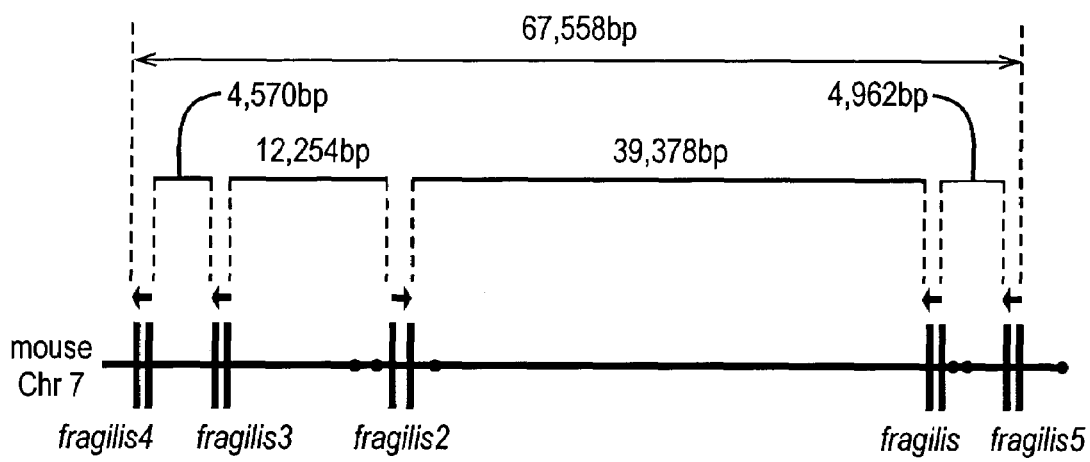
FIG. 9. The Fragilis family cluster on mouse Chr7, and the human homologues in the syntenic region on Chr11. In the mouse, the five Fragilis genes are clustered within a 70 kb region. All genes are encoded by two exons, and apart from fragilis2, they are located on the minus strand. In human, the four homologous genes, ENSG142056 and Ifitm1 (9-27), Ifitm2 (1-8D) and Ifitm3 (1-8U), are clustered within a 25 kb stretch. The four human homologues are each encoded by two exons, but the length of the intronic sequence for Ifitm1 and Ifitm3 is not known. Apart Ifitm2, all human genes are encoded on the minus strand. The green circles represent ISRE consensus sequences.
Figure 9B:
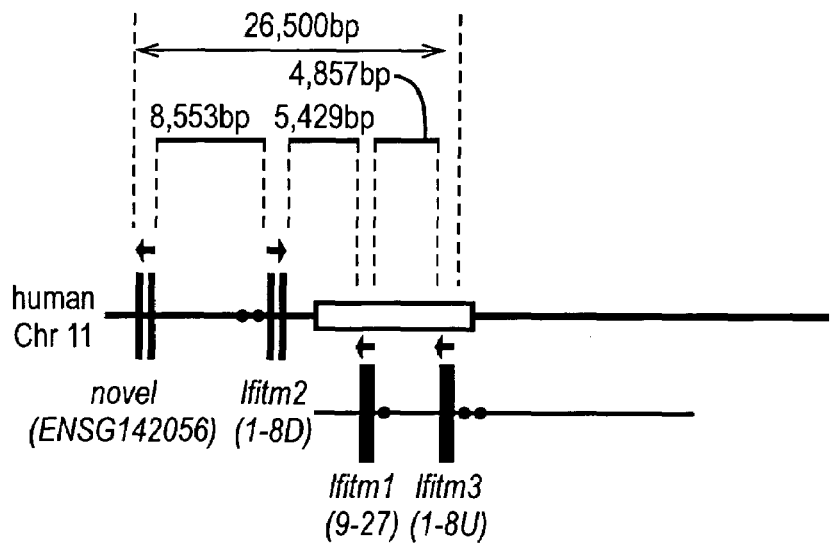
Figure 12:
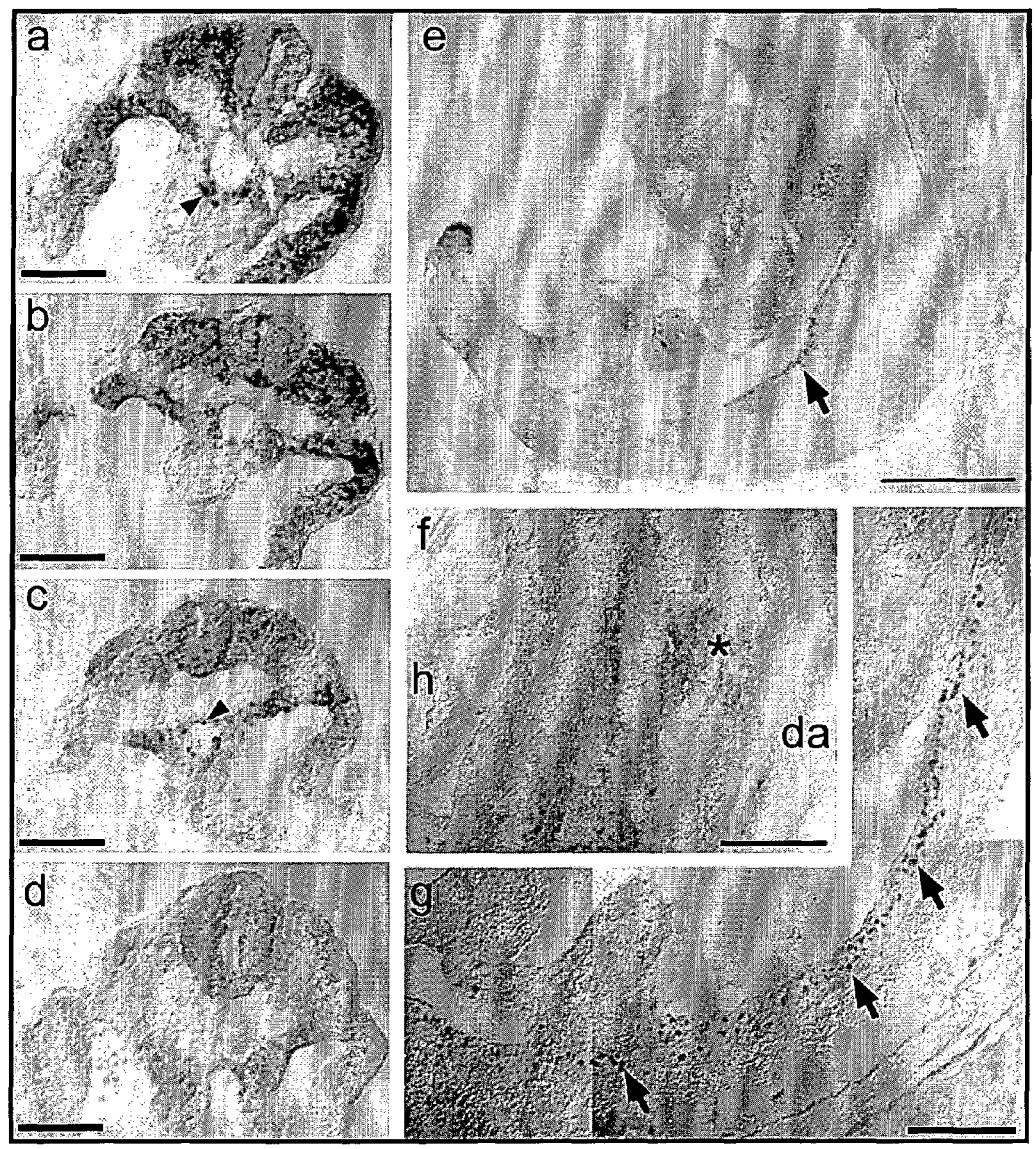
FIG. 12. Expression analysis of fragilis2 by in situ hybridisation on sections. (a-d) transverse sections through the caudal region of an embryo at E9.5 (approx. 25 somites) at progressively rostral levels. At most caudal levels, fragilis2 expression is seen in cells of the neural tube, in the presomitic mesoderm, in single cells within the hindgut (arrowhead) and in the body wall. (b) staining at approx. 23rd somite level is present within the forming somite, the body wall mesoderm and cells within the hindgut as well as the floorplate. (c) at approx. 21st somite level, expression in the differentiating somites is reduced, while cells in the floor plate and within the hindgut remain *fragilis*2 mRNA positive. (d) at approx. the 13th somite level, *fragilis*2 expression is absent from the somatic mesoderm as well as the neural tube. (e) sagittal section through an E10.5 embryo shows *fragilis*2 expression in developing lung tissue (asterix; higher magnification in f) and migrating cells along the hindgut anterior to the dorsal aorta (arrow). (g) shows a magnified view of *fragilis*2 mRNA expressing, migrating cells. da: dorsal aorta; fp: floor plate; g: gut; h: developing heart; nt: neural tube; s: somite; bw: body wall; scale bars: 150 µm (a-d); 1 mm (e); 400 µm (f, g).

We disclose four homologues of Fragilis genes, located on Chromosome 11 (p15.5). This region is syntenic to the Fragilis family locus on mouse Chr 7 (FIG. 9). Nucleic acids encoding each of these proteins are also disclosed.

Three of these genes, Ifitm1 (9-27), Ifitm2 (1-8D) and Ifitm3 (1-8U), share 58-65% similarity to the fragilis gene cluster and are located within an 18 kb genomic stretch [A R Lewin, L E Reid, M McMahon, G R Stark, I M Kerr: Molecular analysis of a human interferon-inducible gene family. Eur J Biochem 1991, 199: 417-423].

They are responsive to type1/2 interferons and code for interferon induced transmembrane (Ifitm) proteins, involved in antiproliferative signalling and homotypic cell adhesion. See R L Friedman, S P Manley, M Mcahon, I M Kerr, G R Stark: Transcriptional and posttranscriptional regulation of interferon-induced gene expression in human cells. Cell 1984, 38: 745-755; J M Kelly, C S Gilbert, G R Stark, I M Kerr: Differential regulation of interferon-induced mRNAs and c-myc mRNA by alpha- and gamma-interferons. Eur J Biochem 1985, 153: 367-371; S S Evans, D B Lee, T Han, T B Tomasi, R L Evans: Monoclonal antibody to the interferon-inducible protein Leu-13 triggers aggregation and inhibits proliferation of leukemic B cells. Blood 1990, 76 (12): 2583-2593; and S S Evans, R P Collea, J A Leasure, D B Lee: IFN-a induces homotypic adhesion and Leu-13 expression in human B lymphoid cells. J Immunol 1993, 150: 736-747.

Interferon stimulable response elements (ISREs, GGAAAN(N)GAAAC) within the human Ifitm locus confer the responsiveness of the three human Ifitm genes to interferons (A R Lewin, L E Reid, M McMahon, G R Stark, I M Kerr: Molecular analysis of a human interferon-inducible gene family. Eur J Biochem 1991, 199: 417-423; L E Reid, A H Brasnett, C S Gilbert, A C G Porter, D R Gewert, G R Stark, I M Kerr: A single DNA response elemnt can confer inducibility by both alpha- and gamma-interferons. Proc Natl Acad Sci USA 1989, 86: 840-844). Similar ISRE consensus sequences are also found within the Fragilis family cluster in the mouse, associated in particular with fragilis, fragilis 2 and fragilis5 (FIG. 9).

Human ENSG142056

We further disclose the fourth gene, ENSG142056, a novel gene with two exons, is highly similar to mouse fragilis4 (83% DNA sequence similarity) and neighbours Ifitm2. The human Fragilis family homologues hence form a similar genomic cluster as the five Fragilis genes in the mouse.

Other Fragilis Homologues

We also identified two Fragilis family-like genes in cow (bovine 1-8U, bovine 9-27) and four genes in rat (P26376, JC1241, NP110460, AAD48010). While the rat genes have been annotated as putative interferon inducible, the two bovine genes that are similar to the human Ifitm genes, have been reported to respond to interferon signalling (D J Hayzer, E Brinson, M S Runge: A rat beta-interferon-induced mRNA: sequence characterization. Gene 1992, 117 (2): 227-228; 17. J K Pru, K J Austin, A L Haas, T R Hansen: Pregnancy and interferon-tau upregulate gene expression of members of the 1-8 family in the bovine uterus. Biol Reprod 2001, 65 (5): 1471-1480).

Functions of Human and Stella

The functions of human Stella and Fragilis are disclosed throughout this document. It is also expected that human Stella and Fragilis will broadly display the properties of their mouse counterparts. The functional homology of the human sequences disclosed here to their mouse Stella and Fragilis counterparts may be verified by a complementation test. An example of such a complementation test is set out in the following paragraphs.

Mouse mutants for Stella and Fragilis are created by gene knockout technology using ES cells, using standard techniques. Further details are provided in the Examples, particularly Examples 11 to 15. Human SETLLA and FRAGILIS clones may be isolated by screening human genomic libraries, such as BAC libraries, or by nucleotide synthesis or PCR of a human cDNA library using the sequences disclosed here.

These BAC clones may then be introduced into the mouse genome by microinjection of the genomic clones into the oocyte or by transfection, lipofection or by using viral vectors, into ES cells. Transgenic mice carrying human homologues of SETLLA and FRAGILIS are generated and crossed with mouse mutants for Stella or Fragilis. If the human homologue contains appropriate regulatory sequences and is therefore is expressed similarly to the mouse gene, it will overcome phenotypic deficiencies in mutant mice, if it is a true homologue. The wild type phenotype will be restored to the transgenic knockout mouse.

BAC clones may be modified to contain reporter genes such as GFP. When introduced into the mouse genome to generate transgenic mice, the reporter constructs can be used to verify whether the human homologue shows appropriate temporal and spatial patterns of expression. This expression analysis combined with the phenotypic rescue of mutants described above would verify if the human genes are the homologues of murine genes.

There are other ways in which murine and human genes can be tested for their effects on murine tumours. If the tumours are the result of gain of function, it would be possible to use RNAi or other antisense approaches to see if repression of modifies the phenotype. If tumours result from loss of function, transgenes (as BACs or under the control of appropriate tissue-specific regulatory sequences) can be introduced into cells or mice to check if they have an effect on tumours.

The procedure for BAC modifications and the generation of transgenic mice may employ the technique described in Developmental Biology, volume 236, 2001 by John, R M et al, or any other suitable technique.

*Stella* Diseases and *Fragilis* Associated Diseases

Human *Stella* and *Fragilis* are expressed in a number of tissues and cells, and in particular in a number of tumour or cancerous cells and tissues, as described in further detail below. Accordingly, the *Stella* and/or *Fragilis* polypeptides, nucleic acids, antibodies, peptides, etc described here may be used in the diagnosis and I or treatment or prevention of any diseases associated with such tissues and cells, for example, tumours or cancers of the tissues and cells.

Examples of diseases associated with *Stella* and *Fragilis* are set out in the sections above relating to individual *Stella* and *Fragilis* sequences.

Particular further examples of such tumours and cancers include, but are not limited to, testis tumor, colon tumor, stomach, germ cell tumors, choriocarcinoma, lung, large cell carcinoma, uterus, and leiomyosarcoma. Alternatively or in addition, *Stella* and/or *Fragilis* associated diseases include any one or more of diseases of the following tissues, including: adenocarcinoma; adrenal cortico adenoma for cushing's syndrome; cervical carcinoma; Crohn's disease; embryonal carcinoma; endometrium adenocarcinoma; epithelioid carcinoma; poorly-differentiated adenocarcinomas; acute myelogenous leukemia; chronic myelogenous leukemia; hepatocellular carcinoma; hypernephroma; insulinoma; iris; kidney tumor, large cell carcinoma; large cell carcinoma, undifferentiated; leiomyosarcoma; lung focal fibrosis; metastatic chondrosarcoma; mucoepidermoid carcinoma; neuroblastoma; papillary serous ovarian metastasis; parathyroid; pheochromocytoma; prostate tumor; serous papillary tumor; squamous cell carcinoma, preferably poorly differentiated.

*Stella* and *Fragilis* Polypeptides

It will be understood that polypeptide sequences disclosed here are not limited to the particular sequences set forth in the sequence listing, or fragments thereof, or sequences obtained from *Fragilis* or *Stella* protein, but also include homologous sequences obtained from any source, for example related cellular homologues, homologues from other species and variants or derivatives thereof, provided that they have at least one of the biological activities of *Stella* or *Fragilis* (including related sequences such as *Fragilis* 2, 3, 4, 5 and 6), as the case may be.

This disclosure therefore encompasses variants, homologues or derivatives of the amino acid sequences set forth in this description, including in the sequence listings, as well as variants, homologues or derivatives of the amino acid sequences encoded by the nucleotide sequences disclosed here. In a preferred embodiment, the homologues and variants of *Stella* and *Fragilis* do not include the sequences disclosed in PCT/GB02/00215, in particular do not include the mouse *Stella* and *Fragilis* sequences set out in SEQ ID NO: 2 and 1 respectively. Furthermore, they preferably do not include any sequence portion of these genes previously disclosed without any indication of function, for example, AC006927.26.74831.117191 (Chromosome 12, p12.3). In particular, preferred embodiments do not comprise any EST (Expressed Sequence Tag) which may have been disclosed, for example, any one or more of the following ESTs: gi|1953020|gb|AA300687.1|AA300687 EST13535 Testis tumor cDNA 5' end; gi|8149136|gb|AW959452.1|AW959452 EST371522 MAGE resequences, MAGF cDNA (colon tumor); gi|10896747|gb|BF091037.1|BF091037 MR3-SN0036-120900-007-h05 SN0036 cDNA (stomach normal); and gi|3367222|gb|AI066520.1|AI066520 ov17h01.x1 NCI_C-GAP_GC3 cDNA clone IMAGE:1637617 3' (pooled germ cell tumors)

In further preferred embodiments, the variants, homologues, etc of *Stella* and *Fragilis* do not include any one or more of the following ESTs: gi|2335869|gb|AA564230.1|AA564230 nk43h01.s1 NCI_CGAP_GC2 cDNA clone IMAGE:1016305 3' (germ cell tumor); gi|3076239|gb|AA927342.1|AA927342 om69e05.s1 NCI_CGAP_GC4 cDNA clone IMAGE: 1552448 3' (pooled germ cell tumors); gi|2959237|gb|AA864924.1 AA864924 oh44h08.s1 NCI_CGAP_GC4 cDNA clone IMAGE:1469535 3' (pooled germ cell tumors); gi|9512276|gb|BE466414.1|BE466414 hz21d11.x1 NCI_CGAP_GC6 cDNA clone IMAGE: 3208629 3' (pooled germ cell tumors); gi|5837653|gb|AI990772.1|AI990772 ws23f02.x1 NCI_C-GAP_GC6 cDNA clone IMAGE:2498043 3' (pooled germ cell tumors); gi|5741162|gb|AI1948852.1|AI948852 wq37c09.x1 NCI_CGAP_GC6 cDNA clone IMAGE: 2473456 3' (pooled germ cell tumors); gi|4734510|gb|AI650531.1|AI650531 wa92b04.x1 NCI_C-GAP_GC6 cDNA clone IMAGE:2303599 3' (pooled germ cell tumors); gi|5849349|gb|AW002433.1|W002433 wu61h07.x1 NCI_CGAP_GC6 cDNA clone IMAGE: 2524573 3' (pooled germ cell tumors); gi|5746921|gb|AI1954611.1|AI954611 wq34b05.x1 NCI_CGAP_GC6 cDNA clone IMAGE:2473137 3' (pooled germ cell tumors); gi|4735956|gb|AI651977.1|AI651977 wb64h02.x1 NCI_CGAP_GC6 cDNA clone IMAGE: 2310483 3' (pooled germ cell tumors); gi|19763950|gb|BQ028671.1|BQ028671 UI-1-EEO-ayz-b-02-0-UI.s1; NCI_CGAP_P17 cDNA clone UI-1-EEO-ayz-b-02-0-UI 3' (choriocarcinoma); gi|9890324|gb|BE619386.1|BE619386 601473204F1 NIH_MGC_68 cDNA clone IMAGE:3876145 5' (lung, large cell carcinoma); gi|10344247|gb|BE888191.1|BE888191 601511709F1 NIH_MGC_71 cDNA clone IMAGE:3912866 5' (uterus, leiomyosarcoma); and gi|1933621|gb|AA286758.1|AA286758 zs51a11.r1 NCI_C-GAP_GCB1 cDNA clone IMAGE:700988 5' (germinal center B cell).

Homologues

The polypeptides disclosed include homologous sequences obtained from any source, for example related viral/bacterial proteins, cellular homologues and synthetic peptides, as well as variants or derivatives thereof. Thus polypeptides also include those encoding homologues of *Fragilis* and/or *Stella* from other species including animals such as mammals (e.g. mice, rats or rabbits), especially primates, more especially humans. More specifically, homologues include human homologues.

In the context of the present document, a homologous sequence or homologue is taken to include an amino acid sequence which is at least 60, 70, 80 or 90% identical, preferably at least 95 or 98% identical at the amino acid level over at least 30, preferably 50, 70, 90 or 100 amino acids with *Fragilis* or *Stella*, for example as shown in the sequence listing herein. In the context of this document, a homologous sequence is taken to include an amino acid sequence which is at least 15, 20, 25, 30, 40, 50, 60, 70, 80 or 90% identical, preferably at least 95 or 98% identical at the amino acid level, preferably over at least 50 or 100, preferably 200, 300, 400 or 500 amino acids with the sequence of *Fragilis* or *Stella*, for example *Fragilis* (SEQ ID NO: 6) and *Stella* (SEQ ID NO: 4), or the *Fragilis* family member sequences *Fragilis* 9-27 (preferably comprising a sequence as shown in SEQ ID NO: 8), *Fragilis* 2 (preferably comprising a sequence as shown in SEQ ID NO: 10), *Fragilis* 3 (preferably comprising a sequence as shown in SEQ ID NO: 12), *Fragilis* 4 (preferably comprising a sequence as shown in SEQ ID NO: 14), *Fragilis* 5 (preferably comprising a sequence as shown in SEQ ID NO: 16) and *Fragilis* 6 (preferably comprising a sequence as shown in SEQ ID NO: 18).

Although homology can also be considered in terms of similarity (i.e. amino acid residues having similar chemical properties/functions), in the context of the present document it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et a., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. Preferably, the resultant amino acid sequence retains substantially the same activity as the unmodified sequence, preferably having at least the same activity as the *Fragilis* and/or *Stella* polypeptides shown in the sequence listings. Thus, the key feature of the sequences—namely that they are specific for PGCs and other pluripotent cells, such as ES or EG cells, and can serve as a marker for these cells in a cell population—is preferably retained.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of *Fragilis* and *Stella* are likely to comprise conservative amino acid substitutions. Conservative substitutions may be defined, for example according to the Table below. Amino acids in the same block in the second column and preferably in the same line in the third column may be substituted for each other:

| ALIPHATIC | Non-polar | GAP |
| | | ILV |
| | Polar - uncharged | CSTM |
| | | NQ |
| | Polar - charged | DE |
| | | KR |
| AROMATIC | | HFWY |

Fragments

Polypeptides disclosed here and useful as markers also include fragments of the above mentioned full length polypeptides and variants thereof, including fragments of the sequences set out in SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18.

Polypeptides also include fragments of the full length sequence of any of the *Fragilis* and/or *Stella* polypeptides. Preferably fragments comprise at least one epitope. Methods of identifying epitopes are well known in the art. Fragments will typically comprise at least 6 amino acids, more preferably at least 10, 20, 30, 50 or 100 amino acids.

Included are fragments comprising, preferably consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145 or 150, or more residues from a *Fragilis* and/or *Stella* amino acid sequence.

Polypeptide fragments of the *Stella/Fragilis* proteins and allelic and species variants thereof may contain one or more (e.g. 5, 10, 15, or 20) substitutions, deletions or insertions, including conserved substitutions. Where substitutions, deletion and/or insertions occur, for example in different species, preferably less than 50%, 40% or 20% of the amino acid residues depicted in the sequence listings are altered.

*Fragilis* and *Stella*, and their fragments, homologues, variants and derivatives, may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence. Proteins may also be obtained by purification of cell extracts from animal cells.

The *Fragilis* and/or *Stella* polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A *Fragilis/Stella* variant, homologue, fragment or derivative may also be in a substantially purified form, in which case it will generally comprise the protein in a preparation in which more than 90%, e.g. 95%, 98% or 99% of the protein in the preparation is a protein.

The *Fragilis/Stella* polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

*Fragilis/Stella* polypeptides, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The *Fragilis/Stella* polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the *Fragilis/Stella* polypeptides, variants, homologues, fragments and derivatives disclosed here are expressed may be used in assay systems to identify candidate substances which interfere with or enhance the functions of the polypeptides in the cell.

*Fragilis/Stella* Nucleic Acids

We provide generally for a number of *Fragilis* and *Stella* nucleic acids, together with fragments, homologues, variants and derivatives thereof. These nucleic acid sequences preferably encode the polypeptide sequences disclosed here, and particularly in the sequence listings. Preferably, the polynucleotides comprise *Stella* and/or *Fragilis* nucleic acids, preferably selected from the group consisting of: SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17 or fragments, homologues, variants and derivatives thereof.

In particular, we provide for nucleic acids which encode any of the *Fragilis* and/or *Stella* polypeptides disclosed here. Thus, the terms "GCR nucleic acid", "*Fragilis* nucleic acid" and "*Stella* nucleic acid" should be construed accordingly. Preferably, however, such nucleic acids comprise any of the sequences set out as SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17 or a sequence encoding any of the corresponding polypeptides, and a fragment, homologue, variant or derivative of such a nucleic acid The above terms therefore preferably should be taken to refer to these sequences.

In preferred embodiments, the *Stella* nucleic acid comprises a nucleic acid having a sequence set out in SEQ ID NO: 3 and the *Fragilis* nucleic acid comprises a nucleic acid having a sequence set out in SEQ ID NO: 5. However, also included are nucleic acids encoding any *Fragilis* family member, for example: *Fragilis* 9-27 (preferably a sequence as shown in SEQ ID NO: 7), *Fragilis* 2 (preferably a sequence as shown in SEQ ID NO: 9), *Fragilis* 3 (preferably a sequence as shown in SEQ ID NO: 11), *Fragilis* 4 (preferably a sequence as shown in SEQ ID NO: 13), *Fragilis* 5 (preferably a sequence as shown in SEQ ID NO: 15) and *Fragilis* 6 (preferably a sequence as shown in SEQ ID NO: 17).

As used here in this document, the terms "polynucleotide", "nucleotide", and nucleic acid are intended to be synonymous with each other. "Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Variants, Derivatives and Homologues

The polynucleotides described here may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleotides from or to the sequence providing the resultant nucleotide sequence is specific for pluripotent cells, preferably specific for PGCs, ES cells or EG cells. Most preferably, the resultant nucleotide sequence is specific for PGCs.

As indicated above, with respect to sequence identity, a "homologue" has preferably at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence shown in the sequence listings.

More preferably there is at least 95% identity, more preferably at least 96% identity, more preferably at least 97% identity, more preferably at least 98% identity, more preferably at least 99% identity. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

In a preferred aspect, we disclose nucleotide sequences that can hybridise to a *Fragilis/Stella* nucleic acid, or a fragment, homologue, variant or derivative thereof, under stringent conditions (e.g. 65° C. and 0.1×SSC {1×SSC=0.15 M NaCl, 0.015 M $Na_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells, including human cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of SEQ ID NOs: 1 or 3 under conditions of medium to high stringency. Similar considerations apply to obtaining species homologues and allelic variants of *Fragilis* and *Stella*.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides as used herein. Preferred fragments are less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Nucleotide Vectors The polynucleotides can be incorporated into a recombinant replicable vector. The vector may be used to replicate the nucleic acid in a compatible host cell. Thus in a further embodiment, we provide a method of making polynucleotides by introducing a polynucleotide into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host cell as described below to provide for expression of a protein. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the Rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Expression of *Stella* and/or *Fragilis* Polypeptides

In order to express a biologically active *Stella* and/or *Fragilis*, the nucleotide sequences encoding *Stella* and/or *Fragilis* or homologues, variants, or derivatives thereof are inserted into appropriate expression vector, i.e., a vector which contains the necessary elements for the transcription and translation of the inserted coding sequence.

Methods which are well known to those skilled in the art are used to construct expression vectors containing sequences encoding *Stella* and/or *Fragilis* and appropriate transcriptional and translational control elements. These methods include in vitro recombinant DNA techniques, synthetic techniques, and in vivo genetic recombination. Such techniques are described in Sambrook, J. et al. (1989; Molecular Cloning, A Laboratory Manual, ch. 4, 8, and 16-17, Cold Spring Harbor Press, Plainview, N.Y.) and Ausubel, F. M. et al. (1995 and periodic supplements; Current Protocols in Molecular Biology, ch. 9, 13, and 16, John Wiley & Sons, New York, N.Y.).

A variety of expression vector/host systems may be utilized to contain and express sequences encoding *Stella* and/or *Fragilis*. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. Any suitable host cell may be employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding *Stella* and/or *Fragilis*, vectors based on SV40 or EBV may be used with an appropriate selectable marker.

In bacterial systems, a number of expression vectors may be selected depending upon the use intended for *Stella* and/or *Fragilis*. For example, when large quantities of *Stella* and/or *Fragilis* are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding *Stella* and/or *Fragilis* may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503-5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516-544).

In cases where plant expression vectors are used, the expression of sequences encoding *Stella* and/or *Fragilis* may be driven by any of a number of promoters. For example, viral promoters such as the 35S and 19S promoters of CaMV may be used alone or in combination with the omega leader sequence from TMV. (Takamatsu, N. (1987) EMBO J. 6:307-311.) Alternatively, plant promoters such as the small subunit of RUBISCO or heat shock promoters may be used. (Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. Such techniques are described in a number of generally available reviews. (See, for example, Hobbs, S. or Murry, L. E. in McGraw Hill Yearbook of Science and Technology (1992) McGraw Hill, New York, N.Y.; pp. 191-196.).

An insect system may also be used to express *Stella* and/or *Fragilis*. For example, in one such system, *Autographa californica* nuclear polyhedrosis virus (AcNPV) is used as a vector to express foreign genes in *Spodoptera frugiperda* cells or in *Trichoplusia* larvae. The sequences encoding *Stella* and/or *Fragilis* may be cloned into a non-essential region of the virus, such as the polyhedrin gene, and placed under control of the polyhedrin promoter. Successful insertion of *Stella* and/or *Fragilis* will render the polyhedrin gene inactive and produce recombinant virus lacking coat protein. The recombinant viruses may then be used to infect, for example, *S. frugiperda* cells or *Trichoplusia* larvae in which *Stella* and/or *Fragilis* may be expressed. (Engelhard, E. K. et al. (1994) Proc. Nat. Acad. Sci. 91:3224-3227.)

In mammalian host cells, a number of viral-based expression systems may be utilized. In cases where an adenovirus is used as an expression vector, sequences encoding *Stella* and/or *Fragilis* may be ligated into an adenovirus transcription/translation complex consisting of the late promoter and tripartite leader sequence. Insertion in a non-essential E1 or E3 region of the viral genome may be used to obtain a viable virus which is capable of expressing *Stella* and/or *Fragilis* in infected host cells. (Logan, J. and T. Shenk (1984) Proc. Natl. Acad. Sci. 81:3655-3659.) In addition, transcription enhancers, such as the Rous sarcoma virus (RSV) enhancer, may be used to increase expression in mammalian host cells.

Thus, for example, the *Stella* and/or *Fragilis* proteins are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding *Stella* and/or *Fragilis*. Such signals include the ATG initiation codon and adjacent sequences. In cases where sequences encoding *Stella* and/or *Fragilis* and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125-162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing *Stella* and/or *Fragilis* can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223-32) and adenine phosphoribosyltransferase genes (Lowy, I. et al. (1980) Cell 22:817-23), which can be employed in tk⁻ or apr⁻ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567-70); npt confers resistance to the aminoglycosides neomycin and G418 (Colbere-Garapin, F. et al (1981) J. Mol. Biol. 150:1-14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047-51.) Recently, the use of visible markers has gained popularity with such markers as anthocyanins, .β-glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55;121-131.)

Although the presence/absence of marker gene expression suggests that the gene of interest is also present, the presence and expression of the gene may need to be confirmed. For example, if the sequence encoding *Stella* and/or *Fragilis* is inserted within a marker gene sequence, transformed cells containing sequences encoding *Stella* and/or *Fragilis* can be identified by the absence of marker gene function. Alternatively, a marker gene can be placed in tandem with a sequence encoding *Stella* and/or *Fragilis* under the control of a single promoter. Expression of the marker gene in response to induction or selection usually indicates expression of the tandem gene as well.

Alternatively, host cells which contain the nucleic acid sequence encoding *Stella* and/or *Fragilis* and express *Stella* and/or *Fragilis* may be identified by a variety of procedures known to those of skill in the art. These procedures include, but are not limited to, DNA--DNA or DNA-RNA hybridizations and protein bioassay or immunoassay techniques which include membrane, solution, or chip based technologies for the detection and/or quantification of nucleic acid or protein sequences.

The presence of polynucleotide sequences encoding *Stella* and/or *Fragilis* can be detected by DNA-DNA or DNA-RNA hybridization or amplification using probes or fragments or fragments of polynucleotides encoding *Stella* and/or *Fragilis*. Nucleic acid amplification based assays involve the use of oligonucleotides or oligomers based on the sequences encoding *Stella* and/or *Fragilis* to detect transformants containing DNA or RNA encoding *Stella* and/or *Fragilis*.

A variety of protocols for detecting and measuring the expression of *Stella* and/or *Fragilis*, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on *Stella* and/or *Fragilis* is preferred, but a competitive binding assay may be employed. These and other assays are well described in the art, for example, in Hampton, R. et al. (1990;

Serological Methods, a Laboratory Manual, Section IV, APS Press, St Paul, Minn.) and in Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding *Stella* and/or *Fragilis* include oligolabeling, nick translation, end-labeling, or PCR amplification using a labeled nucleotide. Alternatively, the sequences encoding *Stella* and/or *Fragilis*, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding *Stella* and/or *Fragilis* may be cultured under conditions suitable for the expression and recovery of the protein from cell culture. The protein produced by a transformed cell may be located in the cell membrane, secreted or contained intracellularly depending on the sequence and/or the vector used. As will be understood by those of skill in the art, expression vectors containing polynucleotides which encode *Stella* and/or *Fragilis* may be designed to contain signal sequences which direct secretion of *Stella* and/or *Fragilis* through a prokaryotic or eukaryotic cell membrane. Other constructions may be used to join sequences encoding *Stella* and/or *Fragilis* to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the *Stella* and/or *Fragilis* encoding sequence may be used to facilitate purification. One such expression vector provides for expression of a fusion protein containing *Stella* and/or *Fragilis* and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263-281), while the enterokinase cleavage site provides a means for purifying *Stella* and/or *Fragilis* from the fusion protein. A discussion of vectors which contain fusion proteins is provided in Kroll, D. J. et al. (1993; DNA Cell Biol. 12:441-453).

Fragments of *Stella* and/or *Fragilis* may be produced not only by recombinant production, but also by direct peptide synthesis using solid-phase techniques. (Merrifield J. (1963) J. Am. Chem. Soc. 85:2149-2154.) Protein synthesis may be performed by manual techniques or by automation. Automated synthesis may be achieved, for example, using the Applied Biosystems 431A peptide synthesizer (Perkin Elmer). Various fragments of *Stella* and/or *Fragilis* may be synthesized separately and then combined to produce the full length molecule.

Recombinant *Stella* and *Fragilis* Proteins

We also provide for expression of *Stella* and *Fragilis* proteins, for example, recombinant proteins. These may be expressed by a number of methods as generally known in the art; the following provides an example of how this may be achieved.

Nucleotide sequences of *Stella* and *Fragilis* are cloned into a TRI-system vector (Qiagen). *Stella* sequence comprising the second codon onwards (i.e., an N terminal fragment of *Stella* without the first ATG codon) is cloned into a pQE vector using appropriate restriction enzyme sites, and according to the manufacturers instructions. QIAexpress pQE vectors enable high-level expression of 6×His-tagged proteins in *E. coli*.

A His tag is placed in the N terminal portion of the *Stella* gene. Recombinant protein is purified by affinity chromatography on a Ni-NTA column, according to manufacturer's instructions. The His tag is cleaved using a suitable protease.

Recombinantly expressed *Stella* and *Fragilis* protein are found to be biologically active.

Modulators, Agonists and Antagonists

The methods and compositions described here rely, in some embodiments, on blocking, reducing, or increasing the activity of proteins such as *Stella* and *Fragilis*, for example, in methods of treating or preventing a disease such as cancer. In general, the methods employ modulators of *Stella* and/or *Fragilis* activity or expression.

Agents which are capable of increasing the activity of a the *Stella* and/or *Fragilis* protein are referred to as agonists of that activity. Similarly, antagonists reduce the activity of the relevant protein.

The term "antagonist", as used in the art, is generally taken to refer to a compound which binds to an enzyme and inhibits the activity of the enzyme. The term as used here, however, is intended to refer broadly to any agent which inhibits the activity of a molecule, not necessarily by binding to it. Accordingly, it includes agents which affect the expression of a protein such as *Stella* or *Fragilis*, or the biosynthesis of a regulatory molecule, or the expression of modulators of the activity of the *Stella* or *Fragilis*. The specific activity which is inhibited may be any activity which is exhibited by, or characteristic of, the enzyme or molecule, for example, any activity of *Stella* and/*Fragilis* as the case may be, for example, a signal transduction activity or PGC specification activity.

The antagonist may bind to and compete for one or more sites on the relevant molecule preferably, the catalytic site of the enzyme. Preferably, such binding blocks the interaction between the molecule and another entity (for example, the interaction between a enzyme and its substrate). However, the antagonist need not necessarily bind directly to a catalytic site, and may bind for example to an adjacent site, another protein (for example, a protein which is complexed with the enzyme) or other entity on or in the cell, so long as its binding reduces the activity of the enzyme or molecule.

Where antagonists of a enzyme such as a enzyme are concerned, an antagonist may include a substrate of the enzyme, or a fragment of this which is capable of binding to the enzyme. In addition, whole or fragments of a substrate generated natively or by peptide synthesis may be used to compete with the substrate for binding sites on the enzyme. Alternatively, or in addition, an immunoglobulin (for example, a monoclonal or polyclonal antibody) capable of binding to the enzyme may be used. The antagonist may also include a peptide or other small molecule which is capable of interfering with the binding interaction. Other examples of antagonists are set forth in greater detail below, and will also be apparent to the skilled person.

Blocking the activity of an inhibitor of the relevant *Stella* and/or *Fragilis* protein may also be achieved by reducing the level of expression of the protein or an inhibitor in the cell. For example, the cell may be treated with antisense compounds, for example oligonucleotides having sequences specific to the *Stella* and/or *Fragilis* mRNA. The level of expression of pathogenic forms of adhesion proteins may also be regulated this way.

In general, agaonists, antagonists and modulators comprise agents such as an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc, or otherwise in a complex.

The terms "modulator", "antagonist" and "agent" are also intended to include, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanised, a peptide hormone, a receptor, a signalling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. Small molecules, including inorganic and organic chemicals, which bind to and occupy the active site of the polypeptide thereby making the catalytic site inaccessible to substrate such that normal biological activity is prevented, are also included. Examples of small molecules include but are not limited to small peptides or peptide-like molecules.

In a particular embodiment, the technique of RNA interference (RNAi) may be used to abolish or knock out or reduce gene activity, for example, *Stella* and/or *Fragilis* activity. The overall strategy is to prepare double stranded RNA (dsRNA) specific to each gene of interest and to transfect this into a cell of interest to inhibit the expression of the particular gene.

The following protocol may be used: a sample of PCR product is analysed by horizontal gel electrophoresis and the DNA purified using a Qiagen QiaQuick PCR purification kit. 1 µg of DNA is used as the template in the preparation of gene specific single stranded RNA using the Ambion T7 Megascript kit. Single stranded RNA is produced from both strands of the template and is purified and immediately annealed by heating to 90 degrees C. for 15 mins followed by gradual cooling to room temperature overnight. A sample of the dsRNA is analysed by horizontal gel electrophoresis, and introduced into the relevant cell by conventional means.

Identifying Modulators, Agonists and Antagonists

Modulators, agonists and antagonists of *Stella* and/or *Fragilis* activity or expression may be identified by any means known in the art. Putative such molecules may be identified by their binding to *Stella* and/or *Fragilis*, in an assay which detects binding between *Stella* (or *Fragilis* as the case may be) and the putative molecule.

Assays to detect modulators, agonists or antagonists typically involve detecting modulation of any activity of *Stella* and/or *Fragilis* in the presence, optionally together with detection of modulation of activity in the absence, of a candidate molecule. The assays involve contacting a candidate molecule with *Stella* or *Fragilis*, whether in the form of a polypeptide, a nucleic acid encoding the polypeptide, or a cell, organelle, extract, or other material comprising such, with a candidate modulator. The relevant activity of *Stella* or *Fragilis* (as described below) may be detected, to establish whether the presence of the candidate modulator has any effect Promoter binding assays to detect candidate modulators which bind to and/or affect the transcription or expression of *Stella* and/or *Fragilis* may also be used. Candidate modulators may then be chosen for further study, or isolated for use. Details of such screening procedures are well known in the art, and are for example described in, Handbook of Drug Screening, edited by Ramakrishna Seethala, Prabhavathi B. Fernandes (2001, New York, N.Y., Marcel Dekker, ISBN 0-8247-0562-9).

The screening methods described here preferably employ in vivo assays, although they may be configured for in vitro use. In vivo assays generally involve exposing a cell comprising *Stella* and/or *Fragilis* to the candidate molecule. In in vitro assays, *Stella* and/or *Fragilis* is exposed to the candidate molecule, optionally in the presence of other components, such as crude or semi-purified cell extract, or purified proteins. Where in vitro assays are conducted, these preferably employ arrays of candidate molecules (for example, an arrayed library). In vivo assays are preferred. Preferably, therefore, the *Stella* and/or *Fragilis* is comprised in a cell, preferably heterologously. Such a cell is preferably a transgenic cell, which has been engineered to express *Stella* and/or *Fragilis*.

It will be appreciated that any component of a cell comprising *Stella* and/or *Fragilis* may be employed, such as an organelle. A preferred embodiment utilises a nuclear preparation, e.g., comprising a cell nucleus which comprises *Stella* and/or *Fragilis* as described. The nuclear preparation may comprise one or more nuclei, which may be permeabilised or semi-permeabilised, by detergent treatment, for example.

Thus, in a specific embodiment, an assay format may include the following: a multiwell microtitre plate is set up to include one or more cells expressing *Stella* and/or *Fragilis* in each well; individual candidate molecules, or pools of candidate molecules, may be added to individual wells and modulation of *Stella* and/or *Fragilis* activity measured. Where pools are used, these may be subdivided in to further pools and tested in the same manner.

Alternatively or in addition to the assay methods described above, "subtractive" procedures may also be used to identify modulators, agonists or antagonists of *Stella* and/or *Fragilis*. Under such "subtractive" procedures, a plurality of molecules is provided, which comprises one or more candidate molecules capable of functioning as a modulator (e.g., cell extract, nuclear extract, library of molecules, etc), and one or more components is removed, depleted or subtracted from the plurality of molecules. The "subtracted" extract, etc, is then assayed for activity, by exposure to a cell comprising *Stella* and/or *Fragilis* (or a component thereof) as described.

Thus, for example, an 'immunodepletion' assay may be conducted to identify such modulators as follows. A nuclear extract may be prepared from a pluripotent cell, for example, a pluripotent EG/ES cell. The extract may be depleted or fractionated to remove putative modulators, such as by use of immunodepletion with appropriate antibodies. If the extract is depleted of a modulator, it will lose the ability to affect *Stella* and/or *Fragilis* function or activity or expression. A series of subtractions and/or depletions may be required to identify the modulators, agonists or antagonists.

It will also be appreciated that the above "depletion" or "subtraction" assay may be used as a preliminary step to identify putative modulatory factors for further screening. Furthermore, or alternatively, the "depletion" or "subtraction" assay may be used to confirm the modulatory activity of a molecule identified by other means (for example, a "positive" screen as described elsewhere in this document) as a putative modulator.

Candidate molecules subjected to the assay and which are found to be of interest may be isolated and further studied. Methods of isolation of molecules of interest will depend on the type of molecule employed, whether it is in the form of a library, how many candidate molecules are being tested at any one time, whether a batch procedure is being followed, etc.

The candidate molecules may be provided in the form of a library. In a preferred embodiment of the invention, more than one candidate molecule is screened simultaneously. A library of candidate molecules may be generated, for example, a polypeptide library, a nucleic acid library, a library of compounds (such as a combinatorial library), a library of antisense molecules such as antisense DNA or antisense RNA, an antibody library etc, by means known in the art. Such libraries are suitable for high-throughput screening. Different cells comprising *Stella* and/or *Fragilis* may be exposed to individual members of the library, and expression of the reporter or reporters detected. Array technology may be employed for this purpose. The cells may be spatially separated, for example, in wells of a microtitre plate.

In a preferred embodiment, a small molecule library is employed. By this term, we refer to a library of molecules, whose molecular weights are individually less than about 50 kDa. In particular embodiments, small molecule libraries comprise molecules having molecular weights preferably less than about 30 kDa, more preferably less than about 15 kDa, most preferably less than 10 kDa or so. Such "small molecule" libraries may contain polypeptides, small peptides, for example, peptides of 20 amino acids or fewer, for example, 15, 10 or 5 amino acids, simple compounds, etc.

Alternatively or in addition, a combinatorial library, as described in further detail below, may be screened for modulators, antagonists or agonists of *Stella* and/or *Fragilis*.

Any of the activities of *Stella* and/or *Fragilis* may be used as the basis of the assay. In particular, cellular activities mediated by *Stella* and/or *Fragilis* may be assayed to identify antagonists. For example, *Fragilis* family members are responsible for homotypic adhesion between cells, and effects of the putative antagonist or agonist on adhesion activity mediated by *Fragilis* family members may be assayed using for example cell adhesion assays as known in the art. Furthermore, we show that *Fragilis* family members are capable of lengthening cell cycle times; accordingly, the cell cycle period may be assayed in the presence and absence of a candidate molecule to identify antagonists or agonists of *Fragilis* activity.

Libraries

Libraries of candidate molecules, such as libraries of polypeptides or nucleic acids, may be employed in the methods and compositions described here. Such libraries are exposed to the nucleic acid encoding the reporter (or cell comprising such a nucleic acid), for the detection of expression of the reporter.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) *Proc. Natl. Acad. Sci. USA.,* 88: 4363; Clackson et al. (1991) *Nature,* 352: 624; Lowman et al. (1991) *Biochemistry,* 30: 10832; Burton et al. (1991) *Proc. Natl. Acad. Sci U.S.A.,* 88: 10134; Hoogenboom et al. (1991) Nucleic Acids Res., 19: 4133; Chang et al. (1991) J. Immunol., 147: 3610; Breitling et al. (1991) *Gene,* 104: 147; Marks et al. (1991) supra; Barbas et al. (1992) supra; Hawkins and Winter (1992) *J. Immunol.,* 22: 867; Marks et al., 1992, *J. Biol. Chem.,* 267: 16007; Lerner et al. (1992) *Science,* 258: 1313, incorporated herein by reference). Such techniques may be modified if necessary for the expression generally of polypeptide libraries.

One particularly advantageous approach has been the use of scFv phage-libraries (Bird, R. E., et al. (1988) *Science* 242: 423-6, Huston et al., 1988, Proc. Natl. Acad. Sci U.S.A., 85: 5879-5883; Chaudhary et al. (1990) Proc. Natl. Acad. Sci U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) *Science,* 246: 1275; Caton and Koprowski (1990) *Proc. Natl. Acad. Sci. U.S.A.,* 87; Mullinax et al. (1990) *Proc. Natl. Acad Sci. USA.,* 87: 8095; Persson et al. (1991) *Proc. Natl. Acad Sci. U.S.A.,* 88: 2432) and are of use in the invention. These expression systems may be used to screen a large number of different members of a library, in the order of about 10⁶ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med Chem.*, 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

The library may in particular comprise a library of zinc fingers; zinc fingers are known in the art and act as transcription factors. Suitable zinc finger libraries are disclosed in, for example, WO 96/06166 and WO 98/53057. Construction of zinc finger libraries may utilise rules for determining interaction with specific DNA sequences, as disclosed in for example WO 98/53058 and WO 98/53060. Zinc fingers capable of interacting specifically with methylated DNA are disclosed in WO 99/47656. The above zinc finger libraries may be immobilised in the form of an array, for example as disclosed in WO 01/25417. Accordingly, preferred molecules capable of altering the potency of a cell include zinc fingers.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of causing expression of the reporter, and optionally of altering the potency of the cell.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4,235-282. Reference is also made to *Combinatorial peptide library protocols* (edited by Shmuel Cabilly, Totowa, N.J.: Humana Press, c1998. *Methods in Molecular Biology*; v. 87). Specific combinatorial libraries and methods for their construction are disclosed in U.S. Pat. No. 6,168,914 (Campbell, et al), as well as in Baldwin et al. (1995), "Synthesis of a *Small Molecule Library* Encoded with Molecular Tags," J. Am. Chem. Soc. 117:5588-5589, and in the references mentioned in those documents.

In a preferred embodiment, the combinatorial library which is screened is one which is designed to potentially include molecules which interact with a component of the cell to influence gene expression. For example, combinatorial libraries against chromatin structural proteins may be screened. Other libraries which are useful for this embodiment include combinatorial libraries against histone modification enzymes (e.g., histone acetylation or histone metylation enzymes), or DNA modification, for example, DNA methylation or demethylation.

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al.1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Antibodies

Specific antagonists of *Stella* and/or *Fragilis*, which may be used to regulate the activity of these proteins (for example, for methods of treating or preventing diseases such as cancer) may include antibodies against the protein(s).

Antibodies, as used herein, refers to complete antibodies or antibody fragments capable of binding to a selected target, and including Fv, ScFv, Fab' and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution.

The antibodies according described here are especially indicated for the detection of PGCs and other pluripotent cells, such as ES or EG cells. Accordingly, they may be altered antibodies comprising an effector protein such as a label. Especially preferred are labels which allow the imaging of the distribution of the antibody in vivo or in vitro. Such labels may be radioactive labels or radioopaque labels, such as metal particles, which are readily visualisable within an embryo or a cell mass. Moreover, they may be fluorescent labels or other labels which are visualisable on tissue samples.

Recombinant DNA technology may be used to improve the antibodies as described here. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [EP 0 239 400].

Antibodies may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with *Fragilis* or *Stella*, or fragments thereof, or with Protein-A.

Hybridoma cells secreting the monoclonal antibodies are also provided. Preferred hybridoma cells are genetically stable, secrete monoclonal antibodies of the desired specificity and can be activated from deep-frozen cultures by thawing and recloning.

Also included is a process for the preparation of a hybridoma cell line secreting monoclonal antibodies directed to *Fragilis* and/or *Stella*, characterised in that a suitable mammal, for example a Balb/c mouse, is immunised with a one or more *Fragilis* or *Stella* polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with *Fragilis* and/or *Stella* are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells expressing *Fragilis* and/or *Stella* and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to *Fragilis* and/or *Stella* as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to *Fragilis* and/or *Stella* can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to *Fragilis* and/or *Stella* fused to a human constant domain g, for example γ1, γ2, γ3 or γ4, preferably γ1 or γ4. Likewise recombinant DNAs comprising an insert coding for a light chain murine variable domain of an antibody directed to *Fragilis* and/or *Stella* fused to a human constant domain κ or λ, preferably κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Anti-Peptide *Stella* and *Fragilis* Antibodies

Anti-peptide antibodies may be produced against *Stella* and *Fragilis* peptide sequences. The sequences chosen may be based on the mouse sequences as follow:

*Fragilis*: ASGGQPPNYERIKEEYE and RDRKMVGD-VTGAQAYA

*Stella*: MEEPSEKVDPMKDPET and CHYQR-WDPSENAKIGKN

Corresponding sequences from human *Stella* and *Fragilis* may be chosen for use in eliciting anti-peptide antibodies from immunised animals. Antibodies may be produced by injection into rabbits, and other conventional means, as described in for example, Harlow and Lane (supra).

Antibodies are checked by Elisa assay and by Western blotting, and used for immunostaining as described in the Examples.

Therapeutic Peptides

The polypeptides disclosed here, for example, *Stella* and *Fragilis* polypeptides, may be used therapeutically for treatment of various diseases, including cancer, in the form of peptides comprising any portion of their sequence.

Where such *Stella* and/or *Fragilis* peptides are used therapeutically, it is preferred to use peptides that do not consist solely of naturally-occurring amino acids but which have been modified, for example to reduce immunogenicity, to increase circulatory half-life in the body of the patient, to enhance bio-availability and/or to enhance efficacy and/or specificity.

A number of approaches have been used to modify peptides for therapeutic application. One approach is to link the peptides or proteins to a variety of polymers, such as polyethylene glycol (PEG) and polypropylene glycol (PPG)—see for example U.S. Pat. Nos. 5,091,176, 5,214,131 and U.S. Pat. No. 5,264,209.

Replacement of naturally-occurring amino acids with a variety of uncoded or modified amino acids such as D-amino acids and N-methyl amino acids may also be used to modify the *Stella* and/or *Fragilis* peptides.

Another approach is to use bi-functional crosslinkers, such as N-succinimidyl3-(2pyridyldithio)propionate, succinimidyl6-[3-(2pyridyldithio)propionamido]hexanoate, and sulfosuccinimidyl6-[3-(2pyridyldithio)propionamido]hexanoate (see U.S. Pat. No. 5,580,853).

It may be desirable to use derivatives of the peptides disclosed here which are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilised by a covalent modification, such as cyclization or by incorporation of γ-lactam or other types of bridges. For example, side chains can be cyclized to the backbone so as create a L-γ-lactam moiety on each side of the interaction site. See, generally, Hruby et al., "Applications of Synthetic Peptides," in Synthetic Peptides: A User's Guide: 259-345 (W. H. Freeman & Co. 1992). Cyclization also can be achieved, for example, by formation of cystine bridges, coupling of amino and carboxy terminal groups of respective terminal amino acids, or coupling of the amino group of a Lys residue or a related homologue with a carboxy group of Asp, Glu or a related homologue. Coupling of the alpha-amino group of a polypeptide with the epsilon-amino group of a lysine residue, using iodoacetic anhydride, can be also undertaken. See Wood and Wetzel, 1992, *Int'l J. Peptide Protein Res.* 39, 533-39.

Another approach described in U.S. Pat. No. 5,891,418 is to include a metal-ion complexing backbone in the peptide structure. Typically, the preferred metal-peptide backbone is based on the requisite number of particular coordinating groups required by the co-ordination sphere of a given complexing metal ion. In general, most of the metal ions that may prove useful have a co-ordination number of four to six. The nature of the co-ordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a co-ordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is Gly-Gly-Gly-Gly which has four nitrogen atoms (an $N_4$ complexation system) in the back bone that can complex to a metal ion with a co-ordination number of four.

A further technique for improving the properties of therapeutic peptides is to use non-peptide peptidomimetics. A wide variety of useful techniques may be used to elucidating the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data which comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation. An example of this approach is provided in U.S. Pat. No. 5,811,512.

Techniques for chemically synthesising therapeutic peptides are described in the above references and also reviewed by Borgia and Fields, 2000, *TibTech* 18, 243-251 and described in detail in the references contained therein.

Transgenic Animals

We further describe transgenic animals capable of expressing natural or recombinant *Stella* and/or *Fragilis*, or a homologue, variant or derivative, at elevated or reduced levels compared to the normal expression level. Included are transgenic animals ("*Stella* knockout"s or "*Fragilis* knockout"s) which do not express functional *Stella* and/or *Fragilis*, as the case may be. The *Stella* and *Fragilis* knockouts may arise as a result of functional disruption of the *Stella* and/or *Fragilis* gene or any portion of that gene, including one or more loss of function mutations, including a deletion or replacement, of the *Stella* and/or *Fragilis* gene. The mutations include single point mutations, and may target coding or non-coding regions of *Stella* and/or *Fragilis*.

Preferably, such a transgenic animal is a non-human mammal, such as a pig, a sheep or a rodent. Most preferably the transgenic animal is a mouse or a rat. Such transgenic animals may be used in screening procedures to identify agonists and/or antagonists of *Stella* and/or *Fragilis*, as well as to test for their efficacy as treatments for diseases in vivo.

Mice which are null for *Stella* and/or *Fragilis* may be used for various purposes. For example, transgenic animals that have been engineered to be deficient in the production of *Stella* and/or *Fragilis* may be used in assays to identify agonists and/or antagonists of *Stella* and/or *Fragilis*. One assay is designed to evaluate a potential drug (aa candidate ligand or compound) to determine if it produces a physiological response in the absence *Stella* and/or *Fragilis*. This may be accomplished by administering the drug to a transgenic animal as discussed above, and then assaying the animal for a particular response.

Tissues derived from the *Stella* and/or *Fragilis* knockout animals may be used in binding assays to determine whether the potential drug (a candidate ligand or compound) binds to *Stella* or *Fragilis*, as the case may be. Such assays can be conducted by obtaining a first *Stella* and/or *Fragilis* preparation from the transgenic animal engineered to be deficient in *Stella* and/or *Fragilis* production and a second *Stella* and/or *Fragilis* preparation from a source known to bind any identified ligands or compounds. In general, the first and second preparations will be similar in all respects except for the source from which they are obtained. For example, if brain tissue from a transgenic animal (such as described above and below) is used in an assay, comparable brain tissue from a normal (wild type) animal is used as the source of the second preparation. Each of the preparations is incubated with a ligand known to bind to *Stella* and/or *Fragilis*, both alone and in the presence of the candidate ligand or compound. Preferably, the candidate ligand or compound will be examined at several different concentrations.

The extent to which binding by the known ligand is displaced by the test compound is determined for both the first and second preparations. Tissues derived from transgenic animals may be used in assays directly or the tissues may be processed to isolate *Stella* and/or *Fragilis* proteins, which are themselves used in the assays. A preferred transgenic animal is the mouse. The ligand may be labeled using any means compatible with binding assays. This would include, without limitation, radioactive, enzymatic, fluorescent or chemiluminescent labeling (as well as other labelling techniques as described in further detail above).

Furthermore, antagonists of *Stella* and/or *Fragilis* may be identified by administering candidate compounds, etc, to wild type animals expressing functional *Stella* and/or *Fragilis*, and animals identified which exhibit any of the phenotypic characteristics associated with reduced or abolished expression of *Stella* and/or *Fragilis* function.

Methods for generating non-human transgenic animal are known in the art, and are described in further detail in the Examples below. Transgenic gene constructs can be introduced into the germ line of an animal to make a transgenic mammal. For example, one or several copies of the construct may be incorporated into the genome of a mammalian embryo by standard transgenic techniques.

In an exemplary embodiment, the transgenic non-human animals described here are produced by introducing transgenes into the germline of the non-human animal. Embryonal target cells at various developmental stages can be used to introduce transgenes. Different methods are used depending on the stage of development of the embryonal target cell. The specific line(s) of any animal used to produce transgenic animals are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, the *Stella* or *Fragilis* transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is also included. One common method in to incubate the embryos in vitro for about 1-7 days, depending on the species, and then reimplant them into the surrogate host.

The progeny of the transgenically manipulated embryos can be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

For the purposes of this document, a zygote is essentially the formation of a diploid cell which is capable of developing into a complete organism. Generally, the zygote will be comprised of an egg containing a nucleus formed, either naturally or artificially, by the fission of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. There will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance the methods described here will include exogenous genetic material. As set out above, the exogenous genetic material will, in certain embodiments, be a DNA sequence which results in the production of a *Stella* and/or *Fragilis* protein. Further, in such embodiments the sequence will be attached to a transcriptional control element, e.g., a promoter, which preferably allows the expression of the transgene product in a specific type of cell.

It will be appreciated that it is possible to manipulate the control elements (promoters or enhancers) to regulate the spatial or temporal expression, or both, of *Stella* or *Fragilis* (as the case may be). For example, specific control elements may be deleted from the endogenous *Stella* and/or *Fragilis* locus so that expression is restricted to only certain tissues. Alternatively, it is possible to prepare transgenes which only contain one, some, or more, of the control elements. Transgenic animals made this way for *Stella* and/or *Fragilis* and having properties of ectopic expression, temporally or spatially, or both, will be useful for investigation of *Stella* and/or *Fragilis* gene function.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from preimplantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

We also provide non-human transgenic animals, where the transgenic animal is characterized by having an altered *Stella* and/or *Fragilis* gene, preferably as described above, as models for *Stella* or *Fragilis* function, as the case may be. Alterations to the gene include deletions or other loss of function mutations, introduction of an exogenous gene having a nucleotide sequence with targeted or random mutations, introduction of an exogenous gene from another species, or a combination thereof. The transgenic animals may be either homozygous or heterozygous for the alteration. The animals and cells derived therefrom are useful for screening biologically active agents that may modulate *Stella* and/or *Fragilis* function. The screening methods are of particular use for determining the specificity and action of potential therapies for *Stella* and/or *Fragilis* associated diseases, as described above. The animals are useful as a model to investigate the role of *Stella* and/or *Fragilis* proteins in the body.

Another aspect pertains to a transgenic animal having a functionally disrupted endogenous *Stella* or *Fragilis* gene, or both, but which also carries in its genome, and expresses, a transgene encoding a heterologous *Stella* and/or *Fragilis* protein (i.e., a *Stella* and/or *Fragilis* gene from another species). Preferably, the animal is a mouse and the heterologous *Stella* or *Fragilis* is a human *Stella* or *Fragilis*. An animal, or cell lines derived from such an animal, which has been reconstituted with human *Stella* and/or *Fragilis*, can be used to identify agents that inhibit human *Stella* and/or *Fragilis* in vivo and in vitro. For example, a stimulus that induces signalling through human *Stella* and/or *Fragilis* can be administered to the animal, or cell line, in the presence and absence of an agent to be tested and the response in the animal, or cell line, can be measured. An agent that inhibits human *Stella* and/or *Fragilis* in vivo or in vitro can be identified based upon a decreased response in the presence of the agent compared to the response in the absence of the agent.

We also provide for a *Stella* and/or *Fragilis* deficient transgenic non-human animal (a "*Stella/Fragilis* knock-out" or a "*Stella/Fragilis* null"). Such an animal is one which expresses lowered or no *Stella/Fragilis* activity, preferably as a result of an endogenous *Stella* or *Fragilis* (as the case may be) genomic sequence being disrupted or deleted. The endogenous *Stella* or *Fragilis* genomic sequence may be replaced by a null allele, which may comprise non-functional portions of the wild-type *Stella/Fragilis* sequence. For example, the endogenous *Stella/Fragilis* genomic sequence may be replaced by an allele of *Stella/Fragilis* comprising a disrupting sequence which may comprise heterologous sequences, for example, reporter sequences and/or selectable markers. Preferably, the endogenous *Stella/Fragilis* genomic sequence in a *Stella/Fragilis* knock-out mouse is replaced by an allele of *Stella* or *Fragilis* in which one or more, preferably all, of the coding sequences is replaced by such a disrupting sequence, preferably a lacZ sequence and a neomycin resistance sequence. Preferably, the genomic *Stella/Fragilis* sequence which is functionally disrupted comprises a mouse *Stella/Fragilis* genomic sequence.

Preferably, such an animal expresses no *Stella* or *Fragilis* activity, or both. More preferably, the animal expresses no activity of the *Stella* or *Fragilis* proteins shown in the sequence listings. *Stella/Fragilis* knock-outs may be generated by various means known in the art, as described in further detail below. A specific description of the construction of a *Stella* knock-out mouse is disclosed in Example 20 et seq below.

We further disclose a nucleic acid construct for functionally disrupting a *Stella/Fragilis* gene in a host cell. The nucleic acid construct comprises: a) a non-homologous replacement portion; b) a first homology region located upstream of the non-homologous replacement portion, the first homology region having a nucleotide sequence with substantial identity to a first *Stella/Fragilis* gene sequence; and c) a second homology region located downstream of the non-homologous replacement portion, the second homology region having a nucleotide sequence with substantial identity to a second *Stella/Fragilis* gene sequence, the second *Stella/Fragilis* gene sequence having a location downstream of the first *Stella/Fragilis* gene sequence in a naturally occurring endogenous *Stella/Fragilis* gene. Additionally, the first and second homology regions are of sufficient length for homologous recombination between the nucleic acid construct and an endogenous *Stella/Fragilis* gene in a host cell when the nucleic acid molecule is introduced into the host cell. In a preferred embodiment, the non-homologous replacement portion comprises an expression reporter, preferably including lacZ and a positive selection expression cassette, preferably including a neomycin phosphotransferase gene operatively linked to a regulatory element(s).

Another aspect pertains to recombinant vectors into which the nucleic acid construct described above has been incorporated. Yet another aspect pertains to host cells into which the nucleic acid construct has been introduced to thereby allow homologous recombination between the nucleic acid construct and an endogenous *Stella/Fragilis* gene of the host cell, resulting in functional disruption of the endogenous *Stella/Fragilis* gene. The host cell can be a mammalian cell that normally expresses *Stella/Fragilis* from the liver, brain, spleen or heart, or a pluripotent cell, such as a mouse embryonic stem cell. Further development of an embryonic stem cell into which the nucleic acid construct has been introduced and homologously recombined with the endogenous *Stella/Fragilis* gene produces a transgenic nonhuman animal having cells that are descendant from the embryonic stem cell and thus carry the *Stella/Fragilis* gene disruption in their genome. Animals that carry the *Stella/Fragilis* gene disruption in their germline can then be selected and bred to produce animals having the *Stella/Fragilis* gene disruption in all somatic and germ cells. Such mice can then be bred to homozygosity for the *Stella/Fragilis* gene disruption.

Detection of Pluripotent Cells in Cell Populations

Polynucleotide probes or antibodies as described here may be used for the detection of pluripotent cells such as primordial germ cells (PGCs), stem cells such as embryonic stem (ES) and embryonic germ (EG) cells in cell populations. As used herein, a "cell population" is any collection of cells which may contain one or more PGCs, ES or EG cells. Preferably, the collection of cells does not consist solely of PGCs, but comprises at least one other cell type.

Cell populations comprise embryos and embryo tissue, but also adult tissues and tissues grown in culture and cell preparations derived from any of the foregoing.

Polynucleotides as described here may be used for detection of *Fragilis* and *Stella* transcripts in PGCs or other pluripotent cells, such as ES or EG cells, by nucleic acid hybridisation techniques. Such techniques include PCR, in which primers are hybridised to *Fragilis* and/or *Stella* transcripts and used to amplify the transcripts, to provide a detectable signal; and hybridisation of labelled probes, in which probes specific for an unique sequence in the *Fragilis* and/or *Stella* transcript are used to detect the transcript in the target cells.

As noted hereinbefore, probes may be labelled with radioactive, radioopaque, fluorescent or other labels, as is known in the art.

The antibodies may also be used to detect *Fragilis* and/or *Stella*. *Fragilis*, in particular, possesses an extracellular domain which may be targeted by an anti-*Fragilis* antibody and detected at the cell surface. Alternatively, intracellular scFv may be used to detect *Fragilis* and/or *Stella* within the cell.

Particularly indicated are immunostaining and FACS techniques. Suitable fluorophores are known in the art, and include chemical fluorophores and fluorescent polypeptides, such as GFP and mutants thereof (see WO 97/28261). Chemical fluorophores may be attached to immunoglobulin molecules by incorporating binding sites therefor into the immunoglobulin molecule during the synthesis thereof.

Preferably, the fluorophore is a fluorescent protein, which is advantageously GFP or a mutant thereof GFP and its mutants may be synthesised together with the immunoglobulin or target molecule by expression therewith as a fusion polypeptide, according to methods well known in the art. For example, a transcription unit may be constructed as an in-frame fusion of the desired GFP and the immunoglobulin or target, and inserted into a vector as described above, using conventional PCR cloning and ligation techniques.

Antibodies may be labelled with any label capable of generating a signal. The signal may be any detectable signal, such as the induction of the expression of a detectable gene product. Examples of detectable gene products include bioluminescent polypeptides, such as luciferase and GFP, polypeptides detectable by specific assays, such as β-galactosidase and CAT, and polypeptides which modulate the growth characteristics of the host cell, such as enzymes required for metabolism such as HIS3, or antibiotic resistance genes such as G418. In a preferred aspect, the signal is detectable at the cell surface. For example, the signal may be a luminescent or fluorescent signal, which is detectable from outside the cell and allows cell sorting by FACS or other optical sorting techniques.

Preferred is the use of optical immunosensor technology, based on optical detection of fluorescently-labelled antibodies. Immunosensors are biochemical detectors comprising an antigen or antibody species coupled to a signal transducer which detects the binding of the complementary species (Rabbany et al., 1994 *Crit Rev Biomed Eng* 22:307-346; Morgan et al., 1996 *Clin Chem* 42:193-209). Examples of such complementary species include the antigen Zif 268 and the anti-Zif 268 antibody. Immunosensors produce a quantitative measure of the amount of antibody, antigen or hapten present in a complex sample such as serum or whole blood (Robinson 1991 *Biosens Bioelectron* 6:183-191). The sensitivity of immunosensors makes them ideal for situations requiring speed and accuracy (Rabbany et al., 1994 *Crit Rev Biomed Eng* 22:307-346).

Detection techniques employed by immunosensors include electrochemical, piezoelectric or optical detection of the immunointeraction (Ghindilis et al., 1998 *Biosens Bioelectron* 1:113-131). An indirect immunosensor uses a separate labelled species that is detected after binding by, for example, fluorescence or luminescence (Morgan et al., 1996 *Clin Chem* 42:193-209). Direct immunosensors detect the binding by a change in potential difference, current, resistance, mass, heat or optical properties (Morgan et al., 1996 *Clin Chem* 42:193-209). Indirect immunosensors may encounter fewer problems due to non-specific binding (Attridge et al., 1991 *Biosens Bioelecton* 6:201-214; Morgan et al., 1996 *Clin Chem* 42:193-209).

Prophylactic and Therapeutic Methods

We provide methods of treating an abnormal conditions related to both an excess of and insufficient amounts of *Stella* and/or *Fragilis* activity. Examples of these include the *Stella* associated diseases and *Fragilis* associated diseases disclosed above.

If the activity of *Stella* and/or *Fragilis* is in excess, several approaches are available. One approach comprises administering to a subject an inhibitor compound (antagonist) as described along with a pharmaceutically acceptable carrier in an amount effective to inhibit activation by blocking binding of a relevant molecule to the *Stella* and/or *Fragilis*, or by inhibiting a second signal, and thereby alleviating the abnormal condition.

In another approach, where *Stella* and/or *Fragilis* act by binding a ligand. soluble forms of *Stella* and/or *Fragilis* polypeptides still capable of binding the ligand in competition with endogenous *Stella* and/or *Fragilis* may be administered. Typical embodiments of such competitors comprise fragments of the *Stella* and/or *Fragilis* polypeptide.

In still another approach, expression of the gene encoding endogenous *Stella* and/or *Fragilis* can be inhibited using expression blocking techniques. Known such techniques involve the use of antisense sequences, either internally generated or separately administered. See, for example, O'Connor, *J Neurochem* (1991) 56:560 in Oligodeoxvnucleotides as Antisense Inhibitors of Gene Expression, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of *Stella* and/or *Fragilis* and its activity, several approaches are also available. One approach comprises administering to a subject a therapeutically effective amount of a compound which activates *Stella* and/or *Fragilis*, i.e., an agonist as described above, in combination with a pharmaceutically acceptable carrier, to thereby alleviate the abnormal condition. Alternatively, gene therapy may be employed to effect the endogenous production of *Stella* and/or *Fragilis* by the relevant cells in the subject.

For example, a polynucleotide as described in this document may be engineered for expression in a replication defective retroviral vector. The retroviral expression construct may then be isolated and introduced into a packaging cell transduced with a retroviral plasmid vector containing RNA encoding a *Stella* and/or *Fragilis* polypeptide such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Formulation and Administration

Peptides and polypeptides, such as the *Stella* and/or *Fragilis* peptides and polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. We further describe pharmaceutical packs and kits comprising one or more containers filled with one or more of the ingredients of the aforementioned compositions.

Polypeptides and other compounds may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localize, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1-100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Pharmaceutical Compositions

We also provide a pharmaceutical composition comprising administering a therapeutically effective amount of the polypeptide, polynucleotide, peptide, vector or antibody (such as a *Stella* and/or *Fragilis* polypeptide, etc) and optionally a pharmaceutically acceptable carrier, diluent or excipients (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition as described here may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Vaccines

Another embodiment relates to a method for inducing an immunological response in a mammal which comprises inoculating the mammal with the *Stella* and/or *Fragilis* polypeptide, or a fragment thereof, adequate to produce antibody and/or T cell immune response to protect said animal from *Stella* and/or *Fragilis* associated disease.

Yet another embodiment relates to a method of inducing immunological response in a mammal which comprises delivering a *Stella* and/or *Fragilis* polypeptide via a vector directing expression of a *Stella* and/or *Fragilis* polynucleotide in vivo in order to induce such an immunological response to produce antibody to protect said animal from diseases.

A further embodiment relates to an immunological/vaccine formulation (composition) which, when introduced into a mammalian host, induces an immunological response in that mammal to a *Stella* and/or *Fragilis* polypeptide wherein the composition comprises a *Stella* and/or *Fragilis* polypeptide or *Stella* and/or *Fragilis* gene. The vaccine formulation may further comprise a suitable carrier.

Since the *Stella* and/or *Fragilis* polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Vaccines may be prepared from one or more polypeptides or peptides as described here.

The preparation of vaccines which contain an immunogenic polypeptide(s) or peptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel are used. Only aluminum hydroxide is approved for human use.

The proportion of immunogen and adjuvant can be varied over a broad range so long as both are present in effective amounts. For example, aluminum hydroxide can be present in an amount of about 0.5% of the vaccine mixture ($Al_2O_3$ basis). Conveniently, the vaccines are formulated to contain a final concentration of immunogen in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The polypeptides described here may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The pharmaceutical and vaccine compositions as disclosed here may be administered by direct injection. The composition may be formulated for parenteral, mucosal, intramuscular, intravenous, subcutaneous, intraocular or transdermal administration. Typically, each protein may be administered at a dose of from 0.01 to 30 mg/kg body weight, preferably from 0.1 to 10 mg/kg, more preferably from 0.1 to 1 mg/kg body weight.

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

The term "co-administered" means that the site and time of administration of each of for example, the polypeptide and an additional entity such as adjuvant are such that the necessary modulation of the immune system is achieved. Thus, whilst the polypeptide and the adjuvant may be administered at the same moment in time and at the same site, there may be advantages in administering the polypeptide at a different time and to a different site from the adjuvant. The polypeptide and adjuvant may even be delivered in the same delivery vehicle—and the polypeptide and the antigen may be coupled and/or uncoupled and/or genetically coupled and/or uncoupled.

The *Stella* and/or *Fragilis* polypeptide, polynucleotide, peptide, nucleotide, antibody etc and optionally an adjuvant may be administered separately or co-administered to the host subject as a single dose or in multiple doses.

The vaccine composition and pharmaceutical compositions described here may be administered by a number of different routes such as injection (which includes parenteral, subcutaneous and intramuscular injection) intranasal, mucosal, oral, intra-vaginal, urethral or ocular administration.

The vaccines and pharmaceutical compositions described here may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, may be 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Diagnostic Assays

We describe the use of *Stella* and/or *Fragilis* polynucleotides and polypeptides (as well as homologues, variants and derivatives thereof) for use in diagnosis as diagnostic reagents or in genetic analysis. Nucleic acids complementary to or capable of hybridising to *Stella* and/or *Fragilis* nucleic acids (including homologues, variants and derivatives), as well as antibodies against *Stella* and/or *Fragilis* polypeptides are also useful in such assays.

We provide for a natural variant of *Stella* and/or *Fragilis* polypeptide or nucleic acid, and the use of such a natural variant in diagnosis of *Stella* and/or *Fragilis* associated disease. *Stella* and/or *Fragilis* polymorphisms may include differences at the nucleic acid level, which may or may not reflect differences in the amino acid level. Preferably, such *Stella* and/or *Fragilis* variants or mutants are such that they include changes in the amino acid level. However, we also disclose *Stella* and/or *Fragilis* polymorphisms which occur in non-coding regions, for example, expression control regions such as promoters and enhancers.

Polymorphisms in *Stella* and/or *Fragilis* include deletions of one or more nucleic acids, insertions of one or more nucleic acids, inversions, etc. Preferably, *Stella* and/or *Fragilis* polymorphisms comprise single nucleotide polymorphisms.

Polymorphisms in *Stella* and/or *Fragilis* may be identified by comparing sequences at the appropriate level (whether nucleic acid or protein) between individuals in a population. Differences in sequences may be reflected in different physical properties, and techniques for detecting these may rely on detection of changes in physical properties. For example, single nucleotide polymorphisms may be detected as restriction fragment length polymorphisms (i.e., difference in susceptibility to digestion by a restriction enzyme). Furthermore, SNPS may affect the migration or mobility of a nucleic acid fragment or protein fragment in a gel.

Non-coding polymorphisms in *Stella* and/or *Fragilis* may be identified by sequencing non-coding regions of *Stella* and/or *Fragilis*. For example, control regions of the *Stella* and/or *Fragilis* gene, such as enhancers and promoters may be sequenced to identify polymorphisms. The effect of such non-coding polymorphisms on the expression level of *Stella* and/or *Fragilis* may be determined by constructing transgenic mice (as described below) comprising the mutant *Stella* and/or *Fragilis* sequences, or by generating expression constructs and transfection into cell lines. In each case, the expression level of *Stella* and/or *Fragilis* is detected, by RT-PCR or antibody Western staining, to determine the effect of the mutation in the control of expression of *Stella* and/or *Fragilis*. Useful *Stella* and/or *Fragilis* polymorphisms are those which modulate the level of expression, wiether by up-regulation or down-regulation of *Stella* and/or *Fragilis* levels.

Accordingly, we provide for a variant or mutant or polymorphism in a non-coding region of *Stella* and/or *Fragilis*, preferably in a control region of *Stella* and/or *Fragilis*, preferably in a promoter and/or enhancer of *Stella* and/or *Fragilis*, which is capable of modulating the level of expression of *Stella* and/or *Fragilis* in an organism. We also provide for a set of two or more of such mutants or variants or polymorphisms, preferably non-coding polymorphisms. We also provide for the use of such variants or polymorphisms or sets of variants to identify nucleic acid and/or amino acid positions, in which changes to such positions affect the level of expression of *Stella* and/or *Fragilis*. We also provide for a transgenic animal comprising a variant or mutant or polymorphism of *Stella* and/or *Fragilis*, preferably, a non-coding polymorphism.

Detection of a mutated form of the *Stella* and/or *Fragilis* gene associated with a dysfunction will provide a diagnostic tool that can add to or define a diagnosis of a disease or susceptibility to a disease which results from under-expression, over-expression or altered expression of *Stella* and/or *Fragilis*. Individuals carrying mutations in the *Stella* and/or *Fragilis* gene (including control sequences) may be detected at the DNA level by a variety of techniques.

For example, DNA may be isolated from a patient and the DNA polymorphism pattern of *Stella* and/or *Fragilis* determined. The identified pattern is compared to controls of patients known to be suffering from a disease associated with over-, under- or abnormal expression of *Stella* and/or *Fragilis*. Patients expressing a genetic polymorphism pattern associated with *Stella* and/or *Fragilis* associated disease may then be identified. Genetic analysis of the *Stella* and/or *Fragilis* gene may be conducted by any technique known in the art. For example, individuals may be screened by determining DNA sequence of a *Stella* and/or *Fragilis* allele, by RFLP or SNP analysis, etc. Patients may be identified as having a genetic predisposition for a disease associated with the over-, under-, or abnormal expression of *Stella* and/or *Fragilis* by detecting the presence of a DNA polymorphism in the gene sequence for *Stella* and/or *Fragilis* or any sequence controlling its expression.

Patients so identified can then be treated to prevent the occurrence of *Stella* and/or *Fragilis* associated disease, or more aggressively in the early stages of *Stella* and/or *Fragilis* associated disease to prevent the further occurrence or development of the disease. *Stella* and/or *Fragilis* associated diseases include any cancer, for example, as described above.

We further disclose a kit for the identification of a patient's genetic polymorphism pattern associated with *Stella* and/or *Fragilis* associated disease. The kit includes DNA sample collecting means and means for determining a genetic polymorphism pattern, which is then compared to control samples to determine a patient's susceptibility to *Stella* and/or *Fragilis* associated disease. Kits for diagnosis of a *Stella* and/or *Fragilis* associated disease comprising *Stella* and/or *Fragilis* polypeptide and/or an antibody against such a polypeptide (or fragment of it) are also provided.

Nucleic acids for diagnosis may be obtained from a subject's cells, such as from blood, urine, saliva, tissue biopsy or autopsy material. In a preferred embodiment, the DNA is obtained from blood cells obtained from a finger prick of the patient with the blood collected on absorbent paper. In a further preferred embodiment, the blood is collected on an AmpliCard.TM. (university of Sheffield, Department of Medicine and Pharmacology, Royal Hallamshire Hospital, Sheffield, England S10 2JF).

The DNA may be used directly for detection or may be amplified enzymatically by using PCR or other amplification techniques prior to analysis. Oligonucleotide DNA primers that target the specific polymorphic DNA region within the genes of interest may be prepared so that in the PCR reaction amplification of the target sequences is achieved. RNA or cDNA may also be used as templates in similar fashion. The amplified DNA sequences from the template DNA may then be analyzed using restriction enzymes to determine the genetic polymorphisms present in the amplified sequences and thereby provide a genetic polymorphism profile of the patient. Restriction fragments lengths may be identified by gel analysis. Alternatively, or in conjunction, techniques such as SNP (single nucleotide polymorphisms) analysis may be employed.

Deletions and insertions can be detected by a change in size of the amplified product in comparison to the normal genotype. Point mutations can be identified by hybridizing amplified DNA to labeled *Stella* and/or *Fragilis* nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, eg., Myers et al, *Science* (1985)230:1242. Sequence changes at specific locations may also be revealed by nuclease protection assays, such as RNase and S protection or the chemical cleavage method. See Cotton et al., *Proc Natl Acad Sci USA* (1985) 85: 4397-4401. In another embodiment, an array of oligonucleotides probes comprising the *Stella* and/or *Fragilis* nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610-613 (1996)).

Single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat Res 285:125-144; and Hayashi (1992) Genet Anal Tech Appl 9:73-79). Single-stranded DNA fragments of sample and control *Stella* and/or *Fragilis* nucleic acids may be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

The diagnostic assays offer a process for diagnosing or determining a susceptibility to *Stella* and/or *Fragilis* associated diseases, for example, as described above.

The presence of *Stella* and/or *Fragilis* polypeptides and nucleic acids may be detected in a sample. Thus, infections and diseases as listed above can be diagnosed by methods comprising determining from a sample derived from a subject an abnormally decreased or increased level of the *Stella* and/or *Fragilis* polypeptide or *Stella* and/or *Fragilis* mRNA. The sample may comprise a cell or tissue sample from an organism suffering or suspected to be suffering from a disease associated with increased, reduced or otherwise abnormal *Stella* and/or *Fragilis* expression, including spatial or temporal changes in level or pattern of expression. The level or pattern of expression of *Stella* and/or *Fragilis* in an organism suffering from or suspected to be suffering from such a disease may be usefully compared with the level or pattern of expression in a normal organism as a means of diagnosis of disease.

In general therefore, we describe a method of detecting the presence of a nucleic acid comprising a *Stella* and/or *Fragilis* nucleic acid in a sample, by contacting the sample with at least one nucleic acid probe which is specific for said nucleic acid and monitoring said sample for the presence of the nucleic acid. For example, the nucleic acid probe may specifically bind to the *Stella* and/or *Fragilis* nucleic acid, or a portion of it, and binding between the two detected; the presence of the complex itself may also be detected. Furthermore, we disclose a method of detecting the presence of a *Stella* and/or *Fragilis* polypeptide by contacting a cell sample with an antibody capable of binding the polypeptide and monitoring said sample for the presence of the polypeptide. This may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as a *Stella* and/or *Fragilis*, in a sample derived from a host are well-known to those of skill in the art. Such assay methods include radioimmunoassays, competitive-binding assays, Western Blot analysis and ELISA assays.

We also describe a diagnostic kit for a disease or susceptibility to a *Stella* and/or *Fragilis* associated disease (including an infection). The diagnostic kit comprises a *Stella* and/or *Fragilis* polynucleotide or a fragment thereof; a complementary nucleotide sequence; a *Stella* and/or *Fragilis* polypeptide or a fragment thereof, or an antibody to a *Stella* and/or *Fragilis* polypeptide.

Further Aspects of the Invention

We provide a nucleic acid molecule which is at least 90% homologous to SEQ ID NO: 3 and a nucleic acid molecule which is at least 75% homologous to SEQ ID NO: No. 5.

We disclose polynucleotides which comprise a contiguous stretch of nucleotides from SEQ ID NO: 3 or SEQ ID NO: 5, or any of SEQ ID NOs: 7, 9, 11, 13, 15 and 17, or of a sequence at least 90% homologous thereto. Advantageously, this stretch of contiguous nucleotides is 50 nucleotides in length, preferably 40, 35, 30, 25, 20, 15 or 10 nucleotides in length.

The human genes *Fragilis* and *Stella* encode novel polypeptides, the sequences of which are set forth in SEQ ID NO: 4 and SEQ ID NO: 6. Other *Fragilis* genes are set out in SEQ ID NOs: 8, 10, 12, 14, 16 and 18. We therefore disclose polypeptides encoded by the nucleic acids described here, as well as nucleic acids encoding any of the polypeptides disclosed here. Preferably, the polypeptides have the sequences set forth in SEQ ID NO: 4 and SEQ ID NO: 6.

EXAMPLES

The following Examples 1 to 9 relate to cloning and characterisation of rodent *Fragilis* and *Stella* genes, and are included here for reference.

Example 1

Identification of Murine Genes Specific to the Earliest Population of Primordial Germ Cells (PGCs) by Single Cell cDNA Differential Screening A method for single cell analysis is developed to identify genes that are involved in the specification of the germ cell lineage, which results in the establishment of a founder population of Primordial Germ Cells (PGCs). It is determined that the lineage specification of PGCs accompanies the expression of a unique set of genes, which are not expressed in somatic cells.

The method for the identification of the genes is mainly based on the differential screening of the libraries made from single cells from day 7.25 mouse embryonic fragments that contain PGCs. The single cell cDNA differential screen was originally described by Brady and Iscove (1993), and subsequently modified by Cathaline Dulac and Richard Axel which resulted in the successful identification of the pheromone receptor genes from rat (Dulac, C. and Axel, 1995). The method of Axel's group is employed, with slight modifications as described.

Construction of Single Cell cDNAs from Embryonic Fragment Bearing the Earliest Population of PGCs In the mouse, the earliest population of the PGCs is reported to consist of alkaline phosphatase positive cluster of some 40 cells, at the base of the emerging allantois at day 7.25 of gestation (Ginsburg, M., Snow, M. H. L., and McLaren, A. (1990)). The precise location of the PGC cluster in the inbred 129Sv and C57BL/6 strain is determined by microscopy using both whole-mount alkaline phosphatase staining and semi-thin sections stained by methylene blue. The earliest stage at which a cluster of PGCs can be detected is at the Late Streak stage (Downs, K. M., and Davies, T. (1993)), when a distinctively stained population of cells is found just beneath an epithelial lining from which the allantoic bud appears. This region is at the border between the extraembryonic and embryonic tissues just posterior to and above the most proximal part of the primitive streak. The cluster persists at this position at least until Early/Mid Bud stage. In the inbred 129Sv strain, the PGC cluster is found to contain a slightly larger number of the cells, which are more tightly packaged than in the C57BL/6 strain. The 129Sv strain is used for subsequent experiments, as a better recovery of the earliest PGCs is obtained.

129Sv embryos are isolated at E7.5 in DMEM plus 10% FCS buffered with 25 mM HEPES at room temperature and the developmental stage of each embryo is determined under a dissection microscope. The precise developmental stage can differ substantially even amongst embryos within the same litter. Embryos that are at the no bud or early bud (allantoic) stage are chosen for further dissection, which in part is dictated by the ease of identification of the region containing PGCs as seen under the dissection microscope. The fragment that is expected to contain the PGC cluster is cut out very precisely by means of solid glass needles. This region is dissociated it into single cells using 0.25% trypsin-ImM EGTA/PBS treatment at 37° C. for 10 min, followed by gentle pipetting with a mouth pipette. The dissected fragment usually contained between 250-300 cells. The procedure for cell dispersal with this gentle procedure left the visceral endoderm layer remained as an intact cellular sheet.

We picked single cells randomly from the cell suspension by a mouth pipette and put individual single cells (but avoiding generating air bubbles), into a thin-walled PCR tube containing 4 μl of ice-cold cell lysis buffer (50 mM Tris-HCl pH8.3, 75 mM KCl, 3 mM $MgCl_2$, 0.5% NP40, containing 80 ng/ml pd(T)24, 5 μg/ml prime RNase inhibitor, 324 U/ml RNA guard, and 10 mM each of dATP, dCTP, dGTP, and dTTP). The volume of medium carried with the single cell is less than 0.5 μl. The tube is briefly centrifuged to ensure that the cell is indeed in the lysis buffer. During each separate experiment, we picked a total of 19 single cells, and left one tube without a cell, to serve as a negative control for the PCR amplification procedure. All the cells that are collected in tubes are kept on ice before starting the subsequent procedure.

The cells are lysed by incubating the tubes at 65° C. for 1 min, and then kept at room temperature for 1-2 min to allow the oligo dT to anneal the to RNA. First-strand cDNA synthesis is initiated by adding 50 U of Moloney murine leukaemia virus (MMLV) and 0.5 U of avian myeloblastosis virus (AMV) reverse transcriptase followed by incubation for 15 min at 37° C. The reverse transcriptases are inactivated for 10 min at 65° C. This reverse transcription reaction is restricted to 15 min, which allows the synthesis of relatively uniform size cDNAs of between 500 base-1000 bases in length from the C termini. This enables the subsequent PCR amplification to be fairly representative.

Next, in order to add the poly A tail to the 5 prime end of the synthesised first-strand cDNA, 4.5 μl of 2×tailing buffer (200 mM potassium cacodylate pH7.2, 4 mM $CoCl_2$, 0.4 mM DTT, 200 mM dATP containing 10 U of terminal transferase) is added to the reaction followed by incubation for 15 min at 37° C. The samples are heat inactivated for 10 min at 65° C. The reaction now contained synthesised cDNAs bearing poly T tail at their C termini and poly A stretch at their N termini, ready for the amplification by the PCR using the specific primer.

The contents of each tube is brought to 100 μl with a solution made of 10 mM Tris-HCl pH8.3, 50 mM KCl, 2.5 mM $MgCl_2$, 100 μg/ml bovine serum albumin, 0.05% Triton-×100, 1 mM of dATP, dCTP, dGTP, dTTP, 10 U of Taq polymerase, and 5 µg of the AL1 primer. The AL1 sequence is ATT GGA TCC AGG CCG CTC TGG ACA AAA TAT GAA TCC $(T)_{24}$. The PCR amplification is performed according to the following schedule: 94° C. for 1 min, 42° C. for 2 min, and 72° C. for 6 min with 10 s extension per cycle for 25 cycles. Five additional units of Taq polymerase are added before performing 25 more cycles with the same programme but without the extension time. Each tube at this point contains amplified cDNA products derived from a single cell. The protein contents of the solution are extracted by phenol/chloroform treatment, and the amplified cDNAs are precipitated by ethanol and eventually suspended in 100 µl of TE pH8.0. 5 µl of the cDNA solution is run on a 1.5% agarose gel to check the success of the amplification. Most of the samples show a very intense 'smeared' band ranging mainly between 500 bp to 1200 bp, indicating the efficient amplification of the single cell cDNA. Only the successfully amplified samples are used for the subsequent 'cell typing' analysis.

Example 2

Identification of PGCs by Examination of the Expression of Marker Genes

The embryonic fragment which is excised theoretically contains three major components: the allantoic mesoderm, PGCs, and extraembryonic mesoderm surrounding PGCs. In order to identify the single cell cDNA of PGC origin amongst these samples, positive and negative selection of the constructed cDNAs is performed, by examining the expression of four marker genes (BMP4, TNAP, Hoxb1, and Oct4), which are known to be either expressed or repressed in various cell types in this region.

At the No/Early Bud stage, BMP4 is reported to be expressed in the emerging allantois and mesodermal components of the developing amnion, chorion, and visceral yolk sac (Lawson, K. A., Dunn, N. R., Roelen, B. A. J., Zeinstra, L. M., Davis, A. M., Wright, C. V. E., Korving, J. P. W. F. M., and Hogan, B. L. M. (1999)). The boundary of BMP4 expression is very sharp, and the expression is completely excluded in the mesodermal region beneath the epithelial lining continuous from the amnionic mesoderm where the putative PGCs are determined. Therefore, BMP4 is used as a negative marker for the selection. Primer pairs are designed for amplifying the C terminal portion of BMP4 (5': GCC ATA CCT TGA CCC GCA GAA G, 3': AAA TGG CAC TCA GTT CAG TGG G). The PCR amplification is performed using 0.5 µl of the cDNA solution as a template according to the following schedule: 95° C. for 1 min, 55° C. for 1 min, and 72° C. for 1 min for 20 cycles. Among 83 samples tested, 57 samples show the expected size of bands, indicating expression of BMP4 these single cells. These samples are considered to be of allantoic mesodermal origin, and therefore excluded from amongst the candidates representing cells of PGC origin.

The expression of tissue non-specific alkaline phosphatase (TNAP), which has long been used as an early marker for PGCs (Ginsburg, M., Snow, M. H. L., and McLaren, A. (1990)), is then examined. Primer pairs are designed (5': CCC AAA GCA CCT TAT TTT TCT ACC, 3': TTG GCG AGT CTC TGC AAT TGG) and the same PCR reaction as above is performed. Amongst the 26 samples, 22 samples are judged to be positive for TNAP. From the alkaline phosphatase staining of the sectioned embryos, it is known that the somatic cells surrounding PGCs also express some amount of TNAP, although the level of expression is slightly lower than that in PGCs. Therefore, amongst these 22 positive samples there should be still be cells destined to become somatic cells as well as PGCs.

One of the genes known to be expressed in the totipotent PGCs but not in somatic cells is Oct4 (Yoem, Y. II., Fuhrmann, G., Ovitt, C. E., Brehm, A., Ohbo, K., Gross, M., Hubner, K., and Scholer, H. R. (1996)). To examine the possibility that Oct4 can be used as a marker to distinguish PGCs from somatic cells at this stage, Oct4 expression is checked in the 22 samples by PCR (5': CAC TCT ACT CAG TCC CTT TTC, 3': TGT GTC CCA GTC TTT ATT TAA G). All the 22 samples express Oct4 at comparable levels, indicating that the somatic cells at this stage are still actively transcribing Oct4 RNA.

The amount of expression of TNAP is quantitated in 22 samples by Southern blot analysis (reverse northern blot analysis). Given the fairly representative amplification of the single cell method, confirmed by amplifying single ES cell cDNA, Southern blot analysis allows semi-quantitative measurement of the amount of the genes expressed in the original single cells, although it does not serve as a perfect indicator of cell identity. However, as a result of this TNAP analysis, 10 samples out of 22 show relatively stronger bands at an equivalent level, while the remaining 12 samples exhibit weaker signals. These results indicate that these 22 samples can be divided at least into two groups, one with stronger TNAP expression (therefore from putative PGCs) and the other with weaker TNAP.

The possibility that somatic cells surrounding PGCs start to express Hoxb1, while PGCs do not (personal communication from Dr. Kirstie Lawson) is also examined. Primer pairs are designed (5': AAC TCA TCA GAG GTC GAA GGA, 3': CGG TGC TAT TGT AAG GTC TGC) and the same PCR reaction as above is performed. Among the 22 samples tested, 12 are positive, and more importantly, these 12 samples perfectly match the ones which show weaker TNAP signals, by Southern blot analysis.

Taking all these results into consideration, it is concluded that 10 samples out of 83, which are Oct4 (+), TNAP (++), BMP4 (−), and Hoxb1 (−), are of PGC origin. This ratio (10/83) is reasonable, considering the number of the founding population of PGCs as 40 and the number of cells in the fragment as 250-300.

Example 3

Differential Screening of Single Cell cDNA Libraries

As the efficiency of the amplification of cDNA differs in each tube, it is very important to select the samples with the most efficiently amplified cDNA for the construction of libraries. The amplification of six different genes (ribosomal protein S12, intermediate filament protein vimentin, β tubulin-5, α actin, Oct4, E-cadherin) is examined in the 10 PGC candidate samples, by Southern blot analysis. Judging from the overall profile of the amplification of all these six genes, three cDNA preparations are selected for the construction of libraries.

To obtain the maximum amount of double strand cDNA, an extension step is performed with 5 µl of cell cDNA in 100 µl of the PCR buffer described as above (including 1 µl of Amplitaq) according to the following schedule: 94° C. for 5min, 42° C. for 5 min, 72° C. for 30 min. The solution is extracted by phenol/chloroform treatment, and the amplified cDNAs are precipitated by ethanol, suspended in TE, and completely digested with EcoRI. The PCR primer and excess amount of dNTPs are removed by QIAGEN PCR Purification Kit, and all the purified cDNAs are run on a 2% low melting agarose gel. cDNAs above 500 bp are cut and purified by QIAGEN Gel Purification Kit. The purified cDNAs are precipitated by ethanol and suspended in TE and ligated into λ ZAP II vector arms. The ligated vector is packaged, titered and the ratio of the successfully ligated clones is monitored by amplifying the inserts with T3 and T7 primers from 20 plaques. More than 95% of the phage are found to contain inserts.

The representation of the three genes, ribosomal protein S12, β tubulin-5, Oct4, is quantitated by screening 5000 plaques, and the library of the best quality among the three (S12 0.62%, β tubulin 0.4%, Oct4 0.5%) is used for the differential screening. As a comparison partner with the PGC probe, one of the most efficiently amplified surrounding somatic cell cDNA (Oct4 (+), TNAP(+/−), BMP(−), and Hoxb1(+)) is selected by the similar Southern blot analysis.

The library is plated at a density of 1000 plaques per 15 cm dish to obtain large plaques (2 mm diameter) and two duplicate lifts are taken using Hybond N+ filters from Amersham. The filters are prehybridized at 65° C. in 0.5M sodium phosphate buffer (pH7.3) containing 1% bovine serum albumin and 4% SDS. We prepared the cell cDNA probes by reamplifying for 10 cycles 1 μl of the original cell cDNA into 50 μl of total reaction with the AL1 primer, in the absence of cold dCTP and with 100 μCi of newly received $^{32}$PdCTP, followed by the purification using Amersham Nick™ Spin Column. The filters are hybridised for at least 16 hrs with $1.0 \times 10^7$ cpm/ml (The first filter is hybridised with somatic cell probe and the second filter is hybridised with the PGC probe). After the hybridisation, the filters are washed three times at 65° C. in 0.5×SSC, 0.5% SDS and exposed to X ray films until the appropriate signal is obtained (usually one to two days).

The positive plaques in the two duplicate filters are compared very carefully. Among 5000 plaques screened, 280 are picked as candidates representing the differentially expressed genes. The inserts of all the 280 plaques are amplified with T3 and T7 primers, run on 1.5% gels, and double sandwich Southern blotted. Each membrane is hybridised with the PGC and somatic cell probe, respectively, using the same conditions as the screening. 38 clones amongst the 280 are selected as differentially expressed genes. These clones are next hybridised with the second PGC and somatic cell cDNA probes, which resulted in 20 clones out of 38 to be common in both PGC cDNAs but they are either not included or less abundant in both somatic cell cDNAs. The sequences of all the 20 clones are determined.

Genes Highly Specific to the Earliest Population of PGCs

The 20 clones represent 11 different genes (two clones appear two times, one clone appears three times, and one clone appears 6 times). To further stringently check the specificity of expression, primer pairs are designed for these 11 clones and their expression checked in 10 different single PGC-candidate cDNAs and 10 different single somatic cell cDNAs by PCR. Two of them show highly specific expression to PGC cDNAs.

The first gene, *Fragilis* (Germ cell restricted-1, *Fragilis*), encodes a 137 amino acid protein with a predicted molecular weight of 15.0 kD. The nucleic acid sequence of mouse *Fragilis* is set out in SEQ ID NO: 2.

*Fragilis*, comprises two transmembrane domains, the amino and carboxy terminus ends being located outside the cell. *Fragilis* is a newly discovered member of the interferon (IFN)-inducible transmembrane protein family (Deblandre, G. A. et al. Expression cloning of an interferon-inducible 17-kDa membrane protein implicated in the control of cell growth. J. Biol. Chem. 270, 23860-23866 (1995); Friedman, R. L., Manly, S. P., McMahon, M., Kerr, I. M. & Stark, G. R. Transcriptional and posttranscriptional regulation of interferon-induced gene expression in human cells. Cell 38, 745-755 (1984) and is detected in expressed sequence tags (ESTs) derived from many different embryonic and adult tissues, suggesting that it may have a common role in different developmental contexts. One prototype member is the IFN-inducible human 9-27 (identical to the Leu-13 antigen) protein in leukocytes and endothelial cells, a cell surface component of a multimeric complex involved in homotypic adhesion and transduction of antiproliferative signals (Deblandre, G. A. et al. Expression cloning of an interferon-inducible 17-kDa membrane protein implicated in the control of cell growth. J. Biol. Chem. 270, 23860-23866 (1995); Evans, S. S., Collea, R. P., Leasure, J. A. & Lee, D. B. IFN-a induces homotypic adhesion and Leu-13 expression in human B lymphoid cells. J. Immunol. 150, 736-747 (1993); Evans, S. S., Lee, D. B., Han, T., Tomasi, T. B. & Evans, R. L. Monoclonal antibody to the interferoninducible protein Leu-13 triggers aggregation and inhibits proliferation of leukemic B cells. Blood 76, 2583-2593 (1990)).

One prototype *Fragilis* family member, human 9-27 (identical to Leu-13 antigen), is inducible by interferon in leukocytes and endothelial cells, and is located at the cell surface as a component of a multimeric complex involved in the transduction of antiproliferative and homotypic adhesion signals (Deblandre, 1995).

The BLASTN search revealed that the *Fragilis* sequence was found in ESTs derived from many different tissues both from embryos and adults, indicating that *Fragilis* may play a common role in different developmental and cell biological contexts. Database searches reveal a sequence match with the rat interferon-inducible protein. (sp:INIB RAT, pir:JC1241) with unknown function. The *Fragilis* sequence appears six times in our screen, indicating high level expression in PGCs.

The second gene, *Stella*, encodes a 150 amino acid protein, of 18 kD. The nucleic acid sequence of mouse *Stella* is set out in SEQ ID NO: 1.

It has no sequence homology with any known protein, contains several nuclear localisation consensus sequences and is highly basic pI (pI=9.67, the content of basic residues=23.3%), indicating a possible affinity to DNA. Furthermore a potential nuclear export signal was identified, indicating that *Stella* may shuttle between the nucleus and the cytoplasm. BLASTN analysis revealed that the *Stella* sequence was found only in the preimplantation embryo and germ line (newborn ovary, female 12.5 mesonephros and gonad etc.) ESTs indicating its predominant expression in totipotent and pluripotent cells. Interestingly, we found that *Stella* contains in its N terminus a modular domain which has some sequence similarity with the SAP motif. This motif is a putative DNA-binding domain involved in chromosomal organisation. There is also apparently a splicing factor motif-like structure in its C terminus. These findings suggest a possible involvement of *Stella* in chromosomal organization and RNA processing.

Example 4

Identification of PGCs by Screening for *Fragilis* and *Stella* Expression

Although PGCs are identified in Example 2 by analysis of BMP4, TNAP, Hoxb1, and Oct4, no single one of these genes can be taken as a marker for the PGC state. However, both *Fragilis* and *Stella* may be used as such.

The expression of *Fragilis* is examined. Primer pairs are designed (5': CTACTCCGTGAAGTCTAGG, 3': AATGAGTGTTACACCTGCGTG) and the same PCR reaction as above is performed. *Fragilis* expression was detected in germ cell competent cells. The definitive PGCs were recruited from amongst this group of cells showing expression of *Fragilis*.

The boundary of *Stella* expression in particular is well-defined, and the expression is substantially limited to PGCs. Therefore, *Stella* is used as a positive marker for the selection of PGCs. Primer pairs are designed for amplifying the C terminal portion of *Stella* (5': GCCATTCAGATGTCTCTGCAC, 3': CTCACAGCTTGAGGCTTCTAA). The PCR amplification is performed using 0.5 µl of the cDNA solution obtained from PGCs in Example 1 as a template according to the following schedule: 95° C. for 1 min, 55° C. for 1 min, and 72° C. for 1 min for 20 cycles. Among 83 samples tested, only those taken from PGCs show expression of *Stella* Hence, *Stella* is a positive marker for the PGC fate.

Antibodies against *Fragilis* and *Stella* can be similarly used to detect pluripotent cells. Preferably, antibodies against *Fragilis* are used to detect germ cell competent cells, and antibodies against *Stella* are used to detect PGCs.

Accordingly, both *Fragilis* and *Stella* are positive markers for the PGC fate which can be used to positively identify PGC.

Identification of PGC by ISH

The in vivo expression of the two genes is examined by in situ hybridisation. The expression of *Fragilis* starts very weakly in the entire epiblast at E6.0-E6.5 (PreStreak stage) and becomes strong in the few cell layers of the proximal rim of the epiblast. BMP4 that is expressed in the extraembryonic ectoderm is one signalling molecule that is important for the induction of germ cell competence and expression of *Fragilis*. Other signals, such as interferons are likely to be involved in the induction of *Fragilis*. The expression becomes more intense at the proximo-posterior end of the developing primitive streak at the Early/Mid Streak stage and becomes very strong at this position from Late Streak stage onward. The expression persists until Early Head Fold stage and eventually disappears gradually. No expression is detected in the migrating PGCs at E8.5.

The expression of *Stella* starts at the proximo-posterior end of the developing primitive streak at Mid/Late Streak stage and becomes gradually strong at the same position from the later stage onward. The expression is specific and individual single cells stained in a dotted manner can be seen in the region where PGCs are considered to start differentiating as a cluster of cells. At Late Bud/Early Head Fold stage, some cells considered to be migrating from the initial cluster are stained as well as cells in the cluster. At E8.5 and E9.5, a group of cells considered to be the migrating PGCs are very specifically stained.

From these results, it is concluded that *Fragilis* is a gene which is upregulated during the process of lineage specification and germ cell competence, and subsequently of PGCs, when *Stella* is turned on after *Fragilis* to fix the PGC fate.

Accordingly, expression of *Fragilis* may be detected in a method of detecting lineage specification, and/or pluripotency, such as germ cell competence. Similarly, expression of *Stella* may be detected to detect commitment to cell fate, for example, commitment to fate as a primordial germ cell.

Example 5

Expression of *Fragilis* and *Stella* During Germ Line Development

Antibodies against *Stella* and *Fragilis* are used to detect expression of these genes in early embryos. It is found that each of these genes is expressed in primordial germ cells. In particular, we find that *Fragilis* is the first gene to mark PGC competent cells at the time of germ cell allocation. *Stella* is expressed only in the lineage-restricted founder PGCs and thereafter in the germ cell lineage.

FIG. 3 shows expression of mouse *Fragilis* in embryonic stem (ES) cells.

*Fragilis* is expressed in pluripotent ES and EG cells. During the derivation of EG cells from PGCs, it is found that *Fragilis* expression re-appears on EG cells. Late PGCs are negative for *Fragilis* after specification of these cells is completed.

Figure 5:
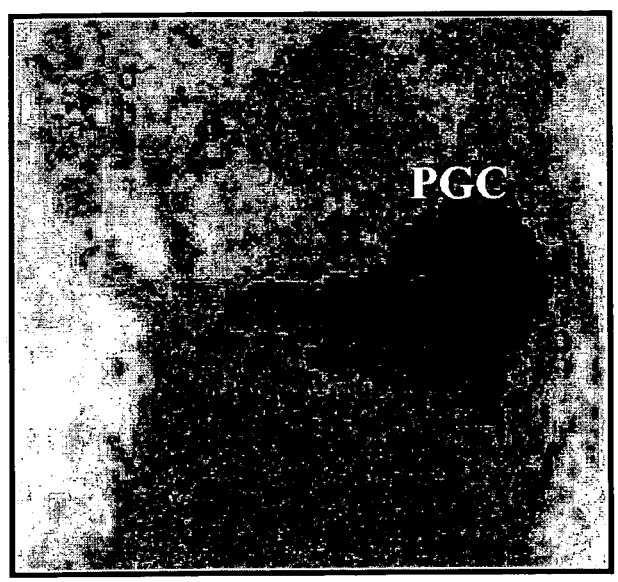
FIG. 5. Mouse Fragilis expression by whole-mount in situ hybridization in E7.2 mouse embryos.

FIG. 5 shows expression of mouse *Fragilis* as detected by whole-mount in situ hybridization in E7.2 mouse embryos.

There is strong *Fragilis* expression at the base of incipient allantois where the founder PGC population differentiates in the E7.25 embryos. *Fragilis* expression persisted until E7.5, but it was not detected in migrating PGCs at E8.5. *Fragilis* is first detected in germ cell competent proximal epiblast cells. *Fragilis* expression can be induced in the epiblast cells when combined with the tissues extraembryonic ectoderm tissues, which is the source of BMP4. In the BMP4 mutant mice, there is no expression of *Fragilis*, consistent with the absence of PGCs in these embryos (Lawson et al., 1999).

FIG. 4 shows expression of mouse *Stella* in PGCs.

Figure 7:
FIG. 7. Mouse Stella expression in PGCs in the process of migration into the gonads in E9.0 embryos.

*Stella* expression which is strong in PGCs is downregulated in EG cells. There is also low level expression of *Stella* in ES cells. *Stella* and *Fragilis* are detectable in ES and EG cells by Northern blot analysis. *Stella* is first detected at E7.0 in single cells within the distinctive cluster of lineage-restricted PGCs, and thereafter in migrating PGCs and subsequently when they enter the gonads. FIG. 7 shows *Stella* expression in PGCs in the process of migration into the gonads in E9.0 embryos. *Stella* is the only gene so far known to be a definitive marker for the founder population of PGCs.

Figure 6:
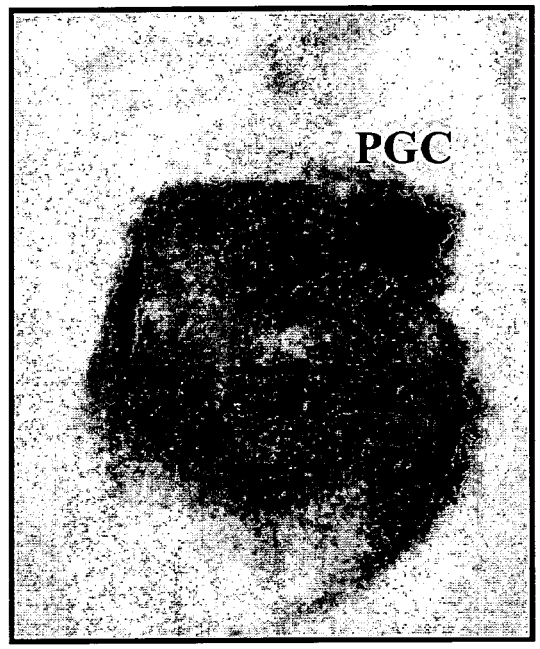
FIG. 6. Mouse Stella expression by whole mount in situ hybridisation in E7.2 mouse embryos.

FIG. 6 shows expression of mouse *Stella* as detected by whole-mount in situ hybridization in E7.2 mouse embryos.

FIG. 8. Expression of mouse *Fragilis* and *Stella* in single cells detected by PCR analysis of single cell cDNAs. Note that there are more single cells showing expression of *Fragilis* compared to those showing expression of *Stella*. Only cells with the highest levels of *Fragilis* expression are found to express *Stella* and acquire the germ cell fate. Cells that express *Stella* were found not to show expression of Hoxb1. Cells that express lower levels of *Fragilis* and no *Stella* become somatic cells and show expression of Hoxb1. The founder population of PGCs also show high levels of Tnap. Both the founder PGCs and the somatic cells show expression of Oct4, T(Brachyury), and Fgf8.

Example 6

Expression of *Fragilis* and *Stella* in Individual Cells

Intracellular localisation of *Stella* and *Fragilis* is also determined. *Fragilis* localised to a single cytoplasmic spot at the Golgi apparatus, as well as in the plasma membrane. *Stella* comprises a putative nuclear localisation signal and nuclear export signal, and is localised in both the cytoplasm and nucleus.

*Fragilis* is observed in the Golgi apparatus as well as in the plasma membrane of PGCs. The cell surface localization of *Fragilis* is expected as a member of the interferon inducible gene family [Deblandre, 1995]. Expression of *Fragilis* in the proximal rim of the epiblast marks the onset of germ cell competence. *Fragilis* has an IFN response element upstream of its exon 1, so it is very likely to be induced by IFN after initial priming by BMP4 of the proximal epiblast cells. These IFN inducible proteins can from a multimeric complex with other proteins such as TAPA1, which is capable of transduction of antiproliferative signals, which may be why the cell cycle time in founder PGCs increases from 6 to 16 hr, while the somatic cells continue to divide rapidly.

*Stella*, which has the putative nuclear localization signal and a nuclear export signal, was observed in both the cytoplasm and the nucleus. The onset of *Stella* is followed by the loss of *Fragilis* expression by E8.5. Therefore, *Fragilis* expresiion marks the onset of germ cell competence and *Stella* expression marks the end of this specification process. Expression of *Stella* in the founder PGCs marks an escape from the somatic cell fate and consistent with their pluripotent state. These studies indicate that specific set of genes are required to impose a germ line fate on cells that may otherwise become somatic cells. *Stella*, with its potential to shuttle between the nucleus and cytoplasm, could have a role in transcriptional and translational regulation, since many organisms possess elaborate transcriptional mechanisms to prevent germ cells from becoming somatic cells. Expression of *Stella* in the oocyte and preimplantation embryos indicates that it has a wider role in totipotency and pluripotency.

Example 7

The Link Between *Fragilis* and *Stella*

Only some of the cells that express *Fragilis*, ended up showing expression of *Stella* Only those cells with the higest levels of *Fragilis* expression become PGCs and began to express *Stella*. Furthermore, *Stella* positive PGCs never show expression of Hoxb1. More importantly, only somatic cells with lower levels of *Fragilis* expression, show Hoxb1 expression. Furthermore, only the somatic cells show expression of two other homeobox-containing genes, Lim1 and Evx-1. Therefore lack of expression of Hoxb1, Evx-1 and Lim1, appears to be important for the specification of germ cell fate.

FIGS. 8*a* and 8*b* show expression of various genes in single cell PGCs and somatic cells by PCR analysis.

Our experiments also show that Oct4 is not a definitive marker of PGC, Previously, Oct4 expression is demonstrated in totipiotent and pluripotent cells [Nichols, 199, Pesce, 1998; Yeom, 1996]. However, we find that Oct4 is expressed to the same extent in all PGCs and somatic cells. We do however find expression of T (Brachyuri) and Fgf 8 in PGCs indicating that PGCs are recruited from amongst embryonic cells that are initially destined to become mesodermal cells.

Example 8

PGC Specification

The founder PGCs and their somatic neighbours share common origin from the proximal epiblast cells. By analysing the founder PGC and the somatic neighbour, a systematic screen for critical genes for the specification of germ cell fate has been established. *Fragilis* is an interferon (IFN) inducible gene that can promote germ cell competence and homotypic association to demarcate putative germ cells from their somatic neighbours, and such an example may apply to other situation during development. Expression of *Stella* occurs in cells with high expression of *Fragilis*. *Fragilis* is no longer required once germ cell specification is complete, but *Stella* expression continues in the germ cell lineage. *Stella* may also be important throughout in the totipotent/pluripotent cells since it is also expressed in oocytes and early preimplantion development embryos.

Example 9

Germ Line and Pluripotent Stem Cells

PGCs can be used to derive pluripotent embryonic germ (EG) cells. However, unlike EG cells, PGCs do not participate in development if introduced into blastocysts. They either cannot respond to signalling molecules, or that they are transcriptionally repressed. PGCs once specified do not express *Fragilis* on their cell surface. However, EG cells clearly show expression of *Fragilis* on their cell surface as do ES cells. Both EG and ES cells express *Stella* as judged by Northern analysis, although *Stella* is expressed at a lower level in ES and EG cells than in PGCs. *Fragilis* and *Stella* therefore have a role in pluripotent stem cells. These genes are therefore markers of these pluripotent stem cells, where they may also have a role in conferring pluripotency on these stem cells.

Example 10

Proposed Roles of *Fragilis* and *Stella* in PGC Specification

*Fragilis* as a typical IFN-inducible cell surface protein, probably shares certain properties common to all of these family members (Deblandre, G. A. et al. Expression cloning of an interferon-inducible 17-kDa membrane protein implicated in the control of cell growth. J. Biol. Chem. 270, 23860-23866 (1995); Evans, S. S., Collea, R. P., Leasure, J. A. & Lee, D. B. IFN-a induces homotypic adhesion and Leu-13 expression in human B lymphoid cells. J. Immunol. 150, 736-747 (1993); Evans, S. S., Lee, D. B., Han, T., Tomasi, T. B. & Evans, R. L. Monoclonal antibody to the interferoninducible protein Leu-13 triggers aggregation and inhibits proliferation of leukemic B cells. Blood 76, 2583-2593 (1990)).

The acute but transient expression of *fragilis* is itself consistent with the kinetics of IFN-inducible genes that can increase by up to 40-fold within 1 h, and decline quickly after IFN withdrawal (Friedman, R. L., Manly, S. P., McMahon, M., Kerr, I. M. & Stark, G. R. Transcriptional and posttranscriptional regulation of interferon-induced gene expression in human cells. Cell 38, 745-755 (1984)). This *Fragilis* positive assembly of cells could correspond to about 100 TNAP positive cells (Lawson, K. A. & Hage, W. J. Clonal analysis of the origin of primordial germ cells in the mouse. Ciba Found. Symp. 182, 68-84 (1994); Ginsburg, M., Snow, M. H. & McLaren, A. Primordial germ cells in the mouse embryo during gastrulation. Development 110, 521-528 (1990)), which is larger than the number of *stella* positive cells.

According to our estimates, the *stella* positive cluster in the 129/SvEv mouse strain consists of approximately 36-43 cells, which is close to the expected 45 nascent PGCs. The *fragilis* positive cells probably form a community of cells through homotypic adhesion (Evans, S. S., Collea, R. P., Leasure, J. A. & Lee, D. B. IFN-a induces homotypic adhesion and Leu-13 expression in human B lymphoid cells. J. Immunol. 150, 736-747 (1993); Evans, S. S., Lee, D. B., Han, T., Tomasi, T. B. & Evans, R. L. Monoclonal antibody to the interferoninducible protein Leu-13 triggers aggregation and inhibits proliferation of leukemic B cells. Blood 76, 2583-2593 (1990)), from which the founder PGCs are recruited, thus demarcating them from most of the cells destined for somatic tissues. These IFN-inducible cell surface proteins are capable of transduction of antiproliferative signals (Deblandre, G. A. et al. Expression cloning of an interferon-inducible 17-kDa membrane protein implicated in the control of cell growth. J. Biol. Chem. 270, 23860-23866 (1995)), which is a probable mechanism by which the cell cycle time in the nascent PGCs increases from 6 to 16 h, while the somatic cells continue to divide rapidly.

The induction of *fragilis* in epiblast cells may not by itself be sufficient for the expression of *stella*, as shown by our in vitro studies-induction may require a specific signal thought to be within the niche, for PGC specification in vivo (Lawson, K. A. et al. Bmp4 is required for the generation of primordial germ cells in the mouse embryo. Genes Dev. 13, 424-436 (1999); McLaren, A. Signaling for germ cells. Genes Dev. 13, 373-376 (1999)). This signal could be a specific ligand that binds to *fragilis* during the specification of germ cell fate. Once nascent PGCs are established, expression of *fragilis* is diminished by E8.0, thus freeing the PGCs from homotypic adhesion for their migration into the genital ridge (Wylie, C. Germ cells. Cell 96, 165-174 (1999); Gomperts, M., Garcia-Castro, M., Wylie, C. & Heasman, J. Interactions between primordial germ cells play a role in their migration in mouse embryos. Development 120, 135-141 (1994)). *fragilis* must have other functions, as it is apparently expressed elsewhere in developing embryos. In this context, we also note *fragilis* expression in pluripotent ES and embryonic germ cells (data not shown), where it may have a role in the propagation of the pluripotent state.

The role of *stella* may in part be regulated by its potential to shuttle between the nucleus and cytoplasm. We have observed, for example, that overexpression of *stella* in somatic cells causes the protein to be retained in the cytoplasm and not in the nucleus, as is predominantly the case in PGCs (data not shown). A particularly critical event involved in the specification of PGCs is repression of the region-specific homeobox genes, by which nascent PGCs escape from the somatic cell fate. As the expression of *stella* is most intimately connected with the generation of PGCs, this gene is a chief candidate for either initiating or maintaining repression of Hox genes in PGCs. The detection of *stella* in the oocyte and through pre-implantation development (B. Payer et al., unpublished data; Sato, M. et al. Identification of PGC7, a new gene expressed specifically in preimplantation embryos and germ cells. Mech. Dev. 113, 91-94 (2002)) suggests that it may serve a critical role during all the phases of totipotent/pluripotent states in mice.

Example 11

Fragilis 2, Fragilis 3, Fragilis 4 and Fragilis 5

Specification of primordial germ cells in mice depends on instructive signalling events, which act first to confer germ cell competence on epiblast cells, and second, to impose a germ cell fate upon competent precursors *fragilis*, an interferon-inducible gene coding for a transmembrane protein, is the first gene to be implicated in the acquisition of germ cell competence.

In this and the following Examples (Examples 11 to 20), we describe four additional *fragilis*-related genes, *fragilis*2-5, which are clustered within a 70 kb region in the vicinity of the *fragilis* locus on Chr 7. These genes exist in a number of mammalian species, which in the human are also clustered on the syntenic region on Chr 11. In the mouse, *fragilis*2 and *fragilis*3, which are proximate to *fragilis*, exhibit expression that overlaps with the latter in the region of specification of primordial germ cells. Using single cell analysis, we confirm that all these three *fragilis*-related genes are predominant in nascent primordial germ cells, as well as in gonadal germ cells.

The *Fragilis* family of interferon-inducible genes is tightly associated with germ cell specification in mice. Furthermore, its evolutionary conservation suggests that it probably plays a critical role in all mammals. Detailed analysis of these genes may also elucidate the role of interferons as signalling molecular during development.

Example 12

Background to Examples

Germ line determination in the mouse is thought to occur through instructive signalling in the gastrulating post-implantation embryo [1, 2]. First, proximal epiblast cells acquire germ cell competence at E6.5, partly in response to extraembryonic ectoderm-derived signalling molecules. A subset of these competent cells then acquire a primordial germ cell (PGC) fate and a population of approximately 45 founder germ cells are detected in the posterior proximal region of the embryo at the base of the incipient allantoic bud on E 7.5 [1, 2]. The secreted signalling molecules, BMP4, BMP8b and BMP2 as well as components of the BMP signal transduction pathway, including Smad1 and Smad5, appear to be involved in the specification of PGCs [3-7]. However, in vitro culture studies and analysis of BMP4-deficient mice suggest that an additional signal may also be required for the acquisition of PGC fate, but its identity is yet unknown [2, 3].

We have identified *fragilis*, a putative interferon-inducible gene, which codes for a transmembrane protein that is apparently associated with the acquisition of germ cell competence by epiblast cells [8]. Extraembryonic ectoderm is able to induce *fragilis* expression in epiblast tissue, and BMP4 is required for this induction [8]. *fragilis* is expressed in proximal epiblast at E6.5, the region in which PGC-competent cells reside according to clonal analysis [1]. As these proximal cells move to the posterior proximal region during gastrulation, *fragilis* expression increases within a community of cells at the base of the incipient allantoic bud. Cells with the highest expression of *fragilis* initiate the germ cell-characteristic expression of TNAP and *stella*/PGC-7 [8, 9, 10]. These nascent PGCs with high expression of *fragilis* also show repression of Hox genes, including Hoxb1 in nascent PGCs [8].

In view of the strong association of *fragilis* with PGC specification, we have started to investigate further how this gene may be regulated and what precise function it serves during germ cell development. Towards this objective, we now report that *fragilis* belongs to a novel murine gene family, comprising five members, which code for five highly similar transmembrane proteins. More importantly, the genes are clustered within a 70 kb genomic region. As we found several homologues of the *Fragilis* family in human, cow and rat, they seem to be evolutionarily conserved amongst mammalian species. Most if not all homologous genes have been reported to be responsive to interferon signalling, which is in agreement with the presence of conserved interferon stimulable response elements (ISREs) within at least the murine and human loci. Furthermore, our in situ hybridisation and single cell expression analysis reveal that the two members located close to *fragilis*, *fragilis*2 and *fragilis*3, are also expressed in nascent PGCs, although their overall expression pattern in post-implantation embryos in other respects is distinct. Studies on the *Fragilis* family of genes could therefore be crucial for our understanding of PGC specification, especially since their homologues have been implicated in mediating homotypic cell adhesion and lengthening of the cell cycle time [14, 15]. These studies may also show how interferons act as signalling molecules, which has hitherto not been considered in the context of embryonic development.

Example 13

Materials and Methods: Database Searches and Animals

Ensembl and NCBI genome browsers are used for data retrieval.

Embryos and genital ridges used for in situ hybridisation experiments came from 129×129 or F1×GoF1 mothers, respectively. Embryos and genital ridges used for single cell analysis came from 129×SvEv or Oct4GFP(129)×MF1 mothers, respectively. The day of the vaginal plug was designated as E0.5. Embryos were staged according to Downs and Davies [22].

Example 14

Materials and Methods: In situ Hybridisation

3'-fragments of *fragilis* and *fragilis*2-5 cDNAs were PCR amplified using the primers described below, and cloned into pGEMT vector (Promega). DIG-labelled antisense RNA probes were synthesized using DIG RNA labelling kit (Sp6/T7; Roche). In situ hybridisation on embryos and urogenital ridges was performed as described [23, 24]. Hybridisation was carried out using 1 µl/ml DIG-labelled RNA probe in hybridisation buffer (50% formamide, 1.3×SSC (pH 5), 5 mM EDTA (pH 8), 50 µg/ml yeast RNA, 0.2% Tween-20, 0.5% CHAPS, 100 µg/ml heparin in DEPC treated $H_2O$) at 70° C. over night. Hybridised probe was detected using alkaline phosphatase conjugated anti-DIG Fab fragments (Roche) and BM Purple alkaline phosphatase substrate (Roche).

Example 15

Materials and Methods: Preparation, PCR and Southern Blot Analysis of Single Cell cDNAs Early bud stage embryos (E 7.5) and genital ridges (E 11.5) were isolated in DMEM/10% fetal calf serum/25 mM HEPES (pH 7.4). Fragments bearing primordial and gonadal germ cells, respectively, were dissected out and dissociated into single cells. The latter were picked using mouth pipettes and their cDNAs were amplified as described previously [25]. The following primers were used in order to PCR amplify *stella* cDNA and 3'-fragments of *fragilis* and *fragilis*2-5 cDNAs (25 cycles of amplification): *stella*:

```
stella:
5'CTCACAGCTTGAGGCTTCTAA3',
5'GCGATTCAGATGTCTCTGCAC3, fragilis:
5'GTTATCACCATTGTTAGTGTCATC3',
5'AATGAGTGTTACACCTGCGTG3';

fragilis3:
5'GATCTTCAGCATCCTTATGGTC3',
5'GAAGGTAACATTTGCATACGCG3';

fragilis2:
5'CCTTCCTTATTCTCACTCTG3',
5'GTTGCAAGACATCTCACATC3';
```

```
-continued
fragilis4:
5'AACTTGGAGGCTGCAAGGCAG3',
5'CTCGGAACTCTTAGTTATAGTC3';

fragilis5:
5'TGCTCTGGTCATCTCCCTCA3',
5'CAGGATAAGGGGCAACTCTG3'.
```

PCR products were run on 1.5% agarose/TBE electrophoresis gels. For Southernblot analysis, single cell cDNAs were blotted onto Hybond-N+membranes (Amersham) and probed with $^{32}\alpha P$ dCTP-labelled DNA probes comprising the 3'regions of *fragilis*, *fragilis*2 and *fragilis*3 cDNAs and full length *stella* cDNA. GAPDH was used as loading control. Blotting signal was detected using a Fuji film FLA 5000 scanner. Signal strength was quantified in relation to GAPDH signal, whereby relative gene expression was calculated as ratio of gene signal to GAPDH signal and this ratio was subsequently normalized by division through the highest hybridisation signal per blot. For dotblot analysis, full length *fragilis* cDNAs were blotted and probed with $^{32}\alpha P$ dCTP-labelled 3' probes.

Example 16

The *Fragilis* Gene Family

Using the cDNA sequence of *fragilis* as a template to search the ensembl genome browser (www.ensembl.org), we identified eight mouse genes with moderate to high DNA sequence similarity to *fragilis* (45-74%). ESTs from a variety of embryonic and adult tissues have been reported for five of these genes, of which four possess a two-exon structure similar to *fragilis*. Analysis of the genomic location of the latter revealed that the four genes cluster around the *fragilis* locus within a 70 kb region on the distal tip of mouse Chr 7 (F5). We therefore named the four novel genes *fragilis*2-5, reflecting their genomic location, similarity to *fragilis* and germ cell associated expression pattern (see below; FIG. 9). The four remaining putative genes that we detected have few or mostly no reported ESTs and are coded by a single exon unlike *fragilis*. We therefore consider them to be pseudogenes.

To determine whether the *Fragilis* genes are evolutionary conserved, we have identified four homologues of mouse *Fragilis* in the human genome on Chr 11 (p 15.5), a region which is indeed syntenic to the *Fragilis* family locus on mouse Chr 7 (FIG. 9). Three of these genes, Ifitm1 (9-27), Ifitm2 (1-8D) and Ifitm3 (1-8 U), share 58-65% similarity to the *fragilis* gene cluster and are located within an 18 kb genomic stretch [11]. They are responsive to type1/2 interferons and code for interferon induced transmembrane (Ifitm) proteins, involved in antiproliferative signalling and homotypic cell adhesion [12-15]. The fourth gene, ENSG142056, a novel gene with two exons, is highly similar to mouse *fragilis*4 (83% DNA sequence similarity) and neighbours Ifitm2. The human *Fragilis* family homologues hence form a similar genomic cluster as the five *Fragilis* genes in the mouse. Phylogenetic tree analysis suggests however, that only two *Fragilis* genes, *fragilis*4 and either *fragilis*, *fragilis*2 or *fragilis*3, have been conserved from mouse to human (data not shown). Subsequent gene duplications may therefore have occurred independently in both species. We also identified two *Fragilis* family-like genes in cow (bovine 1-8 U, bovine 9-27) and four genes in rat (P26376, JC1241, NP110460, AAD48010). While the rat genes have been annotated as putative interferon inducible, the two bovine genes that are similar to the human Ifitm genes, have been reported to respond to interferon signalling [16,17]. Due to limited mapping information of the cow and rat genomes, we cannot, at this stage, deduce whether these homologous genes are also organised in a cluster. Interferon stimulable response elements (ISREs), GGAAAN(N)GAAAC) within the human Ifitm locus confer the responsiveness of the three human Ifitm genes to interferons [11, 18]. Similar ISRE consensus sequences are also found within the *Fragilis* family cluster in the mouse, associated in particular with *fragilis*, *fragilis* 2 and *fragilis*5 (FIG. 9).

The murine family of *fragilis* and related genes code for five highly similar transcripts of 104 to 144 amino acids, each containing two predicted transmembrane domains (FIG. 10). The sequence similarity to human, cow and rat *fragilis*-like genes is equally high (overall 68% amino acid similarity). It should be noted, that the first transmembrane domain as well as the following stretch to the beginning of the second transmembrane domain constitute the regions of highest intra- and inter-species conservation.

Example 17

*fragilis*, *fragilis*2 and *fragilis*3 are Expressed During Early Post-Implantation Development We analysed the expression pattern of the five *Fragilis* family genes by whole mount in situ hybridisation using probes that span the 3' region (150-200 bp) of the corresponding mRNAs. These probes show no significant cross-hybridization between members of the *Fragilis* family as judged by dotblot analysis (data not shown). As reported, we saw expression of *fragilis* restricted to the epiblast at E5.5 and E6.5. More importantly, around E7.5, expression of *fragilis* is intense within a population of cells at the base of the allantois in the region where PGC specification occurs (FIG. 11*a-c*) [8]. *fragilis*2 and *fragilis*3 are also expressed within the epiblast of E5.5 embryos (FIG. 11*g*, data not shown). While expression of *fragilis*2 is thereafter significantly downregulated, *fragilis*3 remains expressed at a similar level in the embryonic tissues. At E7.5, *fragilis*2 is detected in the posterior mesoderm, while *fragilis*3 expression is seen throughout the epiblast. More significantly, like *fragilis*, both *fragilis*2 and *fragilis*3 show high expression in the region where the cluster of nascent PGCs originates (FIGS. 11*i/i',n/n'*). Thus, these three members of the *Fragilis* family show significant expression at the time and site of PGC specification.

At E8.5, *fragilis* expression is seen in cells at the base and within the proximal third of the allantois (FIG. 11*d*). Additionally, a signal is detected in the latero-anterior aspects of the developing brain (FIG. 11*e*). At this stage, *fragilis*2 is expressed in the mesoderm in the caudal half of the embryo (FIGS. 11*j,k*), whereas *fragilis*3 appears present throughout the entire embryo with the exception of the developing heart (FIG. 11*p-r*). It is noteworthy, that expression seems significantly stronger in single cells at the base and within the proximal third of the allantois at this stage (FIG. 11*q*). At E9.5, when PGCs have started to migrate along the hindgut, *fragilis* signal is seen in a population of cells located at the beginning of the invaginated hindgut. In addition, the signal appears enhanced in the pharyngeal arches (FIG. 11*f*). At this stage, *fragilis*2 expression appears restricted to the tailbud, the mesoderm caudal to the 12$^{th}$ somite and the lung primordium (FIG. 11*l*).

In contrast to the first three members of the family, neither *fragilis*4 nor *fragilis*5 showed expression at early post-implantation stages (E7.0-E8.5, data not shown). Consequently, only the three genes at the centre of the family cluster, that is *fragilis*, *fragilis*2 and *fragilis*3 are expressed in the embryo between E5.5 and E9.5. While their expression pattern is distinct, there is a striking overlap within the region where founder germ cells are located. This suggests that the three neighbouring genes, *fragilis*, *fragilis*2 and *fragilis*3, may share regulatory elements that are likely to be present within the cluster. These regulatory elements may also be responsible for the genes' overlapping expression pattern specifically around the region of nascent PGCs.

Example 18

Figure 13A:
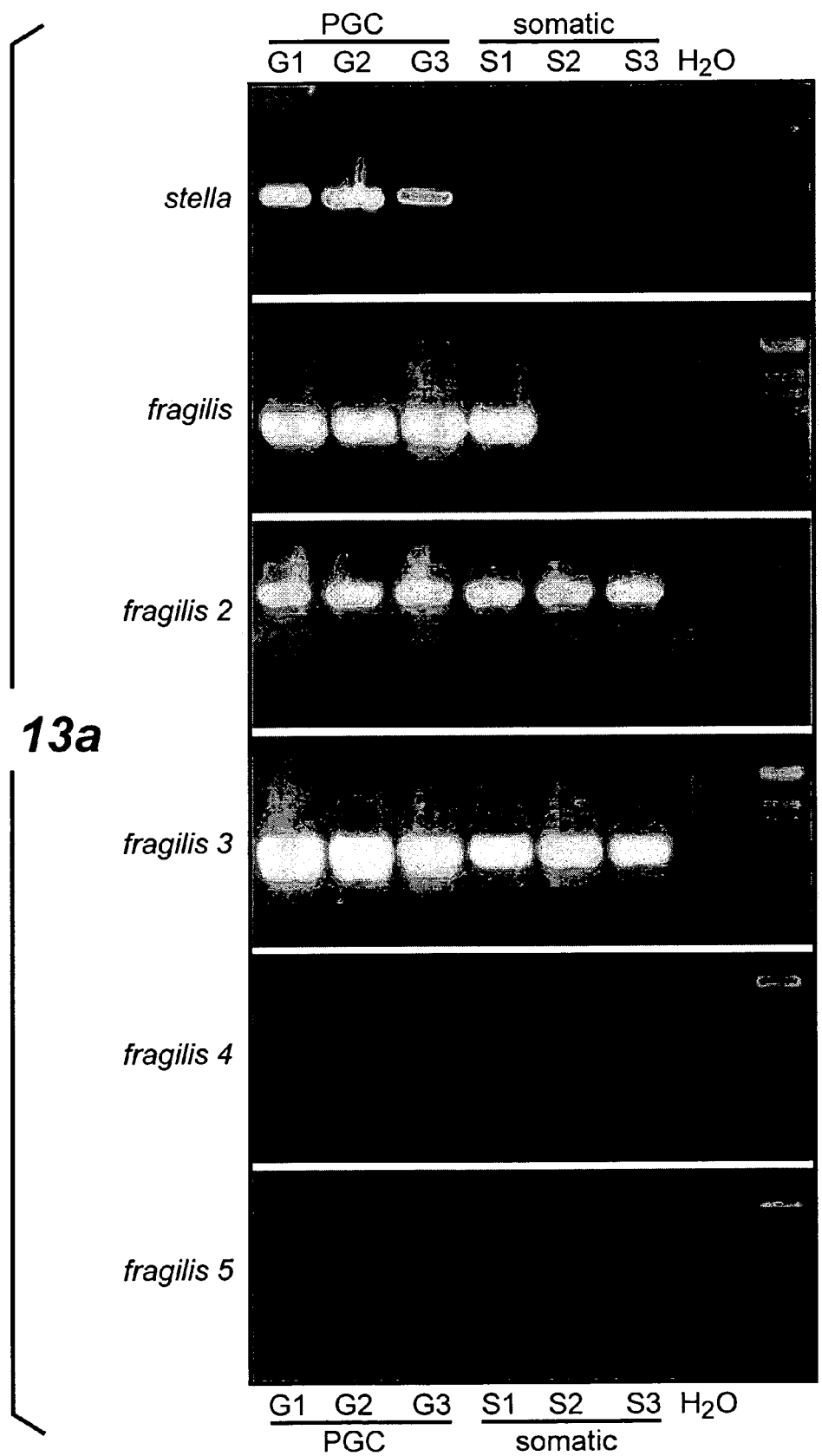
FIG. 13. Expression analysis of the *Fragilis* family genes in single cells from the region of germ cell specification of E7.5 embryos. (a) shows PCR analysis of cDNAs from three nascent, *stella* positive PGCs and three surrounding, *stella* negative somatic cells. Note that *fragilis*, *fragilis*2 and *fragilis*3 are expressed in PGCs and somatic cells, while *fragilis*4 and *fragilis*5 are not detected in any of the cells. (b) shows expression of *fragilis*, *fragilis*2 and *fragilis*3 in single cell cDNAs using Southernblot analysis. GAPDH was used as blotting control. (c) Semi-quantitative expression analysis of the Southernblot data shows that all three *Fragilis* genes are predominantly expressed in nascent PGCs compared to the somatic cells within the region.
Figure 13B:
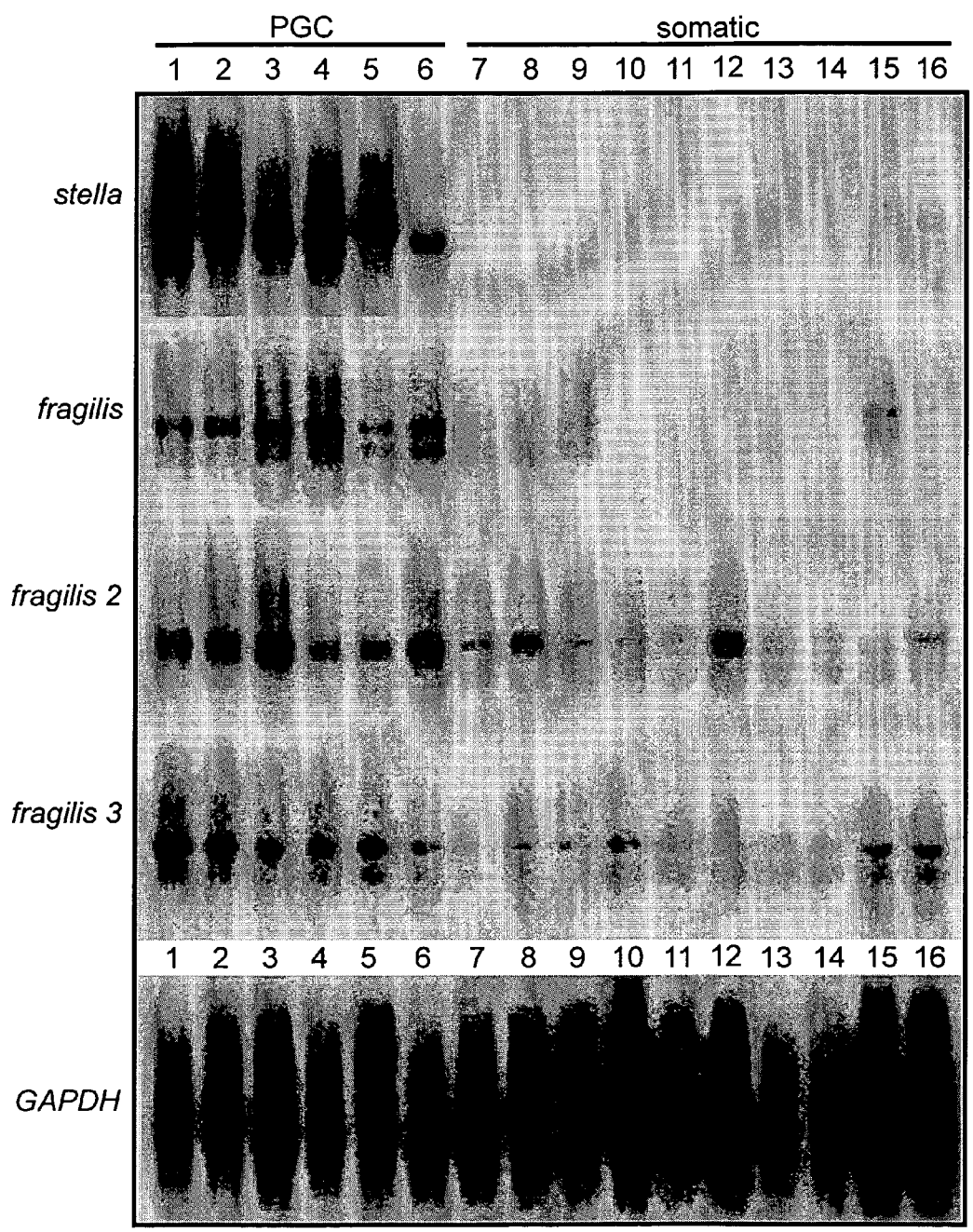

Single Cell Analysis of *fragilis*, *fragilis*2 and *fragilis*3 in PGCs and Somatic Neighbours To obtain more precise information on the expression of the new *Fragilis* family members in the context of germ cell specification, we tested single cell cDNAs from PGCs and surrounding somatic cells sited at the base of the incipient allantoic bud in E7.5 embryos. Both *fragilis*2 and *fragilis*3 were expressed in nascent PGCs, which show transcription of the germ cell marker *stella*/PGC7 (FIG. 13*a*) [8,10]. The two *Fragilis* family members were also detected in surrounding somatic cells that lack expression of *stella*/PGC7 [8]. Importantly, semi-quantitative analysis using Southernblotting showed that *fragilis*2 and *fragilis*3 are expressed predominantly and at higher levels in nascent PGCs compared to the neighbouring somatic cells (FIGS. 13*b,c*). This mimics the pattern seen for *fragilis*, although expression of the latter is more specific to germ cells. Combined with the in situ hybridisation data, these observations further support the notion that certain common control elements may be involved in the upregulated expression of the three *Fragilis* genes in the founder PGCs.

Figure 14A:
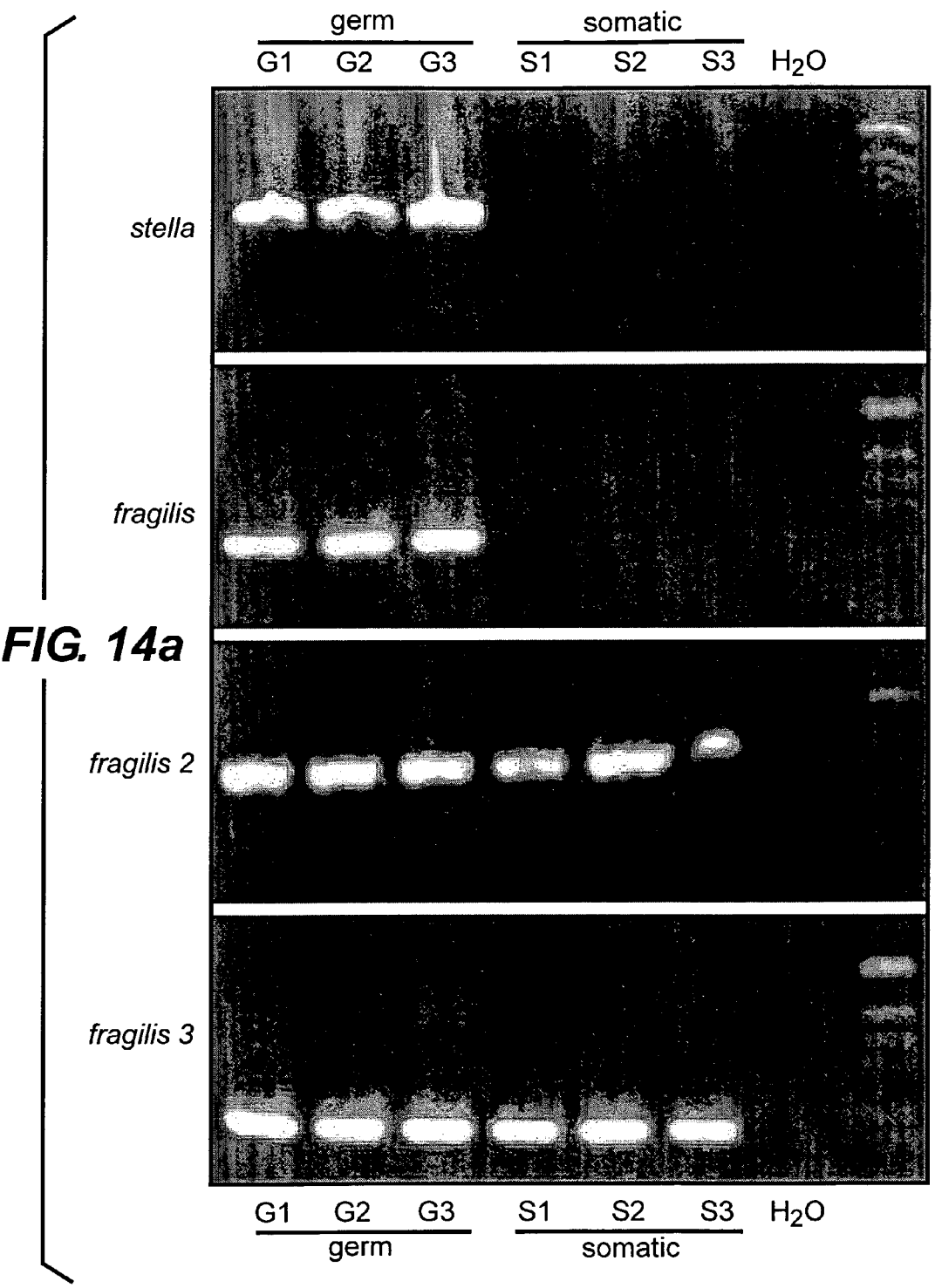
FIG. 14. Expression analysis of *fragilis*, *fragilis*2 and *fragilis*3 at E11.5/E12.5 in single cells from the genital ridge and by in situ hybridisation. (a) shows PCR analysis of cDNAs from three gonadal *stella*-positive germ cells and three surrounding, *stella*-negative somatic cells. While *fragilis* is detected only in the three germ cell clones, *fragilis*2 and *fragilis*3 are expressed in the germ cells as well as the somatic cells. (b) shows in situ hybridisation of urogenital ridges of E11.5/E12.5 embryos. While *fragilis*3 is expressed in the mesonephros as well as the genital ridge, *fragilis* and *fragilis*2 are restricted to the genital ridge. The staining pattern for *fragilis* appears punctuate and restricted to single cells mimicking the pattern seen for the germ cell-specific *stella* gene. asterix: genital ridge; black arrowhead: mesonephros; scale bars: 400 µm.
Figure 14B:
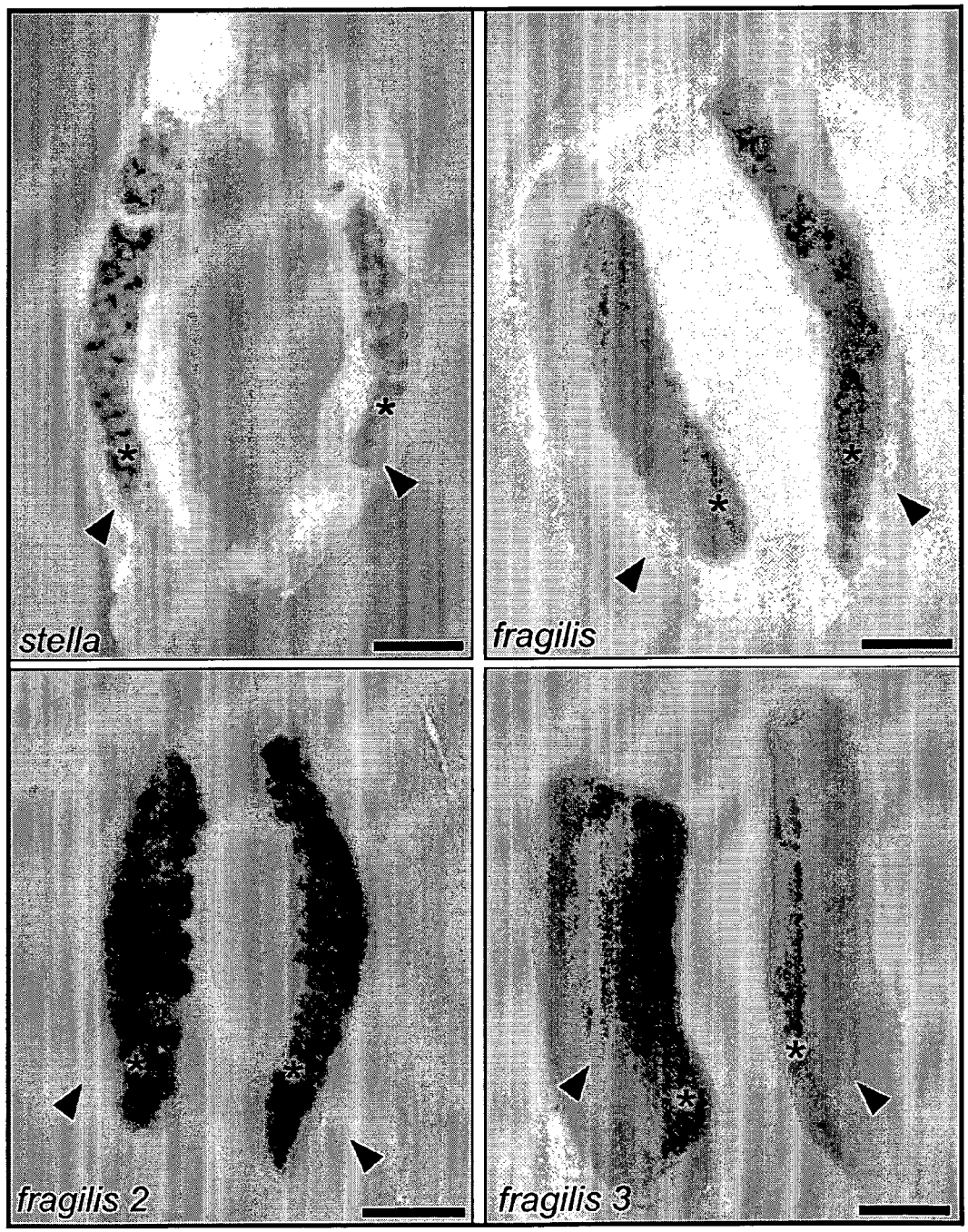

During the developmental stages directly subsequent to PGC specification, all three *Fragilis* family genes are expressed in a population of cells associated with the allantois and in a location where premigrating PGCs are thought to reside (FIGS. 11*d,k,q*). The precise gene expression during migration of PGCs is not clear at this stage from our analysis. However, using in situ hybridisation and PCR analysis of cDNAs from single cells within the genital ridge, we found clear expression of *fragilis*, *fragilis*2 and *fragilis*3 in the gonadal germ cells at E11.5-12.5 (FIG. 14). While *fragilis*3 expression extends to the mesonephros, *fragilis* and *fragilis*2 signal was restricted to the genital ridge. A punctuate staining pattern was seen for *fragilis*, mimicking the germ cell restricted expression of *stella*/PGC7 (FIG. 14*b*). This pattern in addition to the PCR analysis suggests that *fragilis* is expressed predominantly if not solely in germ cells at E11.5. As was the case in earlier embryos, neither *fragilis*4 nor *fragilis*5 were detected in gonadal germ cells (data not shown).

Example 19

Discussion

In this study we describe the identification of the murine *Fragilis* gene family, which appears to be conserved amongst mammalian species, and whose members code for five highly similar transmembrane proteins. Three members of the *Fragilis* family, *fragilis*, *fragilis*2 and *fragilis*3, exhibit expression, which is associated with germ cell specification and development Located at the cell membrane, the *Fragilis* proteins may be crucial for mediating interactions amongst germ cells and their surrounding neighbours. While the three genes are expressed earlier at E5.5 and thereafter to a varying extent, they all show upregulation of expression within nascent PGCs. It is likely that a cis control element exists within the locus that is required for this expression, which continues within gonadal PGCs. Future studies will elucidate where these control elements are located and how they regulate expression of the *fragilis*-related genes.

Although the five *Fragilis* family members are clustered within a small genomic region, it appears that neither *fragilis*4 or *fragilis*5 show expression in early embryos or embryonic germ cells. It is striking that these two members are located at the periphery of the cluster in contrast to the centrally located *fragilis, fragilis*2 and *fragilis*3 genes. This lack of expression may be due to the presence of boundary elements, which might restrict the action of control elements to genes present within the centre of the cluster. Since sequence comparison suggests that gene duplications may have occurred independently in the two species, it appears that a certain evolutionary constrain may exist on duplication and maintenance of the duplicated genes within immediate neighbourhood. Since the four human homologues of the *Fragilis* family in the syntenic region are also arranged in a genomic cluster and are highly similar to the family genes, it is tempting to suggest that they may also serve similar functions as in the mouse.

The presence of several interferon stimulable response element (ISRE) consensus sequences within the *Fragilis* locus, together with the similarity of the genes to their interferon-inducible human and bovine counterparts, suggest very strongly that *fragilis* and the *fragilis*-related genes are responsive to interferons. Indeed, the ISRE tandem repeat present in the 5' flanking region of human Ifitm1, Ifitm2 and Ifitm3 genes is also present in the 5' flanking region of *fragilis* exon 1 [11]. Interferons, as secreted signalling molecules, have so far been implicated mainly in the process of immune response, the inhibition of cellular growth and the control of apoptosis [19]. Although interferons are expressed in the post-implantation embryo, their role during development has not been addressed in detail [20, 21]. Our studies have pointed to a possible involvement of interferons in germ cell development. Future work will determine whether the *Fragilis* genes respond to interferon signals in all or some instances where the genes are expressed, which we expect in view of the presence of conserved ISRE elements in the mouse and human loci.

Example 20

Conclusion

We have identified the *Fragilis* family of interferon inducible genes, which code for transmembrane proteins. The five members are arranged in a cluster within a genomic region of 70 kb in the mouse that also contains ISRE elements. The centrally located *fragilis, fragilis*2 and *fragilis*3 genes are of particular interest, because they are expressed in the region where germ cell specification occurs. The family is evolutionary conserved amongst mammalian species where it may serve similar functions. Detailed studies of the *Fragilis* family may also show what role interferons have in embryonic development.

Example 21

*Stella* is a Maternal Effect Gene Required for Normal Early Development in Mice In this and the following Examples (Examples 21 to 25), we have investigated the effects of a targeted mutation of *stella* in mice. Maternal inheritance in mammalian oocytes includes proteins important for totipotency and epigenetic modifications[1], as well as factors crucial for early development, which are transcribed from so called maternal effect genes[2-7].

Amongst these maternally inherited proteins is *Stella*, which is also expressed in preimplantation embryos, primordial germ cells, and pluripotent cells[8,9]. We show that while matings between heterozygous animals resulted in the birth of apparently normal *stella*-null offspring, *stella*-deficient females showed severely reduced fertility, which is due to a lack of maternally inherited *Stella* in their oocytes.

*Stella* is a maternal effect gene, as the phenotypic effect on embryonic development is a consequence of the maternal *stella* mutant genotype. Indeed, we demonstrate that embryos lacking *Stella*-protein are compromised in preimplantation development and rarely reach the blastocyst stage. Furthermore, we show that *SETLLA* that is expressed in human oocytes[10] is also expressed in human pluripotent cells and in germ cell tumours. Interestingly, human chromosome 12p, which harbours *SETLLA* is consistently overrepresented in these tumours[11]. These findings suggest a similar role for *SETLLA* during early human development as in mice and a potential involvement in germ cell tumours.

Figure 15N:
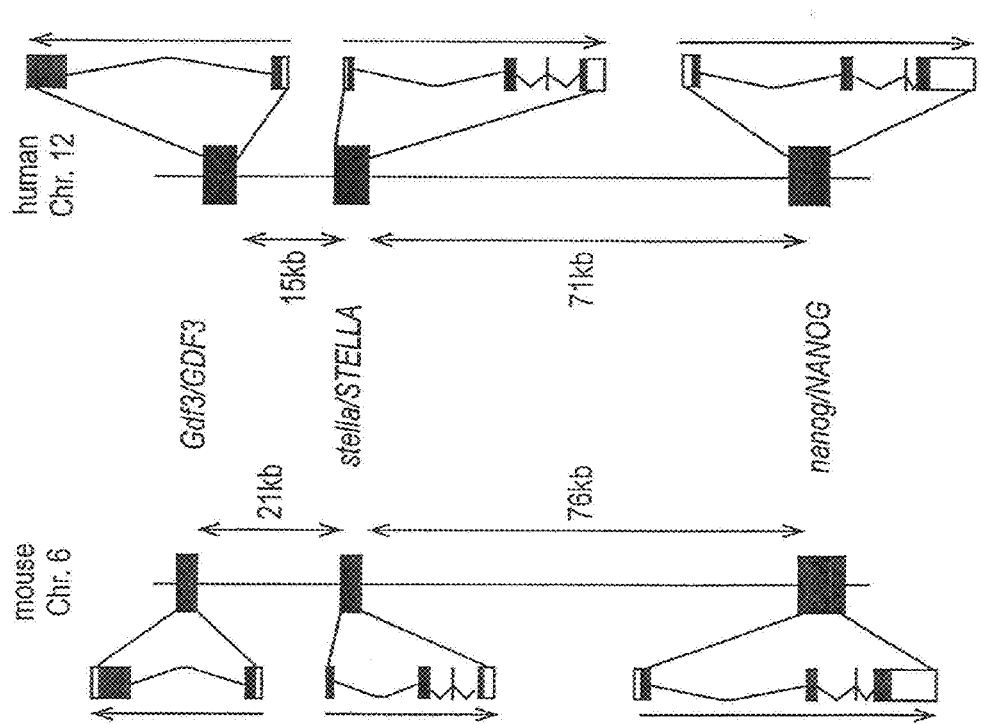
FIG. 15. Stella expression during preimplantation development and evolutionary conservation. a-l, Confocal sections of anti-*stella* (a,d,g,j) and propidium iodide (b,e,h,k) stained embryos (c,f,i,l merged images). Maternal *stella* is stored in the unfertilised egg (a-c) (arrow, exclusion of Stella from condensed metaphase chromosomes) and localizes both to the cytoplasm and pronuclei (PN) after fertilisation (d-f, PB, polar body). Also during later stages (2-cell, g-i; 4-cell, j-l) it can be seen both in the cytoplasm and the nucleus. Scale bar=20 µm. Synteny (m) of the *stella* gene in mouse, rat and human and close up view (n) of *stella* and its neighbouring genes in mouse and human. Arrows indicate the direction of transcription. o, Alignment of Stella protein sequences. Identical amino acids have a black background and similar amino acids a grey one. Putative nuclear export and localisation signals are marked by red and black lines, respectively. The red stars indicate conserved hydrophobic amino acids, which are typical for nuclear export signals[27]. p, RT-PCR analysis of *SETLLA*-expression in human pluripotent cells and reproductive organs. RPL32 was used as control. ES, embryonic stem cells; EC, embryonic carcinoma cells (nTera2); tet, testis tumor; te, normal testis; ov, normal ovary; –Rt, without reverse transcriptase; 0, water control.

The aim of this study was to determine the role of *stella* by loss of function analysis in mice. In our previous work, we have shown that expression of *stella* (also called PGC7) is activated during the process of germ cell specification at E7.25 specifically in the founder population of lineage restricted primordial germ cells (PGCs)[8,9]. Thereafter it is expressed in the germ line until about E15.5 in male and E13.5 in female gonads. Expression of *stella* resumes in the immature oocytes in newborn ovaries, and it is subsequently detected in maturing oocytes and in preimplantation embryos (FIG. 15*a-l*)[8]. Soon after the formation of the zygote, *Stella* accumulates in the pronuclei, although it is also detected in the cytoplasm (FIG. 15*d-f*). Both cytoplasmic and nuclear staining continues during cleavage stages until the blastocyst stage, after which *Stella* is downregulated (FIG. 15*g-l* and data not shown)[8], until its re-appearance in the nascent PGCs[8,9].

Example 22

Materials and Methods

Immunofluorescence

Embryos were fixed in 4% paraformaldehyde for 15 minutes, washed 3 times with PBS and permeabilised in AB-buffer (1% Triton-X100, 0.2% SDS, 10 mg/ml BSA in PBS), which was also used for the following antibody incubations and washes. They were then incubated in primary antibody (anti-*Stella*[9] 1:200, anti-PGC7[8] 1:2000) overnight at 4° C., washed 3 times and incubated with secondary antibody for 1-2 hours at room-temperature (Alexa 564, Molecular probes, 1:500). After 3 further washes in AB-buffer, embryos were rinsed once in PBS and incubated at 37° C. with 0.1 mg/ml Rnase A (Roche) in PBS for 30 minutes. Finally embryos were incubated for 10 minutes in PBS with propidium iodide (2 μg/ml) and mounted on slides in Vectashield (Vector Laboratories) mounting medium, which also contained propidium iodide.

For E11.5 PGC-stainings, genital ridges were washed in PBS, treated for 10 minutes at 37° C. with Trypsin/EDTA (Gibco), diluted in PBS and dissociated into a cell suspension. Cells were allowed to settle down on poly-L-lysine treated slides and fixed with 3% formaldehyde for 15 minutes. After permeabilisation with 0.2% Triton X-100 in PBS and 3 washes in PBS cells were blocked with 3% BSA in PBS (also used for subsequent washes and antibody dilutions) for 40 minutes and incubated with primary antibodies (anti-*Stella* 1:100, anti-SSEA1 (=TG1), P. Beverley 1:2) overnight at 4° C. Then the cells were washed and incubated with secondary antibodies (Alexa 564, Alexa 488, Molecular probes, 1:500) for 1.5 hours. After washing, Rnase (0.1 mg/ml) treatment was done for 1 hour at room temperature and the cells were mounted with Vectashield containing Toto-3 (Molecular probes, 1:1000).

Immunofluorescence was visualized on a BioRad Radiance 2000 confocal microscope.

Identification of *Stella*-Homologues

Human *SETLLA* was identified by blasting the mouse *Stella* protein sequence against the translated human genome sequence using the Ensembl server (http://www.ensembl.org). The only hit showing the same intron-exon structure as the mouse gene is located on the syntenic region (FIG. 15*m,n*) and was therefore considered to be the human orthologue (hits without introns were considered as pseudogenes). Three IMAGE-EST clones (Genbank IDs: AA927342, AI066520, AA564230; UniGene cluster Hs.131358), which aligned to the genomic region, were fully sequenced by us to confirm the predicted sequence.

The putative rat-*stella* sequence was mapped as above and deduced from the alignment of the mouse cDNA sequence with the syntenic rat genome sequence.

RT-PCR Analysis of Human Tissues

1 µg total RNA of each human tissue (source: Ambion and see acknowledgements) was reverse transcribed into 1$^{st}$ strand cDNA with Superscript II reverse transcriptase (Gibco) for 1 hour at 37° C. 1 µl of this cDNA was amplified by a 30 cycle PCR-reaction using primers for human *SETLLA* (5'-CAATTTGAGGCTCTGTCATCAG-3', 5'-TTCATCT-CACTGACTTTGGGC-3') or ribosomal protein L32 (5'-AGTTCCTGGTCCACAACGTC-3', 5'-TGCACAT-GAGCTGCCTACTC-3').

ES-cell Manipulation and Knockout Verification

The targeting construct consisted of 1.5 kb of upstream and 4.1 kb of downstream genomic sequence flanking the second exon of *stella*. The 5' arm terminated after the first 32 bp of exon 2, which was fused to an IRES lacZ reporter, followed by a promoted neo selectable marker. The construct was linearized and electroporated into CCB mouse embryonic stem (ES) cells which were placed under selection. Individual G418-resistant clones were picked and screened for correct integration of the targeting construct by PCR using a vector primer and a primer external to the 5' arm. 288 clones were screened of which two exhibited the expected size bands in the PCR. Homologous recombination was also confirmed by Southern blot using 5', 3' and neo-probes on NcoI and EcoRI digested genomic DNA. The correctly targeted ES-cell clone F4 was injected into MF1 and C57BL6 blastocycsts to produce chimeric mice. Germline transmission was achieved by breeding the male chimeras with 129Sv/Ev females. All analysis was done on the inbred 129Sv/Ev background. To confirm that the *stella* gene was correctly inactivated, mice were genotyped by Southern blot as above (FIG. 16*b*). Furthermore we performed RT-PCR (same protocol as for human tissues—see above) on testis and ovary RNA of wt, heterozygous and homozygous mice (FIG. 16*c*), using exon 2-specific primers (5'-AGACGTCCTACAACCAGAAAC-3',5'-CCGAACAAGTCTTCTCATCTT-3').

Counting of Primordial Germ Cells

Embryos of *stella*-heterozygous intercrosses were dissected out at E8.5, fixed with 4% paraformaldehyde and stained for TNAP-positive PGCs with α-naphthyl phosphate/fast red TR solution (Sigma) as previously described[20,26]. The posterior parts of the embryos were flattened under coverslips and used for counting PGCs, while the anterior parts were used for genotyping by PCR.

Histology

Testes and ovaries from adult mice were fixed in Bouin's fixative at 4° C. overnight and washed thoroughly in 80% ethanol. After dehydration through an ethanol series they were transferred into xylene and embedded in Paraplast Plus wax (Sigma). 8 µm sections were cut, rehydrated and stained with Ehrlich's Haematoxilin (BDH) and 1% eosin (Sigma). After dehydration, slides were mounted with DPX (BDH).

Matings and in vitro Culture

All studies for the assessment of fertility and embryonic development were done using natural matings. Mice were kept on a constant light/dark cycle and mating was assumed to have happened in the middle of the dark period before a vaginal plug was detected (E0.5=midday on day of plug). Embryos were collected by flushing oviducts/uteri at the time of the observed stages (E0.5-E3.5) or at E1.5, if they were cultured. Culturing was done under 5% $CO_2$ in KSOM medium. Work on animals was performed under Home Office project licences PPL80/1280 and PPL80/1706.

Generation of *Stella*-GFP Mice

Using the *stella*-cDNA as a probe, we screened a gridded genomic 129 pBeloBAC library (Genome Systems St Louis, Mo.) to identify a clone harbouring the *stella* locus. We subcloned 11.5 kb of genomic sequence including about 8.5 kb upstream sequence and exon 1, intron 1 and the start of exon 2 and fused it in frame to eGFP (Clontech) and a SV40-polyadenylation signal. This sequence was then injected into pronuclei of B6CBA F2 zygotes, to generate transgenic mice. The transgene was maintained on the same genetic background and the onset of expression of the paternal allele was observed by mating *stella*-GFP transgenic males with non-transgenic females.

The cDNAs of the *Stella* homologues mentioned in this study have the following GenBank accession numbers: mouse *Stella* (AY082485), rat *Stella* (BK001414, pending), human *SETLLA* (AY317075, pending).

Example 23

*Stella* Homologues

Figure 15M:
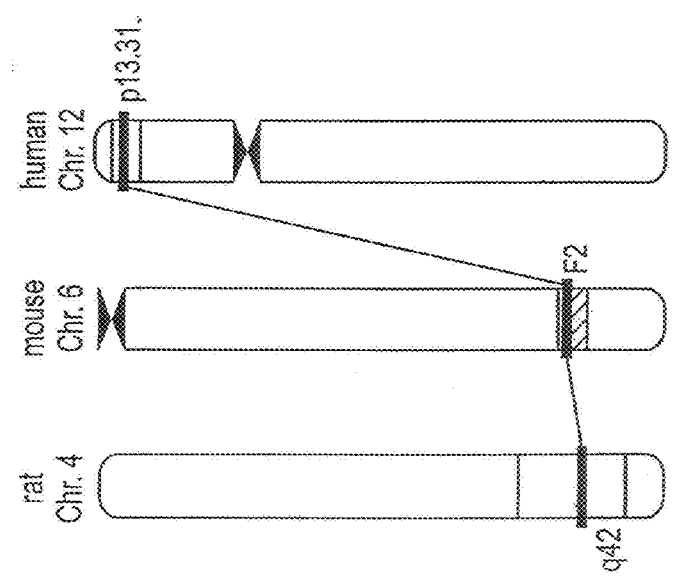
Figure 15O:
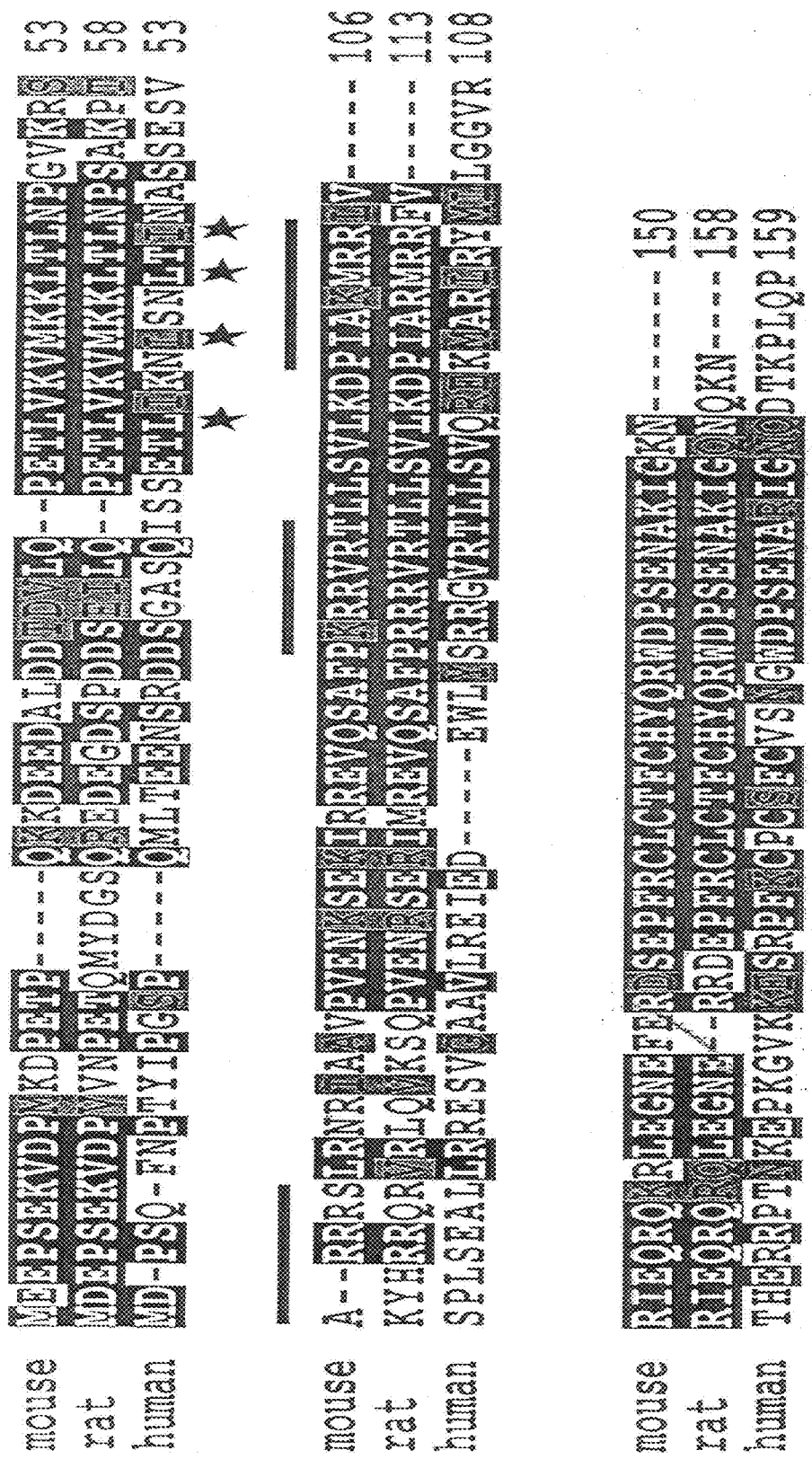

We have now identified *stella* homologues in the rat and human genomes, which show the same exon-intron structure, and are located within the syntenic chromosomal regions (see FIGS. 15*m,n*). The mouse gene is in position F2 of chromosome 6, the rat gene on q42 of chromosome 4 and the human gene on p13.31 of chromosome 12. Only one expressed-sequence tag (EST) (BI289609, aorta pool) was found in the rat, while several human ESTs mainly from germ cell tumour libraries (UniGene cluster Hs.131358) matched the genomic sequence. The full-length amino acid sequences (FIG. 15*o*) of the mouse and rat protein showed 70% identity (84% similarity), but the mouse and human proteins shared only 35% identity (53% similarity). While the *Stella* orthologues of rodents and humans have clearly diverged, conserved sequence stretches are found in the centre and the C-termini of the proteins. The biochemical function of these motifs remains to be discovered, but some of the predicted nuclear localisation and export signals reside within the regions of higher conservation.

Example 24

Expression of Stella

Figure 15P:
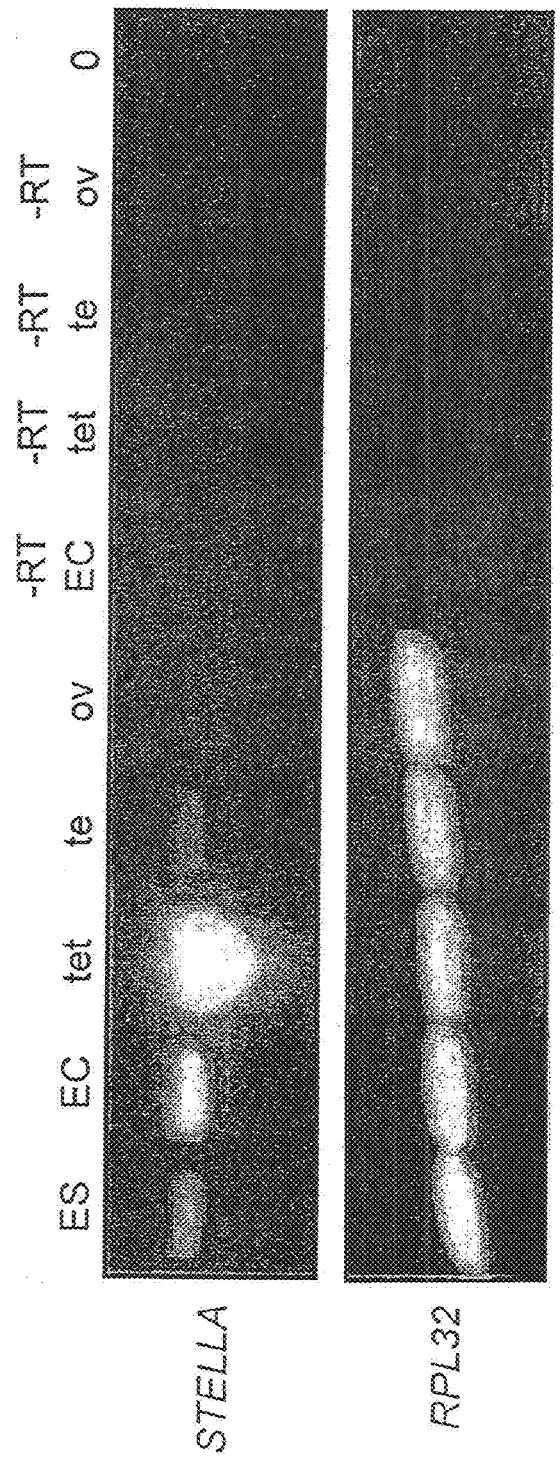

To study the expression of human SETLLA, we performed RT-PCR analysis on pluripotent cell lines and reproductive organs (FIG. 15p). We detected SETLLA in human embryonic stem (ES) cells and embryonic carcinoma (EC) cells, as well as in normal testis and ovary. The strongest expression was found in a testicular germ cell tumour, which shows characteristics of pluripotency[11]. Expression of SETLLA in other tumours and somatic tissues was either very low or undetectable (data not shown). Our findings concur with a recent study[10], where SETLLA (termed fragment 7.1) was detected in human oocytes and in EC cells, in which it was down-regulated after retinoic acid-induced differentiation. These findings strengthen the hypothesis that SETLLA might have a similar role in humans as in mice. Furthermore, the short arm of chromosome 12 (12p) on which SETLLA is located, is consistently overrepresented in testicular germ cell tumours[11]. Stella/SETLLA resides within a conserved cluster of genes consisting of nanog/NANOG[12,13] and gdf/GDF3[14] (FIG. 15n), which are associated with pluripotency and germ cell tumours. The conserved proximity in mice and humans and the overlapping expression patterns of these genes suggest a possible co-regulation at a transcriptional level[15]. Clearly, these findings prompt a careful analysis of the functions of stella and its neighbours in mouse and man.

Example 25

Stella Knockout Mice

Figure 16A:
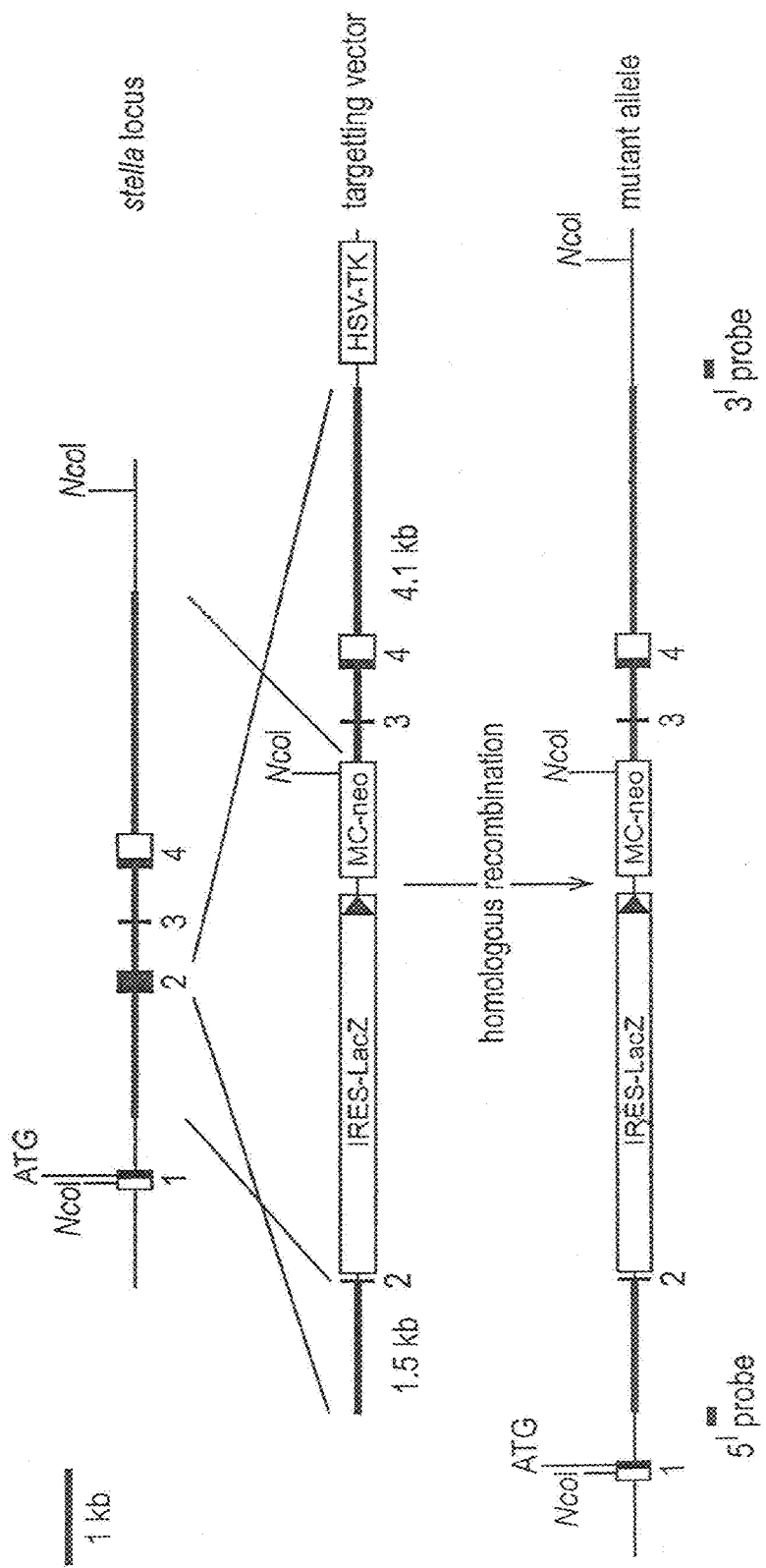
FIG. 16. Knockout strategy of *stella* and confirmation of correct targeting by Southern-blot and RT-PCR. a, The targeting vector was designed to delete exon 2 and replace it with an IRES-LacZ/MC-neo reporter-selection cassette. HSV-TK was used for negative selection against non-homologous recombination. 5', 3' and neo-probes were used to confirm correct targeting of ES-cells. b, Southern blot analysis of genomic DNA derived from littermate mice born from a *stella*$^{+/-}$ intercross. The example shows a NcoI digest hybridised with the 3' probe, indicating the absence of the wild-type allele in *stella*$^{31\ /-}$ mice. c, RT-PCR of testis (te) or ovary (ov) RNA from male or female mice, respectively using exon 2-specific primers. The wild-type *stella* transcript is reduced in *stella*$^{+/-}$ mice compared to *stella*$^{+/+}$ mice and absent in stell$^{-/-}$ mice. Gapdh was used as a control for equivalent quality and amount of RNA. –Rt, without reverse transcriptase; 0, water control.
Figure 16B:
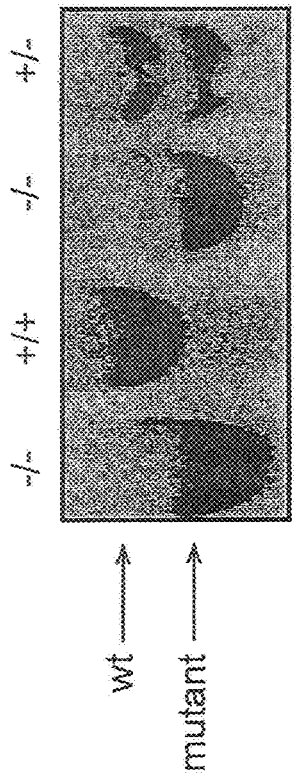
Figure 16C:
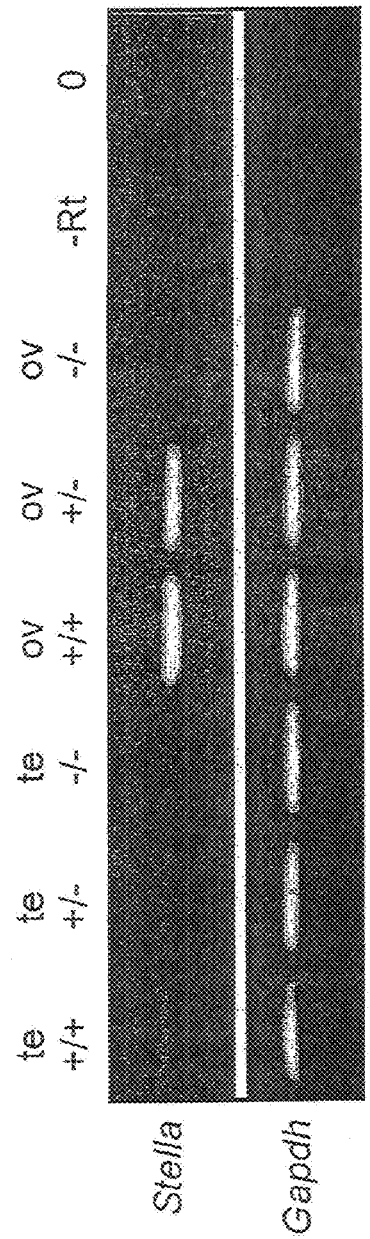

To begin to address functions of stella, we generated stella knockout (stellar) mice (FIG. 16). Matings between heterozygous (stella$^{+/-}$) mice on the 129/SvEv background resulted in the birth of 192 pups consisting of 56 (29.2%) wild-type, 81 (42.20%) stella$^{+/-}$ and 55 (28.6%) stella$^{-/-}$ mice, in the approximate mendelian ratio of 1:2:1. Therefore, stellar deficient mice are viable and survive at a normal rate.

As stella is detected in the founder PGCs, we examined stella$^{-/-}$ mice for any effects on development of germ cells. Examination of germ cells at E8.5 in mutant embryos by tissue non specific alkaline phosphatase (TNAP) activity, a marker of PGCs[16], revealed no significant differences in the numbers of PGCs compared to those in wild-type embryos (FIG. 17a). Similarly we found no effect on early gonadal PGCs (E11.5) in knockout embryos, detected by the germ cell marker SSEA1[17] (FIG. 17b). Furthermore, histological examination of testes and ovaries of adult mice showed no gross abnormalities in the development of gametes in stella mutant animals (FIG. 3h-m). Indeed stella$^{-/-}$ males showed normal fertility when mated with wild-type or heterozygous females. In mutant females, we detected oocytes at all stages of development and we found similar numbers of ovulated oocytes compared to those from control animals (stella$^{-/-}$ 8.6±1.0, n=9; wild-type or stella$^{+/-}$ 9.0±0.4, n=9), suggesting that the loss of stella has no gross effects on either germ cell determination or development.

Figure 18A:
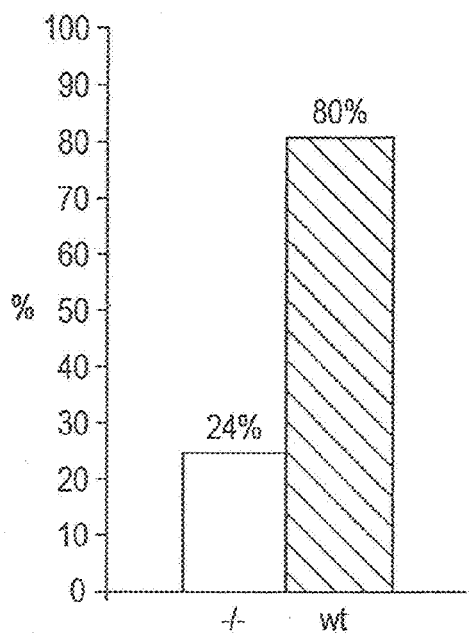
FIG. 18. Maternal effect of the *stella* knockout and onset of paternal expression of *stella* during preimplantation development. a, 80% of matings with wild-type males resulted in pregnancies of wild-type females, while in only 24% of the plugs *stella*$^{-/-}$ females became pregnant. b, From these pregnancies, the littersize was strongly reduced in knockouts compared to wild-type females. c-i, A *stella*-GFP reporter construct (c) was used to determine, when the paternal allele of *stella* starts to be expressed. Zygotic expression of the *stella*-GFP transgene begins at the 2-cell stage (E1.5; e, h) and continues during later stages (E2.5, 4-8 cell; f, i). d-f, GFP-fluorescence; g-i, brightfield merged with GFP-image; arrowheads, non-transgenic embryos; arrows, transgenic embryos. Scale bar in d (for d-i) =100 µm. j-l, Confocal section through a morula (E3.5) derived from a mating of a wild-type male with a *stella*$^{-/-}$ female stained with anti-*stella* antibody (j) and propidium iodide (k) (l, merge). Stella protein is made from the paternal allele, but not sufficient to rescue the observed phenotype. Scale bar in l (for j-l)=20 µm FIG. 19. Preimplantation development is perturbed without Stella. a, The percentage of embryos developing in vivo to the various stages are given for *stella*$^{-/-}$ (white bars) and wild-type or *stella*$^{+/-}$ (black bars) mothers, respectively. Total numbers of embryos examined at each timepoint are given in parentheses. Development of knockout-derived embryos starts to be affected from E1.5 onwards (2-cell stage) and only a low percentage reach the blastocyst stage by E3.5 (b) compared to wild-type-derived embryos (c). d-f, Distribution of stages of embryos cultured in vitro from E1.5 until E4.5 (timepoint of implantation). Similar as in vivo, most embryos from wild-type mothers (black bars) develop to blastocysts (f), while many embryos of *stella* knockout mothers (white bars) are delayed or show abnormal morphology (e). Total number of embryos examined in d: –/–mothers: 41, wt or +/–mothers: 36. Scale bar=100 µm.
Figure 18B:
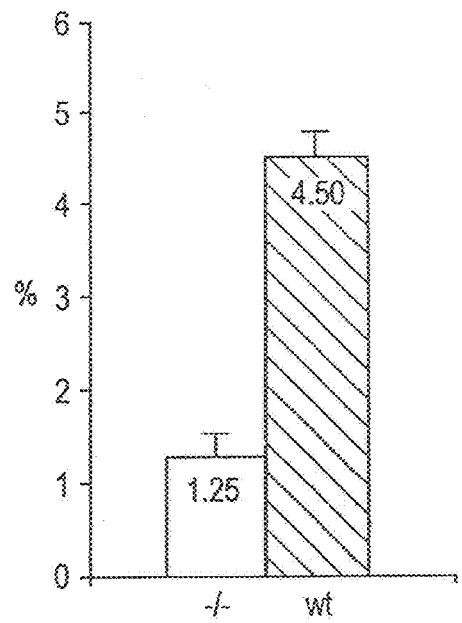
Figure 18C:
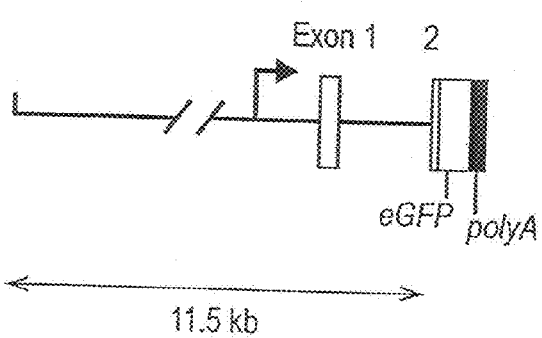

Next, we examined if development progressed normally from oocytes of stella$^{-/-}$ females that lack maternal inheritance of Stella. Despite the ovulation of normal numbers of Stella-deficient oocytes, female stella$^{-/-}$ mice displayed a strongly reduced fertility. When stella$^{-/-}$ females were mated with wild-type males, only a low percentage of matings (detected by vaginal plugs) (24%, FIG. 18a) resulted in full pregnancy and live young. Those females, which failed to become pregnant mated again after approximately 10 days, which reflects lack of embryo implantation in these females and the consequent resumption of the estrous cycle after a period of pseudopregnancy[18]. By contrast, 80% of wild-type females (littermate controls), became pregnant and produced litters following mating (FIG. 18a). Furthermore, even those stella$^{-/-}$ females that became pregnant, produced considerably smaller litters compared to the wild-type females (FIG. 18b). Preliminary results also show reduced fertility in an outbred strain (129SvEv/C57BL/6), although the effect is stronger in inbred 129Sv/Ev mice. This is consistent with previous reports that genetic background can alter the severity of knockout phenotypes[19], including defects in germ cell development[20,21]. These observations demonstrate that embryos derived from Stella-depleted oocytes are affected in development and that stella is a maternal effect gene, because the oocytes were fertilised by normal sperm from wild-type males.

Next we wanted to know, if the Stella protein in preimplantation embryos (FIG. 15)[8] is exclusively maternally inherited and therefore absent in embryos derived from stella$^{-/-}$ females, or if stella expression commences from the paternal allele after fertilisation by wild-type sperm. For this purpose, we made transgenic mice using a stella-GFP reporter transgene (FIG. 18c-i). When a stella-GFP transgenic male was mated with a non-transgenic female, we detected the transgene expression as early as the 2-cell stage (E1.5, FIGS. 18e,h), the time when the bulk of embryonic transcription and translation begins[22]. This indicates that the stella gene is transcribed very early during preimplantation development. We confirmed this observation by anti-Stella antibody stainings of E2.5 embryos (FIG. 18j-l), which were derived from mating a wild-type male with a stella$^{-/-}$ female. Therefore, Stella is clearly made in early embryos produced by matings between stella$^{-/-}$ females and wild-type males. But despite this, the majority of Stella-deficient oocytes did not develop normally to term, demonstrating that the onset of stella expression as early as the 2-cell stage from the paternal allele is not sufficient to fully rescue the observed maternal effect phenotype. By contrast, the maternally inherited Stella is sufficient for normal development, as stella$^{-/-}$ mice are born from heterozygous females mated with homozygous males at the same frequency as wild-type mice (see above).

Figure 19A:
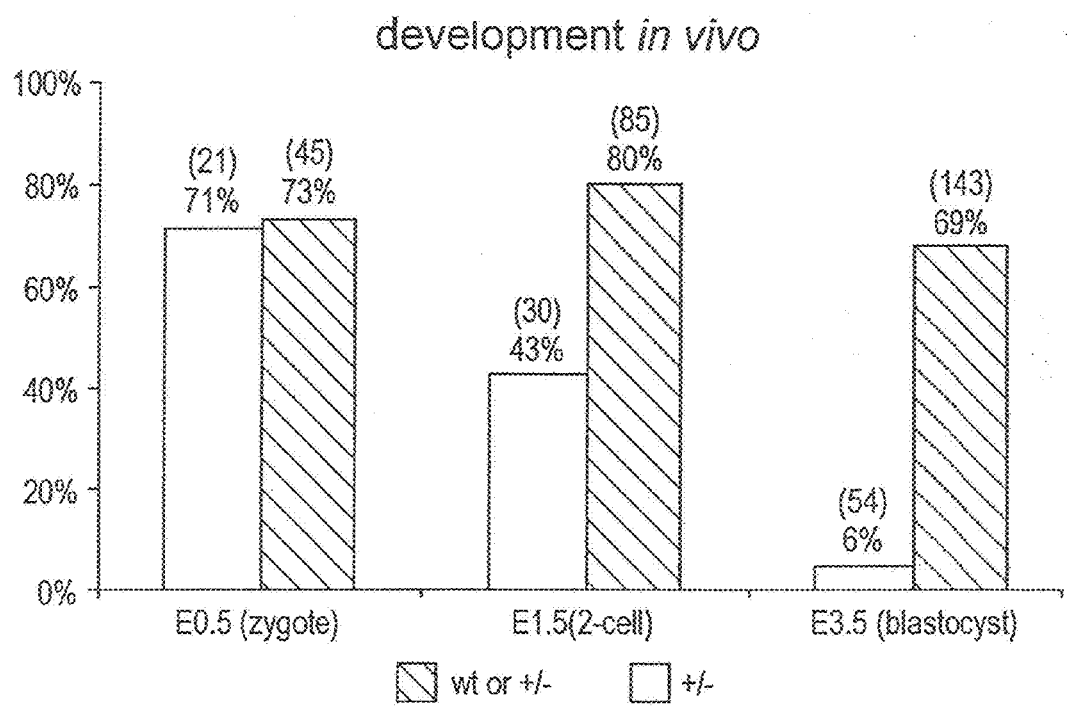
Figure 19D:
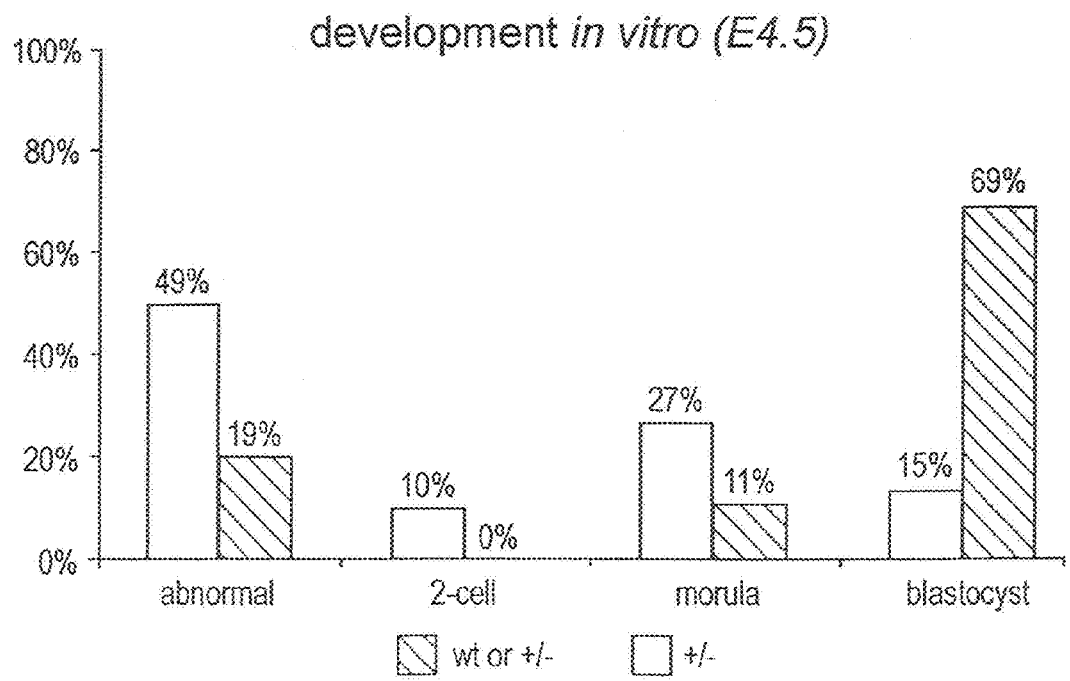
Figures 19B, 19C:
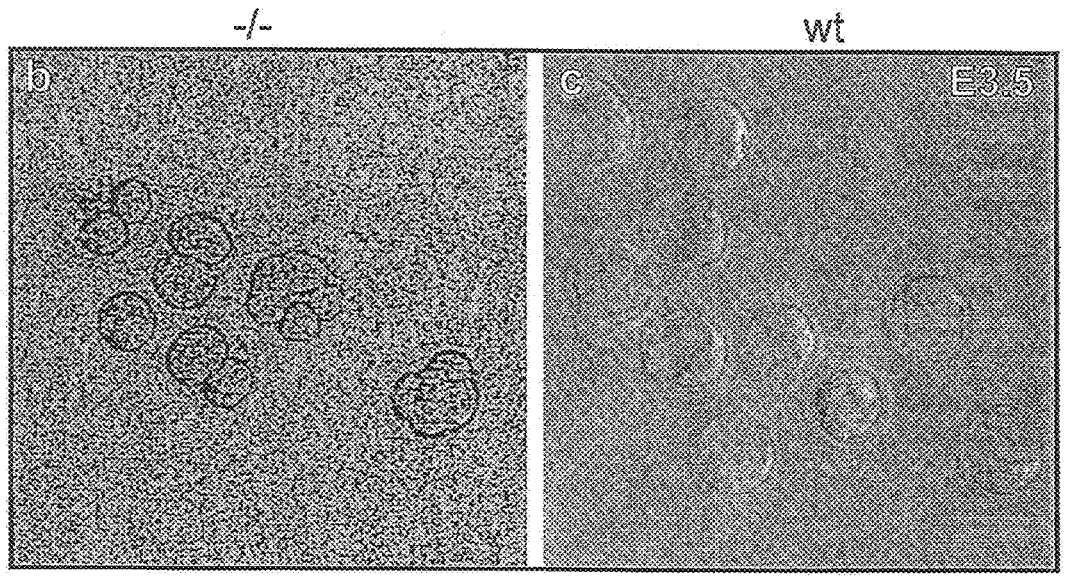
Figures 19E, 19F:
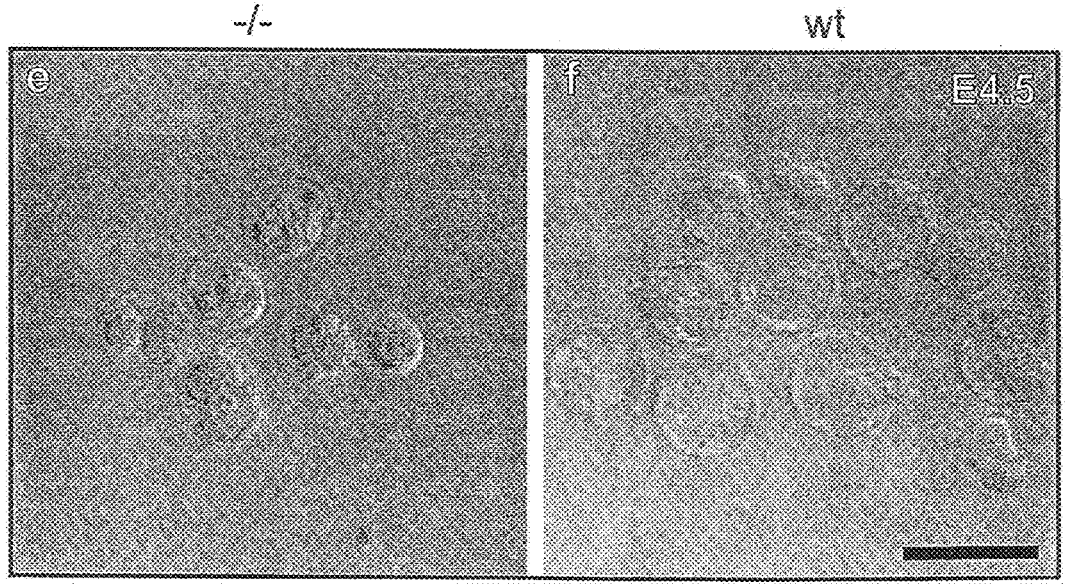

We then addressed the question concerning the embryonic stages at which the absence of Stella affects development. As we have so far not obtained any live young from matings between stellar males and stella$^{-/-}$ females, we examined embryos from these matings, and compared it with embryos from matings between wild-type or stella$^{-/-}$ males with wild-type or stella$^{+/-}$ females (FIG. 19). While fertilisation seems to proceed normally in oocytes from stella$^{-/-}$ females, the effects of lacking Stella become evident shortly thereafter, with progressively fewer embryos exhibiting normal development at each time point examined (FIG. 19a). The cumulative manifestation of developmental anomalies are starkly obvious at E3.5, when most of the embryos from controls (69%) reach the blastocyst stage, while only 6% of embryos in stella$^{-/-}$ mothers do so (FIG. 19 a-c). This observation was further supported by examination of similar embryos cultured in vitro for 3 days until E4.5, when only 15% of embryos from mutant oocytes reached the blastocyst stage compared to 69% for controls. 49% of mutant embryos were still at the single-cell stage, fragmenting or exhibiting asymmetric or abnormal cleavage. The remainder were found at various stages including 10% at the 2-cell stage and 27% at the morula stage (FIG. 5d-f). Since uterine receptivity for blastocyst implantation is restricted to late E3.5 to early E4.5, only those embryos that reach the blastocyst stage by that time can implant[23,24]. This is consistent with the observation that stella[−/−] females rarely become pregnant and when they do, they produce very small litters. In several cases, stella[−/−] females only become pseudopregnant and resume mating after 10 days, which is indicative of a lack of implanting blastocysts in these females[18].

In conclusion, we demonstrate that the maternal inheritance of Stella is needed for normal embryonic development. Depletion of Stella from the oocytes compromises this process, resulting in a progressive decline in the numbers of blastocyts, fewer implants and a poor yield of viable young. Stella is a basic protein with a SAP-like domain[25] and a splicing factor-like motif and therefore likely to have a role in chromosomal organisation or RNA metabolism. We propose to look for the interacting partners and the biochemical activity of the conserved domains of Stella to elucidate its role in early development. Despite a lack of gross abnormalities in germ cell development in stella[−/−] mice, we cannot rule out subtle effects. One possibility is functional redundancy through compensation by stella-related genes. There are several stella-like sequences in the mouse genome, although these are likely to be pseudogenes (data not shown). SETLLA is also expressed in human oocytes[10], where it is likely to play a similar role in early development as in mice. As the highest expression of SETLLA is in a human testicular germ cell tumour, this could serve as a diagnostic marker or be of therapeutic value in the future. The conservation of the syntenic chromosomal region harbouring SETLLA, together with NANOG and GDF3 on chromosome 12p is noteworthy as it is associated with pluripotency, teratocarcinomas and germ cell tumours in humans. The role of likely coordinated regulation of all key genes within the region may provide evolutionary insights into aspects of germ cell development and germ cell tumours, as well as on pluripotency and maternal effect genes.

References

Brady, G. and Iscove, N. N. (1993). Construction of cDNA libraries from single cells. *Methods Enzymol.* 225, 611-623.

Dulac, C. and Axel, R. (1995). A novel family of genes encoding putative pheromone receptors in mammals. *Cell* 83, 195-206.

Ginsburg, M., Snow, M. H. L., and McLaren, A. (1990). Primordial germ cells in the mouse embryo during gastrulation *Development* 110, 521-528.

Downs, K. M., and Davies, T. (1993). Staging of gastrulating mouse embryos by morphological landmarks in the dissecting microscope. *Development* 118, 1255-1266.

Lawson, K. A., Dunn, N. R., Roelen, B. A. J., Zeinstra, L. M., Davis, A. M., Wright, C. V. E., Korving, J. P. W. F. M., and Hogan, B. L. M. (1999). Bmp4 is required for the generation of primordial germ cells in the mouse embryo. *Genes & Dev.* 13, 424-436.

Yoem, Y. II., Fuhrmann, G., Ovitt, C. E., Brehm, A., Ohbo, K., Gross, M., Hubner, K., and Scholer, H. R. (1996). Germline regulatory element of Oct4 specific for the totipotent cycle of embryonal cells. *Development* 1996, 881-894.

1. Weismann, A. Das Keimplasma. Eine theorie der Vereburg. *Jenna Gustav Fischer* (1892).

2. Eddy, E. M. Germ plasm and the differentiation of the germ cell line. *Int Rev Cytol* 43, 229-80 (1975). 3. Seydoux, G. & Strome, S. Launching the germline in *Caenorhabditis elegans*: regulation of gene expression in early germ cells. *Development* 126, 3275-83. (1999).

4. Wylie, C. Germ cells. *Cell* 96, 165-74. (1999).

5. Lawson, K. A. et al. Bmp4 is required for the generation of primordial germ cells in the mouse embryo. *Genes Dev* 13, 424-36. (1999).

6. Lawson, K. A. & Hage, W. J. Clonal analysis of the origin of primordial germ cells in the mouse. *Ciba Found Symp* 182, 68-84 (1994).

7. Tam, P. P. & Zhou, S. X. The allocation of epiblast cells to ectodermal and germ-line lineages is influenced by the position of the cells in the gastrulating mouse embryo. *Dev Biol* 178, 124-32. (1996).

8. Yoshimizu, T., Obinata, M. & Matsui, Y. Stage-specific tissue and cell interactions play key roles in mouse germ cell specification. *Development* 128, 481-90. (2001).

9. McLaren, A. Signaling for germ cells. *Genes Dev* 13, 373-6. (1999).

10. Ying, Y., Liu, X. M., Marble, A., Lawson, K. A. & Zhao, G. Q. Requirement of Bmp8b for the generation of primordial germ cells in the mouse. *Mol Endocrinol* 14, 1053-63. (2000).

11. Ying, Y., Qi, X. & Zhao, G. Q. Induction of primordial germ cells from murine epiblasts by synergistic action of BMP4 and BMP8B signaling pathways. *Proc Natl Acad Sci USA* 98, 7858-7862. (2001).

12. Ying, Y. & Zhao, G. Q. Cooperation of endoderm-derived BMP2 and extraembryonic ectoderm-derived BMP4 in primordial germ cell generation in the mouse. *Dev Biol* 232, 484-92. (2001).

13. Chiquoine, A. D. The identification, origin and migration of the primordial germ cells in the mouse embryo. *Anat Rec* 118, 135-146 (1954).

14. Ginsburg, M., Snow, M. H. & McLaren, A. Primordial germ cells in the mouse embryo during gastrulation. *Development* 110, 521-8. (1990).

15. MacGregor, G. R, Zambrowicz, B. P. & Soriano, P. Tissue non-specific alkaline phosphatase is expressed in both embryonic and extraembryonic lineages during mouse embryogenesis but is not required for migration of primordial germ cells. *Development* 121, 1487-96. (1995).

16. Nichols, J. et al. Formation of pluripotent stem cells in the mammalian embryo depends on the POU transcription factor Oct4. *Cell* 95, 379-91. (1998).

17. Pesce, M., Gross, M. K. & Scholer, H. R. In line with our ancestors: Oct-4 and the mammalian germ. *Bioessays* 20, 722-32. (1998).

18. Yeom, Y. I. et al. Germline regulatory element of Oct-4 specific for the totipotent cycle of embryonal cells. *Development* 122, 881-94. (1996).

19. Downs, K. M. & Davies, T. Staging of gastrulating mouse embryos by morphological landmarks in the dissecting microscope. *Development* 118, 1255-66. (1993).

20. Brady, G. & Iscove, N. N. Construction of cDNA libraries from single cells. *Methods Enzymol* 225, 611-23 (1993).

21. Dulac, C. & Axel, R. A novel family of genes encoding putative pheromone receptors in mammals. *Cell* 83, 195-206. (1995).

22. Frohman, M. A., Boyle, M. & Martin, G. R. Isolation of the mouse Hox-2.9 gene; analysis of embryonic expression suggests that positional information along the anterior-posterior axis is specified by mesoderm. *Development* 110, 589-607. (1990).

23. Deblandre, G. A. et al. Expression cloning of an interferon-inducible 17-kDa membrane protein implicated in the control of cell growth. *J Biol Chem* 270, 23860-6. (1995).

24. Friedman, R. L., Manly, S. P., McMahon, M., Kerr, I. M. & Stark, G. R. Transcriptional and posttranscriptional regulation of interferon-induced gene expression in human cells. *Cell* 38, 745-55. (1984).

25. Evans, S. S., Collea, R. P., Leasure, J. A. & Lee, D. B. IFN-alpha induces homotypic adhesion and Leu-13 expression in human B lymphoid cells. *J Immunol* 150, 73647. (1993).

26. Evans, S. S., Lee, D. B., Han, T., Tomasi, T. B. & Evans, R. L. Monoclonal antibody to the interferon-inducible protein Leu-13 triggers aggregation and inhibits proliferation of leukemic B cells. *Blood* 76, 2583-93. (1990).

27. Aravind, L. & Koonin, E. V. SAP—a putative DNA-binding motif involved in chromosomal organization. *Trends Biochem Sci* 25, 112-4. (2000).

28. Gurdon, J. B., Lemaire, P. & Kato, K. Community effects and related phenomena in development. *Cell* 75, 831-4. (1993).

29. Reid, L. E. et al. A single DNA response element can confer inducibility by both alpha- and gamma-interferons. *Proc Natl Acad Sci USA* 86, 840-4. (1989).

30. Kita, M. et al. [Expression of cytokines and interferon-related genes in the mouse embryo]. *C R Seances Soc Biol Fil* 188, 593-600 (1994).

31. Gomperts, M., Garcia-Castro, M., Wylie, C. & Heasman, J. Interactions between primordial germ cells play a role in their migration in mouse embryos. *Development* 120, 135-41. (1994).

32. Herrmann, B. G., Labeit, S., Poustca, A., King, T. R. & Lehrach, H. Cloning of the T gene required in mesoderm formation in the mouse. *Nature* 343, 617-22. (1990).

33. Herrmann, B. G. Expression pattern of the Brachyury gene in whole-mount TWis/TWis mutant embryos. *Development* 113, 913-17

34. Crossley, P. H. & Martin, G. R. The mouse Fgf8 gene encodes a family of polypeptides and is expressed in regions that direct outgrowth and patterning in the developing embryo. *Development* 121, 439-51. (1995).

35. Barnes, J. D., Crosby, J. L., Jones, C. M., Wright, C. V. & Hogan, B. L. Embryonic expression of Lim-1, the mouse homolog of Xenopus Xlim-1, suggests a role in lateral mesoderm differentiation and neurogenesis. *Dev Biol* 161, 168-78. (1994).

36. Fujii, T. et al. Expression patterns of the murine LIM class homeobox gene lim1 in the developing brain and excretory system. *Dev Dyn* 199, 73-83. (1994).

37. Bastian, H. & Gruss, P. A murine even-skipped homologue, Evx 1, is expressed during early embryogenesis and neurogenesis in a biphasic manner. *Embo J* 9, 1839-52. (1990).

38. Rogers, M. B., Hosler, B. A. & Gudas, L. J. Specific expression of a retinoic acid-regulated, zinc-finger gene, Rex-1, in preimplantation embryos, trophoblast and spermatocytes. *Development* 113, 815-24. (1991).

39. Sutton, J. et al. Genesis, a winged helix transcriptional repressor with expression restricted to embryonic stem cells. *J Biol Chem* 271, 23126-33. (1996).

40. Cox, D. N. et al. A novel class of evolutionarily conserved genes defined by piwi are essential for stem cell self-renewal. *Genes Dev* 12, 3715-27. (1998).

41. Fujiwara, Y. et al. Isolation of a DEAD-family protein gene that encodes a murine homolog of *Drosophila vasa* and its specific expression in germ cell lineage. *Proc Natl Acad Sci USA* 91, 12258-62. (1994).

42. Dixon, K. E. Evolutionary aspects of primordial germ cell formation. *Ciba Found Symp* 182, 92-110 (1994).

43. Mahowald, A. P. Assembly of the *Drosophila* germ plasm. *Int Rev Cytol* 203, 187-213 (2001).

44. Nieuwkoop, P. D. & Satasurya, L. A. Primordial germ cells in the chordates. *Cambridge University Press, Cambridge, UK* (1979).

45. Johnson, A. D., Bachvarova, R. F., Drum, M. & Masi, T. Expression of axolotl daz1 ma, a marker of germ plasm: widespread maternal ma and onset of expression in germ cells approaching the gonad. *Dev Biol* 234, 402-15. (2001).

46. Johnson, A. D., Bachvarova, R. F., Masi, T. & Drum, M. Expression of Vasa and Daz-like genes demonstrate that Axolotl primordial germ cells (PGCs) are not predetermined. *Germ cells* Cold Spring harbor laboratory, 61 (2000).

47. Toyooka, Y. et al. Expression and intracellular localization of mouse Vasa-homologue protein during germ cell development. *Mech Dev* 93, 139-49. (2000).

48. Saitou, M. et al. Occludin-deficient embryonic stem cells can differentiate into polarized epithelial cells bearing tight junctions. *J Cell Biol* 141, 397-408. (1998).

49. Henrique, D. et al. Expression of a Delta homologue in prospective neurons in the chick. *Nature* 375, 787-90. (1995).

50. Wilkinson, D. G. & Nieto, M. A. Detection of messenger RNA by in situ hybridization to tissue sections and whole mounts. *Methods Enzymol* 225, 361-73 (1993).

51. Winnier, G., Blessing, M., Labosky, P. A. & Hogan, B. L. Bone morphogenetic protein-4 is required for mesoderm formation and patterning in the mouse. *Genes Dev* 9, 2105-16. (1995).

REFERENCES FOR EXAMPLES 11 TO 20

1. K A Lawson, W J Hage: Clonal analysis of the origin of primordial germ cells in the mouse. Germline development. In *Wiley, Chichester (Ciba Foundation Symposium 182)* 1994, 68-91

2. A McLaren: Signaling for germ cells. *Genes Dev* 1999, 13: 373-376

3. K A Lawson, N R Dunn, B A J Roelm, L M Zeinstra, A M Davies, C V E Wright, J P W F M Korving, B L M Hogan: Bmp4 is required for the generation of primordial germ cells in the mouse embryo. *Genes Dev* 1999, 13: 424-436

4. Y Ying, X M Lui, A Marble, K A Lawson, G Q Zhao: Requirement of Bmp8b for the generation of primordial germ cells in the mouse. *Mol Endocrinol* 2000, 14: 1053-1063

5. H Chang, M M Matzuk: Smad5 is required for mouse primordial germ cell development *Mech Dev* 2001, 104: 61-67

6. K D Tremblay, N R Dunn, E J Robertson: Mouse embryos lacking Smad1 signals display defects in extraembryonic tissues and germ cell formation. *Development* 2001, 128: 3609-3621

7. Y Ying, G Q Zhao: Cooperation of endoderm-derived BMP2 and extraembryonic ectoderm-derived BMP4 in primordial germ cell generation in the mouse. *Dev Biol* 2001, 232 (2): 484492

8. M Saitou, S C Barton, M A Surani: A molecular programme for the specification of germ cell fate in mice. *Nature* 2002, 418: 293-300

9. M Ginsburg, M H L Snow, A McLaren: Primordial germ cells in the mouse embryo during gastrulation. *Development* 1990, 110: 521-528

10. M Sato, T Kimura, K Kurokawa, Y Fujita, K Abe, M Masuhara, T Yasunaga, A Ryo, M Yamamoto, T Nakano: Identification of PGC7, a new gene expressed specifically in preimplantation embryos and germ cells. *Mech Dev* 2002, 113: 91-94

11. A R Lewin, L E Reid, M McMahon, G R Stark, I M Kerr: Molecular analysis of a human interferon-inducible gene family. *Eur J Biochem* 1991, 199: 417-423
12. R L Friedman, S P Manley, M Mcahon, I M Kerr, G R Stark: Transcriptional and posttranscriptional regulation of interferon-induced gene expression in human cells. *Cell* 1984, 38: 745-755
13. J M Kelly, C S Gilbert, G R Stark, I M Kerr: Differential regulation of interferon-induced mRNAs and c-myc mRNA by alpha- and gamma-interferons. *Eur J Biochem* 1985, 153: 367-371
14. S S Evans, D B Lee, T Han, T B Tomasi, R L Evans: Monoclonal antibody to the interferon-inducible protein Leu-13 triggers aggregation and inhibits proliferation of leukemic B cells. *Blood* 1990, 76 (12): 2583-2593
15. S S Evans, R P Collea, J A Leasure, D B Lee: IFN-a induces homotypic adhesion and Leu-13 expression in human B lymphoid cells. *J Immunol* 1993, 150: 736-747
16. D J Hayzer, E Brinson, M S Runge: A rat beta-interferon-induced mRNA: sequence characterization. *Gene* 1992, 117 (2): 227-228
17. J K Pru, K J Austin, A L Haas, T R Hansen: Pregnancy and interferon-tau upregulate gene expression of members of the 1-8 family in the bovine uterus. *Biol Reprod* 2001, 65 (5): 1471-1480
18. L E Reid, A H Brasnett, C S Gilbert, A C G Porter, D R Gewert, G R Stark, I M Kerr: A single DNA response elemnt can confer inducibility by both alpha- and gamma-interferons. *Proc Natl Acad Sci USA* 1989, 86: 840-844
19. G R Stark, I M Kerr, B R G Williams, R H Silverman, R D Schreiber: How cells respond to interferons. *Annu Rev Biochem* 1998, 67: 227-264
20. D P Barlow, B J Randle, D C Burke: Interferon synthesis in the early post-implantation mouse embryo. *Differentiation* 1984, 27: 229-235
21. M Kita, K Tanaka, K Shinmura, Y Tanaka, Y Liu, J Imanishi: Expression of cytokines and interferon-related genes in the mouse embryo. *C.R. Seances Soc. Biol. Fil.* 1994, 188 (5-6): 593-600.
22. K M Downs, T Davies: Staging of gastrulating mouse embryos by morphological landmarks in the dissecting microscope. *Development* 1993, 118: 1255-1266
23. D G Wilkinson, M A Nieto: Detection of messenger RNA by in situ hybridisation to tissue sections and whole mounts. *Methods Enzymol* 1993, 225: 361-373
24. D Henrique, J Adam, A Myat, A Chitnis, J Lewis, D Ish-Horowicz: Expression of a Delta homologue in prospective neurons in the chick. *Nature* 1995, 375: 787-790
25. G Brady, N N Iscove: Construction of cDNA libraries from single cells. *Methods Enzymol* 1993, 225: 611-623

REFERENCES FOR EXAMPLES 21 TO 25

1. Surani, M. A. Reprogramming of genome function through epigenetic inheritance. *Nature* 414, 122-8 (2001).
2. Wu, X. et al. Zygote arrest 1 (Zar1) is a novel maternal-effect gene critical for the oocyte-to-embryo transition. *Nat Genet* 33, 187-91 (2003).
3. Tong, Z. B. et al. Mater, a maternal effect gene required for early embryonic development in mice. *Nat Genet* 26, 267-8 (2000).
4. Howell, C. Y. et al. Genomic imprinting disrupted by a maternal effect mutation in the Dnmt1 gene. *Cell* 104, 829-38 (2001).
5. Christians, E., Davis, A. A., Thomas, S. D. & Benjamin, I. J. Maternal effect of Hsf1 on reproductive success. *Nature* 407, 693-4 (2000).
6. Gurtu, V. E. et al. Maternal effect for DNA mismatch repair in the mouse. *Genetics* 160, 271-7 (2002).
7. Burns, K. H. et al. Roles of NPM2 in chromatin and nucleolar organization in oocytes and embryos. *Science* 300, 633-6 (2003).
8. Sato, M. et al. Identification of PGC7, a new gene expressed specifically in preimplantation embryos and germ cells. *Mech Dev* 113, 91-4 (2002).
9. Saitou, M., Barton, S. C. & Surani, M. A. A molecular programme for the specification of germ cell fate in mice. *Nature* 418, 293-300 (2002).
10. Goto, T. et al. Identification and characterisation of known and novel transcripts expressed during the final stages of human oocyte maturation. *Mol Reprod Dev* 62, 13-28 (2002).
11. Looijenga, L. H. et al. Role of gain of 12p in germ cell tumour development. *Apmis* 111, 161-71; discussion 172-3 (2003).
12. Mitsui, K. et al. The Homeoprotein Nanog Is Required for Maintenance of Pluripotency in Mouse Epiblast and ES Cells. *Cell* 113, 631-42 (2003).
13. Chambers, I. et al. Functional expression cloning of nanog, a pluripotency sustaining factor in embryonic stem cells. *Cell* 113, 643-55 (2003).
14. Caricasole, A. A. et al. Human growth-differentiation factor 3 (hGDF3): developmental regulation in human teratocarcinoma cell lines and expression in primary testicular germ cell tumours. *Oncogene* 16, 95-103 (1998).
15. Spellman, P. T. & Rubin, G. M. Evidence for large domains of similarly expressed genes in the Drosophila genome. *J Biol* 1, 5 (2002).
16. Ginsburg, M., Snow, M. H. & McLaren, A. Primordial germ cells in the mouse embryo during gastrulation. *Development* 110, 521-8 (1990).
17. Fox, N., Damjanov, I., Martinez-Hernandez, A., Knowles, B. B. & Solter, D. Immunohistochemical localization of the early embryonic antigen (SSEA-1) in postimplantation mouse embryos and fetal and adult tissues. *Dev Biol* 83, 391-8 (1981).
18. Johnson, M. H. & Everitt, B. J. Essential reproduction, xi, 377 (Blackwell Scientific, Oxford, 1988).
19. Montagutelli, X. Effect of the genetic background on the phenotype of mouse. mutations. *J Am Soc Nephrol* 11 Suppl 16, S101-5 (2000).
20. Lawson, K. A. et al. Bmp4 is required for the generation of primordial germ cells in the mouse embryo. *Genes Dev* 13, 424-36 (1999).
21. Winnier, G., Blessing, M., Labosky, P. A. & Hogan, B. L. Bone morphogenetic protein-4 is required for mesoderm formation and patterning in the mouse. *Genes Dev* 9, 2105-16 (1995).
22. Nothias, J. Y., Majumder, S., Kaneko, K. J. & DePamphilis, M. L. Regulation of gene expression at the beginning of mammalian development. *J Biol Chem* 270, 22077-80 (1995).
23. Rugh, R. *The mouse: Its Reproduction and Development*, (Oxford University Press, Oxford England; New York, 1990).
24. McLaren, A. & Michie, D. Studies on the transfer of fertilized mouse eggs to uterine foster-mothers. *J Exp Biol* 33, 394-416 (1956).
25. Aravind, L. & Koonin, E. V. SAP—a putative DNA-binding motif involved in chromosomal organization. *Trends Biochem Sci* 25, 112-4 (2000).
26. Chang, H. & Matzuk, M. M. Smad5 is required for mouse primordial germ cell development. *Mech Dev* 104, 61-7 (2001).

27. Fukuda, M. et al. CRM1 is responsible for intracellular transport mediated by the nuclear export signal. *Nature* 390, 308-11 (1997).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. An isolated antibody capable of binding specifically to an extracellular domain of human *Fragilis*, said human *Fragilis* having the amino acid sequence as shown in SEQ ID NO:6.

2. The antibody of claim 1, wherein the antibody binds to the N-terminal domain of said human *Fragilis*.

3. The antibody of claim 1, wherein the antibody binds to the C-terminal domain of said human *Fragilis*.

4. The antibody of claim 1, wherein the antibody comprises an effector protein.

5. The antibody of claim 1, wherein the antibody further comprises a label.

6. The antibody of claim 5, wherein the label is selected from the group consisting of a radioactive label, a radioopaque label, a metal particle, a fluorescent label, a luminescent label, and a label which is visualisable on tissue samples.

7. The antibody of claim 1, wherein the antibody is obtained from at least one of animal serum, cell culture, and recombinant DNA technology.

8. The antibody of claim 1, wherein the antibody is a monoclonal antibody.

9. The antibody of claim 1, wherein the antibody is a polyclonal antibody.

10. The antibody of claim 1, wherein the antibody comprises an antibody fragment selected from the group consisting of an Fv, ScFv, Fab', and F(ab')$_2$.

11. A method of producing the antibody of claim 1, the method comprising: culturing a host cell which has been transformed with a hybrid vector comprising an expression cassette comprising a promoter operably linked to a first DNA sequence encoding a signal peptide linked in the proper reading frame to a second DNA sequence encoding the antibody; and isolating the antibody.

12. A method of producing the antibody of claim 1, the method comprising:

immunizing mice with at least one of cells expressing human *Fragilis*, one or more human *Fragilis* polypeptides, or antigenic fragments of human *Fragilis* polypeptides;

taking spleen cells from the immunized mice;

fusing the spleen cells with myeloma cells to form hybridoma cells;

expanding the hybridoma cells;

injecting hybridoma cells into histocompatible mammals to cause growth of antibody-producing tumours;

taking ascitic fluid from the mammals; and isolating the antibody from the ascitic fluid of the mammals.

13. A The method of claim 12, further comprising, prior to the injecting step, priming the mammals with a hydrocarbon.

14. A The method of claim 12, further comprising concentrating the antibody.

15. A method of producing the antibody of claim 1, the method comprising:

producing the antibody of claim 1 using a method selected from the group consisting of bacterial or preferably manimalian cell culture; and screening cell culture supematants for the antibody.

16. A method of producing a hybridoma cell line secreting the antibody of claim 1, the method comprising:

immunizing a mammal with at least one of cells expressing human *Fragilis*, one or more human *Fragilis* polypeptides, or antigenic fragments of human *Fragilis* polypeptides;

isolating antibody-producing cells from the immunized mammal;

fusing the antibody-producing cells of the immunized mammal with cells of a myeloma cell line to form hybridoma cells; and selecting hybridoma cells secreting the antibody.

* * * * *

SEQUENCE LISTING

```
<160> NUMBER OF SEQ ID NOS: 67

<210> SEQ ID NO 1
<211> LENGTH: 617
<212> TYPE: DNA
<213> ORGANISM: Mus musculus

<400> SEQUENCE: 1
gccgcagaaa gggcagaccc gcagcgcgct ccatcctttg ccctccagtg ctgcctttgc      60
tccgcaccat gaaccacact tctcaagcct tcatcaccgc tgccagtgga ggacagcccc     120
caaactacga aagaatcaag gaagaatatg aggtggctga gatgggggca ccgcacggat     180
cggcttctgt cagaactact gtgatcaaca tgcccagaga ggtgtcggtg cctgaccatg     240
tggtctggtc cctgttcaat acactcttca tgaacttctg ctgcctgggc ttcatagcct     300
atgcctactc cgtgaagtct agggatcgga agatggtggg tgatgtgact ggagcccagg     360
cctacgcctc cactgctaag tgcctgaaca tcagcacctt ggtcctcagc atcctgatgg     420
ttgttatcac cattgttagt gtcatcatca ttgttcttaa cgctcaaaac cttcacactt     480
aatagaggat tccgacttcc ggtcctgaag tgcttcaccc tccgcagctg cgtccctcct     540
tgcccctccc tacacgcagg tgtaacactc atttatctat ccacagtgga ttcaataaag     600
tgcacttgat aaccacc                                                    617

<210> SEQ ID NO 2
<211> LENGTH: 823
<212> TYPE: DNA
<213> ORGANISM: Mus musculus

<400> SEQUENCE: 2
ggatcacaga ctgactgcta attgggtctt ggttttaggt cttttcaaag actaagcaat      60
cttgttccga gctagctttt gaggcttctg cccatcgcat cgccatggag gaaccatcag     120
agaaagtcga cccaatgaag gaccctgaaa ctcctcagaa gaaagatgaa gaggacgctt     180
tggatgatac agacgtccta caaccagaaa cactagtaaa ggtcatgaaa aagctaaccc     240
taaaccccgg tgtcaagcgg tccgcacgcc ggcgcagtct acggaaccgc attgcagccg     300
tacctgtgga gaacaagagt gaaaaaatcc ggagggaagt tcaaagcgcc tttcccaaga     360
gaagggtccg cactttgttg tcggtgctga agaccctat agcaaagatg agaagacttg     420
ttcggattga gcagagacaa aaaaggctcg aaggaaatga gtttgaacgg gacagtgagc     480
cattcagatg tctctgcact ttctgccatt atcaaagatg ggatccctct gagaatgcga     540
aaatcgggaa gaattaggag cttacattgt acgctgccct ggctgtcgac gatgccgcac     600
```

```
agcagatgtg aaagctattt tttgtttaag attaaacttt ttctggtgct gggaaatctt     660
aacttgttaa cctttaaatt gtagatagga tgcacaacga tccagattta tgtgaagttt    720
agaagcctca agctgtgagg cccagggctg aggaataaag taaatagaat ttggagtatg    780
tacgttctaa tttccagaaa tttgtaataa aagcattttt gtt                      823
```

<210> SEQ ID NO 3
<211> LENGTH: 1040
<212> TYPE: DNA
<213> ORGANISM: Homo sapiens

<400> SEQUENCE: 3

```
agcaatttga ggctctgtca tcagtttctg ctacgtttca agatcctgg agaagcctag      60 tgttgtgtca agacgccgat ggacccatca cagtttaatc caacctacat cccagggtct    120
ccacaaatgc tcaccgaaga aaattcccgg gacgattcag gggcctctca aatctcctcc    180
gagacgttga taaagaacct tagtaacttg actatcaacg ctagtagcga atctgtttcc    240
cctctatcgg aagctttact ccgtcgagag tctgtaggag cagcagtcct cagggaaatc    300
gaagatgagt ggctttacag caggagagga gtaagaacat tgctgtctgt gcagagagaa    360
aagatggcaa gattgagata catgttactc ggcggagttc gtacgcatga agaagacca     420 acaaacaagg agcctaaggg agttaagaag gaatcaagac cattcaaatg tccctgcagt    480
ttctgcgtgt ctaatggatg ggatccttct gagaatgcta aatagggaa tcaagacacc     540 aagccacttc agccataaat cttattcttg cacctttttt tcttggtagt aattttatat    600
agcaggttga gaaagctact ctatgctagt atagactata caccaataat tttgataatg    660
agttctagga tgtattttc ttgtatcttt ttcttcctac tatgatacta gtaattcata     720
agggatctgt gtaatctgaa tgtatttgaa taactttagc tctactgttt gatttgaccc    780
aaagaagcca agatgatata agtattccca tgtgtcttag aagcccaaag tcagtgagat    840
gaaacccaac atcaagaaat tgaagcaaag ttacttatgg ataaagaaag cattaggtag    900
ttgggctata gcataattag attttctggc tttcaaaaat ttggattgca atcacagcaa    960
actttgttat tttacagtt ttcagtacaa aagtgtttat atagaaacaa taaagttgac     1020
atttgagtac cttttaaaaa                                                 1040
```

<210> SEQ ID NO 4
<211> LENGTH: 159
<212> TYPE: PRT
<213> ORGANISM: Homo sapiens

<400> SEQUENCE: 4

```
Met Asp Pro Ser Gln Phe Asn Pro Thr Tyr Ile Pro Gly Ser Pro Gln
1               5                   10                  15

Met Leu Thr Glu Glu Asn Ser Arg Asp Asp Ser Gly Ala Ser Gln Ile
            20                  25                  30

Ser Ser Glu Thr Leu Ile Lys Asn Leu Ser Asn Leu Thr Ile Asn Ala
        35                  40                  45

Ser Ser Glu Ser Val Ser Pro Leu Ser Glu Ala Leu Leu Arg Arg Glu
    50                  55                  60

Ser Val Gly Ala Ala Val Leu Arg Glu Ile Glu Asp Glu Trp Leu Tyr
65                  70                  75                  80

Ser Arg Arg Gly Val Arg Thr Leu Leu Ser Val Gln Arg Glu Lys Met
                85                  90                  95
```

Ala Arg Leu Arg Tyr Met Leu Leu Gly Gly Val Arg Thr His Glu Arg
            100                 105                 110

Arg Pro Thr Asn Lys Glu Pro Lys Gly Val Lys Lys Glu Ser Arg Pro
        115                 120                 125

Phe Lys Cys Pro Cys Ser Phe Cys Val Ser Asn Gly Trp Asp Pro Ser
    130                 135                 140

Glu Asn Ala Arg Ile Gly Asn Gln Asp Thr Lys Pro Leu Gln Pro
145                 150                 155

<210> SEQ ID NO 5
<211> LENGTH: 653
<212> TYPE: DNA
<213> ORGANISM: Homo sapiens

<400> SEQUENCE: 5
tcccggtaac ccgatcaccg ctggtcacca tgaaccacat tgtgcaaacc ttctctcctg      60
tcaacagcgg ccagcctccc aactacgaga tgctcaagga ggagcaggaa gtggctatgc     120
tgggggtgcc ccacaaccct gctcccccga tgtccaccgt gatccacatc cgcagcgaga     180
cctccgtgcc tgaccatgtg gtctggtccc tgttcaacac cctcttcatg aacacctgct     240
gcctgggctt catagcattc gcgtactccg tgaagtctag ggacaggaag atggttggcg     300
acgtgaccgg ggcccaggcc tatgcctcca ccgccaagtg cctgaacatc tgggccctga     360
ttttgggcat cttcatgacc attctgctca tcatcatccc agtgttggtc gtccaggccc     420
agcgatagat caggaggcat cattgaggcc aggagctctg cccgtgacct gtatcccacg     480
tactctatct tccattcctc gccctgcccc cagaggccag gagctctgcc cttgacctgt     540
attccactta ctccacctcc cattcctcgc cctgtcccca cagccgagtc ctgcatcagc     600 ccttttatcct cacacgcttt tctacaatgg cattcaataa agtgtatatg ttt           653

<210> SEQ ID NO 6
<211> LENGTH: 132
<212> TYPE: PRT
<213> ORGANISM: Homo sapiens

<400> SEQUENCE: 6

Met Asn His Ile Val Gln Thr Phe Ser Pro Val Asn Ser Gly Gln Pro
1               5                   10                  15

Pro Asn Tyr Glu Met Leu Lys Glu Glu Gln Val Ala Met Leu Gly
            20                  25                  30

Val Pro His Asn Pro Ala Pro Pro Met Ser Thr Val Ile His Ile Arg
        35                  40                  45

Ser Glu Thr Ser Val Pro Asp His Val Val Trp Ser Leu Phe Asn Thr
    50                  55                  60

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
            100                 105                 110

Gly Ile Phe Met Thr Ile Leu Leu Ile Ile Ile Pro Val Leu Val Val
        115                 120                 125

Gln Ala Gln Arg
    130

<210> SEQ ID NO 7
<211> LENGTH: 677
<212> TYPE: DNA
<213> ORGANISM: Homo sapiens

<400> SEQUENCE: 7

```
tgagaaactg aaacgacagg ggaaaggagg tctcactgag caccgtccca gcatccggac      60
accacagcgg cccttcgctc cacgcagaaa accacacttc tcaaaccttc actcaacact     120
tccttcccca aagccagaag atgcacaagg aggaacatga ggtggctgtg ctgggggcac     180
cccccagcac catccttcca aggtccaccg tgatcaacat ccacagcgag acctccgtgc     240
ccgaccatgt cgtctggtcc ctgttcaaca ccctcttctt gaactggtgc tgtctgggct     300
tcatagcatt cgcctactcc gtgaagtcta gggacaggaa gatggttggc gacgtgaccg     360
ggcccaggc ctatgcctcc accgccaagt gcctgaacat ctgggccctg attctgggca     420
tcctcatgac cattggattc atcctgtcac tggtattcgg ctctgtgaca gtctaccata     480
ttatgttaca gataatacag gaaaaacggg gttactagta gccgcccata gcctgcaacc     540
tttgcactcc actgtgcaat gctggccctg cacgctgggg ctgttgcccc tgccccttg      600
gtcctgcccc tagatacagc agtttatacc cacacacctg tctacagtgt cattcaataa     660
agtgcacgtg cttgtga                                                   677
```

<210> SEQ ID NO 8
<211> LENGTH: 125
<212> TYPE: PRT
<213> ORGANISM: Homo sapiens

<400> SEQUENCE: 8

```
Met His Lys Glu Glu His Glu Val Ala Val Leu Gly Ala Pro Pro Ser
  1               5                  10                  15

Thr Ile Leu Pro Arg Ser Thr Val Ile Asn Ile His Ser Glu Thr Ser
             20                  25                  30

Val Pro Asp His Val Val Trp Ser Leu Phe Asn Thr Leu Phe Leu Asn
         35                  40                  45

Trp Cys Cys Leu Gly Phe Ile Ala Phe Ala Tyr Ser Val Lys Ser Arg
     50                  55                  60

Asp Arg Lys Met Val Gly Asp Val Thr Gly Ala Gln Ala Tyr Ala Ser
 65                  70                  75                  80

Thr Ala Lys Cys Leu Asn Ile Trp Ala Leu Ile Leu Gly Ile Leu Met
                 85                  90                  95

Thr Ile Gly Phe Ile Leu Ser Leu Val Phe Gly Ser Val Thr Val Tyr
            100                 105                 110

His Ile Met Leu Gln Ile Ile Gln Glu Lys Arg Gly Tyr
            115                 120                 125
```

<210> SEQ ID NO 9
<211> LENGTH: 651
<212> TYPE: DNA
<213> ORGANISM: Mus musculus

<400> SEQUENCE: 9

```
gcgggtctac agaaccagga tagcagcagc catcctccag acggggcgat tgttccagag      60
tcagtaccat gagccacaat tctcaagcct tcttgtccac caatgccggg cttcctccaa     120
gctatgagac aatcaaagag gagtacgggg tgactgagct gggggaaccc agcaactcag     180
ctgttgtgag gaccaccgtg atcaacatgc ccagagaggt gtcggtgcct gaccatgtgg     240
```

```
tctggtccct gttcaataca ctcttcttca acgcctgctg cctgggcttc gttgcctatg      300
cctactctgt gaagtctagg gacaggaaga tggtgggcga tgtggttgga gcccaggcct      360
acgcctccac tgccaagtgc ctgaatatca gctccctgat cttcagcatc cttatggtca      420
ttatctgcat cattattttc tctaccacct ctgtggtagt ctttcagtct tttgcacaaa      480
gaacacccca ttctggattc tagctgccct gtgctccacg tccatatctg ccccgccccc      540
tgccccgccc ccaggctcaa gcctcgaccc tttaccctac gcgtatgcaa atgttacctt      600
cacctatctg tccacagtgg attcaataaa gtgcacgggg tggcaactct g              651
```

<210> SEQ ID NO 10
<211> LENGTH: 144
<212> TYPE: PRT
<213> ORGANISM: Mus musculus

<400> SEQUENCE: 10

```
Met Ser His Asn Ser Gln Ala Phe Leu Ser Thr Asn Ala Gly Leu Pro
1               5                  10                  15

Pro Ser Tyr Glu Thr Ile Lys Glu Glu Tyr Gly Val Thr Glu Leu Gly
            20                  25                  30

Glu Pro Ser Asn Ser Ala Val Val Arg Thr Thr Val Ile Asn Met Pro
        35                  40                  45

Arg Glu Val Ser Val Pro Asp His Val Val Trp Ser Leu Phe Asn Thr
    50                  55                  60

Leu Phe Phe Asn Ala Cys Cys Leu Gly Phe Val Ala Tyr Ala Tyr Ser
65                  70                  75                  80

Val Lys Ser Arg Asp Arg Lys Met Val Gly Asp Val Val Gly Ala Gln
                85                  90                  95

Ala Tyr Ala Ser Thr Ala Lys Cys Leu Asn Ile Ser Ser Leu Ile Phe
            100                 105                 110

Ser Ile Leu Met Val Ile Ile Cys Ile Ile Ile Phe Ser Thr Thr Ser
        115                 120                 125

Val Val Val Phe Gln Ser Phe Ala Gln Arg Thr Pro His Ser Gly Phe
    130                 135                 140
```

<210> SEQ ID NO 11
<211> LENGTH: 590
<212> TYPE: DNA
<213> ORGANISM: Mus musculus

<400> SEQUENCE: 11

```
tggagaaaag gccactgcgc aaagggctct ggacttctca gcttgtacca ccattctcat       60
tccttcctta ttctcaactc ttccagcctc aaaaaccaag agatgcctaa ggatcagcat      120
gaggtggttg taatggggac accccacacc tcaacttctt cgacaaccac cataatcacc      180
atgcctgaga tctccaagcc tgattatgtg gtctggtctc tgttcaatac actcttcatg      240
aacttctgct gcctgggttt catagcctat gcctactctg tgaagtctag ggacaggaag      300
atggtgggtg atatgactgg ggcccaggcc ttcgcctcca ctgccaggtg cctgaacatc      360
agctgcctga tcctctccgt cgtcatggtc atcctcttca tcactttctt tgccactaga      420
aggtagccat cttgtagcat ctcacagtag ataacagatt ctggggcctt ccgggcttgc      480
tatgtgttct attgtctatc gctgtcccaa accctagtct tagtcctgac catttacccc      540
atacatatgc aaatgttaca cttgcatatc tgttcattca ataaagtgca                 590
```

<210> SEQ ID NO 12
<211> LENGTH: 107
<212> TYPE: PRT
<213> ORGANISM: Mus musculus

<400> SEQUENCE: 12

Met Pro Lys Asp Gln His Glu Val Val Met Gly Thr Pro His Thr
1               5                   10                  15

Ser Thr Ser Ser Thr Thr Thr Ile Ile Thr Met Pro Glu Ile Ser Lys
                20                  25                  30

Pro Asp Tyr Val Val Trp Ser Leu Phe Asn Thr Leu Phe Met Asn Phe
            35                  40                  45

Cys Cys Leu Gly Phe Ile Ala Tyr Ala Tyr Ser Val Lys Ser Arg Asp
    50                  55                  60

Arg Lys Met Val Gly Asp Met Thr Gly Ala Gln Ala Phe Ala Ser Thr
65                  70                  75                  80

Ala Arg Cys Leu Asn Ile Ser Cys Leu Ile Leu Ser Val Val Met Val
                85                  90                  95

Ile Leu Phe Ile Thr Phe Phe Ala Thr Arg Arg
                100                 105

<210> SEQ ID NO 13
<211> LENGTH: 550
<212> TYPE: DNA
<213> ORGANISM: Mus musculus

<400> SEQUENCE: 13
gattccttcc ttattctcac tctgcagctt caaaagccga gagatgccta aggagcagca      60
agaggtggtt gtactggggt caccccacat ctcaacttct gcgacagcca ccacaatcaa    120
catgcctgag atctccacgc ctgaccatgt ggtctggtcc ctgttcaata cactcttcat    180
gaacttctgc tgcctgggct tcgtagccta tgcctactcc gtgaagtcta gggacaggaa    240
gatggtgggt gatacgactg ggcccaggc cttcgcctcc accgccaagt gcctgaacat     300
cagctccctg ttcttcacca tcctcacggc atcgtcgtc atcgttgtct gtgccattag     360
atgatgtgag atgtcttgca acatctcaca gtagataaca gattctgggg cctcccaggc    420
ttgctatgtg tttccttgtc tatcgctgcc ccaaacccta gacttagtcc tgaccatttg    480
ccccatacat atgcaaatgt gacactcaca aatctgtcca tggtggactc aataaagtgc    540
acgtgctgtg                                                            550

<210> SEQ ID NO 14
<211> LENGTH: 106
<212> TYPE: PRT
<213> ORGANISM: Mus musculus

<400> SEQUENCE: 14

Met Pro Lys Glu Gln Gln Glu Val Val Val Leu Gly Ser Pro His Ile
1               5                   10                  15

Ser Thr Ser Ala Thr Ala Thr Thr Ile Asn Met Pro Glu Ile Ser Thr
                20                  25                  30

Pro Asp His Val Val Trp Ser Leu Phe Asn Thr Leu Phe Met Asn Phe
            35                  40                  45

Cys Cys Leu Gly Phe Val Ala Tyr Ala Tyr Ser Val Lys Ser Arg Asp
    50                  55                  60

Arg Lys Met Val Gly Asp Thr Thr Gly Ala Gln Ala Phe Ala Ser Thr
65                  70                  75                  80

```
Ala Lys Cys Leu Asn Ile Ser Ser Leu Phe Phe Thr Ile Leu Thr Ala
            85                  90                  95

Ile Val Val Ile Val Val Cys Ala Ile Arg
            100                 105

<210> SEQ ID NO 15
<211> LENGTH: 499
<212> TYPE: DNA
<213> ORGANISM: Mus musculus

<400> SEQUENCE: 15
ctcagctagg aagacacggc gctggaaccc atggacactt catatccccg tgaggacccc      60
cgggctccat catcccgcaa ggctgatgct gcagcccaca cagccctctc catgggaaca    120
cctggcccta caccacgaga tcacatgctc tggtctgtct tcagcacgat gtacctgaat    180
ctgtgctgcc ttggattcct ggcgctggtc cactctgtca aggcccgaga ccagaagatg    240
gctgggaact ggaggctgc aaggcagtat ggctccaaag ccaagtgcta acatcctg       300 gctgcaatgt ggacattggt gccccattg ctgctcctgg gactggtggt gactggcgcc    360
ttgcacctgt ccaagttagc caaagactct gcggctttct tcagcaccaa gtttgatgag    420
gaggactata actaagagtt ccgagcctgt ccctgaaccg aggacaaccg ggctagagcg    480
gccgccaccg cggtggagc                                                499

<210> SEQ ID NO 16
<211> LENGTH: 134
<212> TYPE: PRT
<213> ORGANISM: Mus musculus

<400> SEQUENCE: 16

Met Asp Thr Ser Tyr Pro Arg Glu Asp Pro Arg Ala Pro Ser Ser Arg
1               5                   10                  15

Lys Ala Asp Ala Ala His Thr Ala Leu Ser Met Gly Thr Pro Gly
            20                  25                  30

Pro Thr Pro Arg Asp His Met Leu Trp Ser Val Phe Ser Thr Met Tyr
        35                  40                  45

Leu Asn Leu Cys Cys Leu Gly Phe Leu Ala Leu Val His Ser Val Lys
    50                  55                  60

Ala Arg Asp Gln Lys Met Ala Gly Asn Leu Glu Ala Ala Arg Gln Tyr
65                  70                  75                  80

Gly Ser Lys Ala Lys Cys Tyr Asn Ile Leu Ala Ala Met Trp Thr Leu
                85                  90                  95

Val Pro Pro Leu Leu Leu Leu Gly Leu Val Val Thr Gly Ala Leu His
            100                 105                 110

Leu Ser Lys Leu Ala Lys Asp Ser Ala Ala Phe Phe Ser Thr Lys Phe
        115                 120                 125

Asp Glu Glu Asp Tyr Asn
    130

<210> SEQ ID NO 17
<211> LENGTH: 445
<212> TYPE: DNA
<213> ORGANISM: Mus musculus

<400> SEQUENCE: 17
tgaacttcct tgaaacaaga gcttccttgc ttcctttaag cacaaaaaca tggttaagag     60
ggatcctgac tcagctccag tgccatccac tgtggtttgc atcaacagtg atgttatcca   120
```

-continued

```
gccggatcac attacctggt ctacatttaa cacagtgttc atgaatggct gctgcctggg      180
tttcattgcc tacatctact cggtgaagtc cagggaccgg aagatggtgg gcgacatgac      240
tggggcccaa tcccatgctt caaccgccaa gattctgaac atccttgctc tggtcatctc      300
cctcatcttc tacatcatgc ttatcgtttt atacagcttt aacttactag gtaaccaaag      360
ataatagaac cactagttag gtactaacta gttagttagc taattattaa ttaactaaac      420
tagtaccgaa tttagtatct ttagt                                            445
```

<210> SEQ ID NO 18
<211> LENGTH: 104
<212> TYPE: PRT
<213> ORGANISM: Mus musculus

<400> SEQUENCE: 18

```
Met Val Lys Arg Asp Pro Asp Ser Ala Pro Val Pro Ser Thr Val Val
1               5                   10                  15

Cys Ile Asn Ser Asp Val Ile Gln Pro Asp His Ile Thr Trp Ser Thr
            20                  25                  30

Phe Asn Thr Val Phe Met Asn Gly Cys Cys Leu Gly Phe Ile Ala Tyr
        35                  40                  45

Ile Tyr Ser Val Lys Ser Arg Asp Arg Lys Met Val Gly Asp Met Thr
    50                  55                  60

Gly Ala Gln Ser His Ala Ser Thr Ala Lys Ile Leu Asn Ile Leu Ala
65                  70                  75                  80

Leu Val Ile Ser Leu Ile Phe Tyr Ile Met Leu Ile Val Leu Tyr Ser
                85                  90                  95

Phe Asn Leu Leu Gly Asn Gln Arg
            100
```

<210> SEQ ID NO 19
<211> LENGTH: 137
<212> TYPE: PRT
<213> ORGANISM: Mus musculus

<400> SEQUENCE: 19

```
Met Asn His Thr Ser Gln Ala Phe Ile Thr Ala Ala Ser Gly Gly Gln
1               5                   10                  15

Pro Pro Asn Tyr Glu Arg Ile Lys Glu Glu Tyr Glu Val Ala Glu Met
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Ser Thr Leu Val
            100                 105                 110

Leu Ser Ile Leu Met Val Val Ile Thr Ile Val Ser Val Ile Ile Ile
        115                 120                 125

Val Leu Asn Ala Gln Asn Leu His Thr
    130                 135
```

-continued

<210> SEQ ID NO 20
<211> LENGTH: 150
<212> TYPE: PRT
<213> ORGANISM: Mus musculus

<400> SEQUENCE: 20

Met Glu Glu Pro Ser Glu Lys Val Asp Pro Met Lys Asp Pro Glu Thr
1               5                   10                  15

Pro Gln Lys Lys Asp Glu Glu Asp Ala Leu Asp Asp Thr Asp Val Leu
            20                  25                  30

Gln Pro Glu Thr Leu Val Lys Val Met Lys Lys Leu Thr Leu Asn Pro
        35                  40                  45

Gly Val Lys Arg Ser Ala Arg Arg Ser Leu Arg Asn Arg Ile Ala
    50                  55                  60

Ala Val Pro Val Glu Asn Lys Ser Glu Lys Ile Arg Arg Glu Val Gln
65                  70                  75                  80

Ser Ala Phe Pro Lys Arg Val Arg Thr Leu Leu Ser Val Leu Lys
                85                  90                  95

Asp Pro Ile Ala Lys Met Arg Arg Leu Val Arg Ile Glu Gln Arg Gln
            100                 105                 110

Lys Arg Leu Glu Gly Asn Glu Phe Glu Arg Asp Ser Glu Pro Phe Arg
        115                 120                 125

Cys Leu Cys Thr Phe Cys His Tyr Gln Arg Trp Asp Pro Ser Glu Asn
    130                 135                 140

Ala Lys Ile Gly Lys Asn
145                 150

<210> SEQ ID NO 21
<211> LENGTH: 133
<212> TYPE: PRT
<213> ORGANISM: Homo sapiens

<400> SEQUENCE: 21

Met Ser His Thr Val Gln Thr Phe Phe Ser Pro Val Asn Ser Gly Gln
1               5                   10                  15

Pro Pro Asn Tyr Glu Met Leu Lys Glu Glu His Glu Val Ala Val Leu
            20                  25                  30

Gly Gly Pro His Asn Pro Ala Pro Pro Thr Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
    130

<210> SEQ ID NO 22
<211> LENGTH: 132
<212> TYPE: PRT
<213> ORGANISM: Homo sapiens

<400> SEQUENCE: 22

Met Asp Thr Ala Tyr Pro Arg Glu Asp Thr Arg Ala Pro Thr Arg Ser
1               5                   10                  15

Lys Ala Gly Ala His Thr Ala Leu Ile Leu Gly Ala Pro His Pro Pro
            20                  25                  30

Pro Arg Asp His Leu Ile Trp Ser Val Phe Ser Thr Leu Tyr Leu Asn
        35                  40                  45

Leu Cys Cys Leu Gly Phe Leu Ala Leu Ala Tyr Ser Ile Lys Ala Arg
    50                  55                  60

Asp Cys Lys Val Val Gly Asp Leu Glu Ala Ala Arg Arg Phe Gly Ser
65                  70                  75                  80

Lys Ala Lys Cys Tyr Asn Ile Leu Ala Ala Met Trp Thr Leu Val Pro
                85                  90                  95

Pro Leu Leu Leu Leu Gly Leu Val Val Thr Gly Ala Leu His Leu Ala
            100                 105                 110

Arg Leu Ala Lys Asp Ser Ala Ala Phe Phe Ser Thr Lys Phe Asp Asp
        115                 120                 125

Ala Asp Tyr Asp
        130

<210> SEQ ID NO 23
<211> LENGTH: 146
<212> TYPE: PRT
<213> ORGANISM: Bos taurus

<400> SEQUENCE: 23

Met Asn Arg Thr Ser Gln Leu Leu Leu Thr Gly Ala His Gly Ala Val
1               5                   10                  15

Pro Pro Ala Tyr Glu Val Leu Lys Glu His Glu Val Ala Val Leu
            20                  25                  30

Gly Ala Pro Gln Ser Gln Ala Pro Leu Thr Thr Thr Val Ile Asn Ile
        35                  40                  45

Arg Ser Asp Thr Ala Val Pro Asp His Ile Val Trp Ser Leu Phe Asn
    50                  55                  60

Thr Ile Phe Met Asn Trp Cys Cys Leu Gly Phe Val Ala Phe Ala Tyr
65                  70                  75                  80

Ser Val Lys Ser Arg Asp Arg Lys Met Val Gly Asp Ile Thr Gly Ala
                85                  90                  95

Gln Ser Tyr Ala Ser Thr Ala Lys Cys Leu Asn Ile Cys Ser Leu Val
            100                 105                 110

Leu Gly Ile Leu Leu Thr Val Val Leu Ile Val Leu Val Ser Asn Gly
        115                 120                 125

Ser Leu Met Ile Val Gln Ala Val Ser Glu Leu Met Gln Asn Tyr Gly
    130                 135                 140

Gly His
145

<210> SEQ ID NO 24
<211> LENGTH: 125
<212> TYPE: PRT
<213> ORGANISM: Bos taurus

-continued

```
<400> SEQUENCE: 24

Met Ile Lys Glu Glu His Glu Val Ala Val Leu Gly Ala Pro Gln Ser
1               5                   10                  15

Arg Arg Pro Leu Thr Thr Thr Val Ile Asn Ile Arg Ser Asp Thr Ala
            20                  25                  30

Val Pro Asp His Ile Val Trp Ser Leu Phe Asn Thr Ile Phe Leu Asn
        35                  40                  45

Trp Cys Cys Leu Gly Phe Val Ala Phe Ala Tyr Ser Val Lys Ser Arg
    50                  55                  60

Asp Arg Lys Met Val Gly Asp Ile Thr Gly Ala Gln Ser Tyr Ala Ser
65                  70                  75                  80

Thr Ala Lys Cys Leu Asn Ile Trp Ala Leu Val Leu Gly Ile Leu Leu
                85                  90                  95

Thr Ile Gly Ser Ile Val Leu Leu Ile Phe Gly Tyr Met Ala Val Tyr
            100                 105                 110

Gln Thr Val Phe Leu Leu Met Gln Glu Lys Arg Gly His
        115                 120                 125

<210> SEQ ID NO 25
<211> LENGTH: 137
<212> TYPE: PRT
<213> ORGANISM: Rattus norvegicus

<400> SEQUENCE: 25

Met Asn His Thr Ser Gln Ala Phe Val Asn Ala Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Met Thr Gly Ala
                85                  90                  95

Gln Ala Tyr Ala Ser Thr Ala Lys Cys Leu Asn Ile Ser Ser Leu Val
            100                 105                 110

Leu Ser Ile Leu Met Val Ile Thr Ile Val Thr Val Val Ile Ile
        115                 120                 125

Ala Leu Asn Ala Pro Arg Leu Gln Thr
    130                 135

<210> SEQ ID NO 26
<211> LENGTH: 137
<212> TYPE: PRT
<213> ORGANISM: Rattus norvegicus

<400> SEQUENCE: 26

Met Asn His Thr Ser Gln Ala Phe Ala Thr Val Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45
```

```
Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Met Thr Gly Ala
            85                  90                  95

Gln Ala Tyr Ala Ser Thr Ala Lys Cys Leu Asn Ile Ser Ser Leu Val
            100                 105                 110

Leu Ser Ile Leu Met Val Ile Ile Thr Ile Val Thr Val Val Ile Ile
            115                 120                 125

Ala Leu Asn Ala Pro Arg Leu Gln Thr
            130                 135
```

<210> SEQ ID NO 27
<211> LENGTH: 144
<212> TYPE: PRT
<213> ORGANISM: Rattus norvegicus

<400> SEQUENCE: 27

```
Met Ser His Asn Ser Gln Ala Phe Leu Pro Ala Asn Ala Gly Leu Pro
1               5                   10                  15

Pro Ser Tyr Glu Thr Ile Lys Glu Glu Tyr Gly Val Thr Glu Leu Gly
            20                  25                  30

Glu Pro Asn Asn Ser Ala Val Val Arg Thr Thr Val Ile Asn Met Pro
        35                  40                  45

Arg Glu Val Ser Val Pro Asp His Val Val Trp Ser Leu Phe Asn Thr
    50                  55                  60

Leu Phe Phe Asn Ala Cys Cys Leu Gly Phe Ile Ala Tyr Ala Tyr Ser
65                  70                  75                  80

Val Lys Ser Arg Asp Arg Lys Met Val Gly Asp Val Ile Gly Ala Gln
            85                  90                  95

Ala Tyr Ala Ser Thr Ala Lys Cys Leu Asn Ile Ser Ser Leu Ile Phe
            100                 105                 110

Ser Val Leu Met Val Ile Ile Cys Ile Ile Ile Phe Ser Thr Thr Ser
            115                 120                 125

Ala Val Val Phe Gln Ser Leu Ser Gln Arg Thr Pro His Ser Gly Phe
            130                 135                 140
```

<210> SEQ ID NO 28
<211> LENGTH: 93
<212> TYPE: PRT
<213> ORGANISM: Rattus norvegicus

<400> SEQUENCE: 28

```
Met Asn His Thr Ser Gln Ala Phe Val Asn Ala Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Val Ser Val Leu Glu Val Gly Val Met Val
            85                  90
```

```
<210> SEQ ID NO 29
<211> LENGTH: 156
<212> TYPE: PRT
<213> ORGANISM: Artificial sequence
<220> FEATURE:
<223> OTHER INFORMATION: Consensus
<220> FEATURE:
<221> NAME/KEY: MISC_FEATURE
<222> LOCATION: 9..11, 13, 22, 23, 30, 31, 36, 37, 42..44, 51
<223> OTHER INFORMATION: Xaa = no consensus
<220> FEATURE:
<221> NAME/KEY: MISC_FEATURE
<222> LOCATION: 52, 54, 73, 96, 112, 113, 115, 117, 121, 123, 124
<223> OTHER INFORMATION: Xaa = no consensus
<220> FEATURE:
<221> NAME/KEY: MISC_FEATURE
<222> LOCATION: (127)..(132),(134)..(149), 152, 153, 156
<223> OTHER INFORMATION: Xaa = no consensus

<400> SEQUENCE: 29

Met Asn His Thr Ser Gln Ala Phe Xaa Xaa Xaa Ala Xaa Gly Gly Gln
 1               5                  10                  15

Pro Pro Asn Tyr Glu Xaa Xaa Lys Glu Glu Tyr Glu Val Xaa Xaa Leu
            20                  25                  30

Gly Ala Pro Xaa Xaa Arg Lys Ser Ala Xaa Xaa Xaa Thr Thr Val Ile
        35                  40                  45

Asn Met Xaa Xaa Glu Xaa Ser Val Pro Arg Asp His Val Val Trp Ser
 50                  55                  60

Leu Phe Asn Thr Leu Phe Met Asn Xaa Cys Cys Leu Gly Phe Ile Ala
 65                  70                  75                  80

Tyr Ala Tyr Ser Val Lys Ser Arg Asp Arg Lys Met Val Gly Asp Xaa
                85                  90                  95

Thr Gly Ala Gln Ala Tyr Ala Ser Thr Ala Lys Cys Leu Asn Ile Xaa
            100                 105                 110

Xaa Leu Xaa Leu Xaa Ile Leu Met Xaa Ile Xaa Xaa Ile Val Xaa Xaa
        115                 120                 125

Xaa Xaa Xaa Xaa Leu Xaa Xaa Xaa Xaa Xaa Xaa Xaa Xaa Xaa Xaa Xaa
130                 135                 140

Xaa Xaa Xaa Xaa Xaa Phe Asp Xaa Xaa Asp Tyr Xaa
145                 150                 155

<210> SEQ ID NO 30
<211> LENGTH: 158
<212> TYPE: PRT
<213> ORGANISM: Rattus norvegicus

<400> SEQUENCE: 30

Met Asp Glu Pro Ser Glu Lys Val Asp Pro Val Val Asn Pro Glu Thr
 1               5                  10                  15

Gln Met Tyr Asp Gly Ser Gln Arg Glu Asp Glu Gly Asp Ser Pro Asp
            20                  25                  30

Asp Ser Glu Ile Leu Gln Pro Glu Thr Leu Val Lys Val Met Lys Lys
        35                  40                  45

Leu Thr Leu Asn Pro Ser Ala Lys Pro Thr Lys Tyr His Arg Arg Gln
 50                  55                  60

Arg Val Arg Leu Gln Val Lys Ser Gln Pro Val Glu Asn Arg Ser Glu
 65                  70                  75                  80

Arg Ile Met Arg Glu Val Gln Ser Ala Phe Pro Arg Arg Val Arg
                85                  90                  95

Thr Leu Leu Ser Val Leu Lys Asp Pro Ile Ala Arg Met Arg Arg Phe
            100                 105                 110
```

-continued

```
Val Arg Ile Glu Gln Arg Gln Arg Gln Leu Glu Gly Asn Glu Arg Arg
        115                 120                 125

Asp Glu Pro Phe Arg Cys Leu Cys Thr Phe Cys His Tyr Gln Arg Trp
    130                 135                 140

Asp Pro Ser Glu Asn Ala Lys Ile Gly Gln Asn Gln Lys Asn
145                 150                 155

<210> SEQ ID NO 31
<211> LENGTH: 12
<212> TYPE: DNA
<213> ORGANISM: Artificial sequence
<220> FEATURE:
<223> OTHER INFORMATION: Interferon stimulable response element
<220> FEATURE:
<221> NAME/KEY: misc_feature
<222> LOCATION: (6)..(7)
<223> OTHER INFORMATION: n is a or g or c or t

<400> SEQUENCE: 31
ggaaanngaa ac                                                              12

<210> SEQ ID NO 32
<211> LENGTH: 11
<212> TYPE: DNA
<213> ORGANISM: Artificial sequence
<220> FEATURE:
<223> OTHER INFORMATION: Interferon stimulable response element
<220> FEATURE:
<221> NAME/KEY: misc_feature
<222> LOCATION: (6)..(6)
<223> OTHER INFORMATION: n is a or g or c or t

<400> SEQUENCE: 32
ggaaangaaa c                                                               11

<210> SEQ ID NO 33
<211> LENGTH: 17
<212> TYPE: PRT
<213> ORGANISM: Mus musculus

<400> SEQUENCE: 33

Ala Ser Gly Gly Gln Pro Pro Asn Tyr Glu Arg Ile Lys Glu Glu Tyr
1               5                   10                  15

Glu

<210> SEQ ID NO 34
<211> LENGTH: 16
<212> TYPE: PRT
<213> ORGANISM: Mus musculus

<400> SEQUENCE: 34

Arg Asp Arg Lys Met Val Gly Asp Val Thr Gly Ala Gln Ala Tyr Ala
1               5                   10                  15

<210> SEQ ID NO 35
<211> LENGTH: 16
<212> TYPE: PRT
<213> ORGANISM: Mus musculus

<400> SEQUENCE: 35

Met Glu Glu Pro Ser Glu Lys Val Asp Pro Met Lys Asp Pro Glu Thr
1               5                   10                  15
```

<210> SEQ ID NO 36
<211> LENGTH: 17
<212> TYPE: PRT
<213> ORGANISM: Mus musculus

<400> SEQUENCE: 36

Cys His Tyr Gln Arg Trp Asp Pro Ser Glu Asn Ala Lys Ile Gly Lys
1               5                   10                  15

Asn

<210> SEQ ID NO 37
<211> LENGTH: 60
<212> TYPE: DNA
<213> ORGANISM: Artificial sequence
<220> FEATURE:
<223> OTHER INFORMATION: Primer

<400> SEQUENCE: 37
attggatcca ggccgctctg gacaaaatat gaatcctttt tttttttttt tttttttttt     60

<210> SEQ ID NO 38
<211> LENGTH: 22
<212> TYPE: DNA
<213> ORGANISM: Artificial sequence
<220> FEATURE:
<223> OTHER INFORMATION: Primer

<400> SEQUENCE: 38 gccataccttt gacccgcaga ag                                             22

<210> SEQ ID NO 39
<211> LENGTH: 22
<212> TYPE: DNA
<213> ORGANISM: Artificial sequence
<220> FEATURE:
<223> OTHER INFORMATION: Primer

<400> SEQUENCE: 39
aaatggcact cagttcagtg gg                                              22

<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40
cccaaagcac cttattttc tacc                                             24

<210> SEQ ID NO 41
<211> LENGTH: 21
<212> TYPE: DNA
<213> ORGANISM: Artificial sequence
<220> FEATURE:
<223> OTHER INFORMATION: Primer

<400> SEQUENCE: 41
ttggcgagtc tctgcaattg g                                               21

<210> SEQ ID NO 42
<211> LENGTH: 21
<212> TYPE: DNA
<213> ORGANISM: Artificial sequence
<220> FEATURE:
<223> OTHER INFORMATION: Primer

```
<400> SEQUENCE: 42
cactctactc agtcccttt c                                                    21

<210> SEQ ID NO 43
<211> LENGTH: 22
<212> TYPE: DNA
<213> ORGANISM: Artificial sequence
<220> FEATURE:
<223> OTHER INFORMATION: Primer

<400> SEQUENCE: 43
tgtgtcccag tctttattta ag                                                  22

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
aactcatcag aggtcgaagg a                                                   21

<210> SEQ ID NO 45
<211> LENGTH: 21
<212> TYPE: DNA
<213> ORGANISM: Artificial sequence
<220> FEATURE:
<223> OTHER INFORMATION: Primer

<400> SEQUENCE: 45
cggtgctatt gtaaggtctg c                                                   21

<210> SEQ ID NO 46
<211> LENGTH: 19
<212> TYPE: DNA
<213> ORGANISM: Artificial sequence
<220> FEATURE:
<223> OTHER INFORMATION: Primer

<400> SEQUENCE: 46
ctactccgtg aagtctagg                                                      19

<210> SEQ ID NO 47
<211> LENGTH: 21
<212> TYPE: DNA
<213> ORGANISM: Artificial sequence
<220> FEATURE:
<223> OTHER INFORMATION: Primer

<400> SEQUENCE: 47
aatgagtgtt acacctgcgt g                                                   21

<210> SEQ ID NO 48
<211> LENGTH: 21
<212> TYPE: DNA
<213> ORGANISM: Artificial sequence
<220> FEATURE:
<223> OTHER INFORMATION: Primer

<400> SEQUENCE: 48
gccattcaga tgtctctgca c                                                   21
```

```
<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
ctcacagctt gaggcttcta a                                          21

<210> SEQ ID NO 50
<211> LENGTH: 21
<212> TYPE: DNA
<213> ORGANISM: Artificial sequence
<220> FEATURE:
<223> OTHER INFORMATION: Primer

<400> SEQUENCE: 50
ctcacagctt gaggcttcta a                                          21

<210> SEQ ID NO 51
<211> LENGTH: 21
<212> TYPE: DNA
<213> ORGANISM: Artificial sequence
<220> FEATURE:
<223> OTHER INFORMATION: Primer

<400> SEQUENCE: 51
gcgattcaga tgtctctgca c                                          21

<210> SEQ ID NO 52
<211> LENGTH: 24
<212> TYPE: DNA
<213> ORGANISM: Artificial sequence
<220> FEATURE:
<223> OTHER INFORMATION: Primer

<400> SEQUENCE: 52
gttatcacca ttgttagtgt catc                                       24

<210> SEQ ID NO 53
<211> LENGTH: 21
<212> TYPE: DNA
<213> ORGANISM: Artificial sequence
<220> FEATURE:
<223> OTHER INFORMATION: Primer

<400> SEQUENCE: 53
aatgagtgtt acacctgcgt g                                          21

<210> SEQ ID NO 54
<211> LENGTH: 22
<212> TYPE: DNA
<213> ORGANISM: Artificial sequence
<220> FEATURE:
<223> OTHER INFORMATION: Primer

<400> SEQUENCE: 54
gatcttcagc atccttatgg tc                                         22

<210> SEQ ID NO 55
<211> LENGTH: 22
<212> TYPE: DNA
<213> ORGANISM: Artificial sequence
<220> FEATURE:
<223> OTHER INFORMATION: Primer
```

```
<400> SEQUENCE: 55
gaaggtaaca tttgcatacg cg                                        22

<210> SEQ ID NO 56
<211> LENGTH: 20
<212> TYPE: DNA
<213> ORGANISM: Artificial sequence
<220> FEATURE:
<223> OTHER INFORMATION: Primer

<400> SEQUENCE: 56
ccttccttat tctcactctg                                           20

<210> SEQ ID NO 57
<211> LENGTH: 20
<212> TYPE: DNA
<213> ORGANISM: Artificial sequence
<220> FEATURE:
<223> OTHER INFORMATION: Primer

<400> SEQUENCE: 57
gttgcaagac atctcacatc                                           20

<210> SEQ ID NO 58
<211> LENGTH: 21
<212> TYPE: DNA
<213> ORGANISM: Artificial sequence
<220> FEATURE:
<223> OTHER INFORMATION: Primer

<400> SEQUENCE: 58
aacttggagg ctgcaaggca g                                         21

<210> SEQ ID NO 59
<211> LENGTH: 22
<212> TYPE: DNA
<213> ORGANISM: Artificial sequence
<220> FEATURE:
<223> OTHER INFORMATION: Primer

<400> SEQUENCE: 59
ctcggaactc ttagttatag tc                                        22

<210> SEQ ID NO 60
<211> LENGTH: 20
<212> TYPE: DNA
<213> ORGANISM: Artificial sequence
<220> FEATURE:
<223> OTHER INFORMATION: Primer

<400> SEQUENCE: 60
tgctctggtc atctccctca                                           20

<210> SEQ ID NO 61
<211> LENGTH: 20
<212> TYPE: DNA
<213> ORGANISM: Artificial sequence
<220> FEATURE:
<223> OTHER INFORMATION: Primer

<400> SEQUENCE: 61
caggataagg ggcaactctg                                           20
```

```
<210> SEQ ID NO 62
<211> LENGTH: 22
<212> TYPE: DNA
<213> ORGANISM: Artificial sequence
<220> FEATURE:
<223> OTHER INFORMATION: Primer

<400> SEQUENCE: 62
caatttgagg ctctgtcatc ag                                          22

<210> SEQ ID NO 63
<211> LENGTH: 21
<212> TYPE: DNA
<213> ORGANISM: Artificial sequence
<220> FEATURE:
<223> OTHER INFORMATION: Primer

<400> SEQUENCE: 63
ttcatctcac tgactttggg c                                           21

<210> SEQ ID NO 64
<211> LENGTH: 20
<212> TYPE: DNA
<213> ORGANISM: Artificial sequence
<220> FEATURE:
<223> OTHER INFORMATION: Primer

<400> SEQUENCE: 64
agttcctggt ccacaacgtc                                             20

<210> SEQ ID NO 65
<211> LENGTH: 20
<212> TYPE: DNA
<213> ORGANISM: Artificial sequence
<220> FEATURE:
<223> OTHER INFORMATION: Primer

<400> SEQUENCE: 65
tgcacatgag ctgcctactc                                             20

<210> SEQ ID NO 66
<211> LENGTH: 21
<212> TYPE: DNA
<213> ORGANISM: Artificial sequence
<220> FEATURE:
<223> OTHER INFORMATION: Primer

<400> SEQUENCE: 66
agacgtccta caaccagaaa c                                           21

<210> SEQ ID NO 67
<211> LENGTH: 21
<212> TYPE: DNA
<213> ORGANISM: Artificial sequence
<220> FEATURE:
<223> OTHER INFORMATION: Primer

<400> SEQUENCE: 67
ccgaacaagt cttctcatct t                                           21
```